(12) United States Patent
Lee et al.

(10) Patent No.: US 8,318,325 B2
(45) Date of Patent: Nov. 27, 2012

(54) ANTHRACENE DERIVATIVES AND ORGANIC ELECTRONIC DEVICE USING SAME

(75) Inventors: Dong-Hoon Lee, Daejeon (KR); Hyun Nam, Daejeon (KR); Jun-Gi Jang, Daejeon (KR); Seong-So Kim, Paju-si (KR); Tae-Yoon Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 129 days.

(21) Appl. No.: 13/060,567

(22) PCT Filed: Sep. 24, 2009

(86) PCT No.: PCT/KR2009/005450
§ 371 (c)(1),
(2), (4) Date: Feb. 24, 2011

(87) PCT Pub. No.: WO2010/036036
PCT Pub. Date: Apr. 1, 2010

(65) Prior Publication Data
US 2011/0156017 A1  Jun. 30, 2011

(30) Foreign Application Priority Data
Sep. 24, 2008  (KR) ........................ 10-2008-0093757

(51) Int. Cl.
*H01L 51/54* (2006.01)

(52) U.S. Cl. ........ 428/690; 428/917; 313/504; 313/505; 313/506; 257/40; 257/E51.05; 257/E51.026; 257/E51.023; 546/195

(58) Field of Classification Search ................. 428/690, 428/917; 313/504, 505, 506; 257/40, E51.05, 257/E51.026, E51.032; 546/195
See application file for complete search history.

(56) References Cited

U.S. PATENT DOCUMENTS
2008/0111473 A1  5/2008  Kawamura et al.

FOREIGN PATENT DOCUMENTS
JP  2006-151844 A  6/2006
WO  WO 2007/102683 A1  9/2007

OTHER PUBLICATIONS

Buu-Hoi and Cagniant, Paul, "Steric hindrance in the Pfitzinger reaction. II. The action of a- and b-naphthisatin on aryl alkyl ketones", Bulletin de la Societe Chimique de France (1946), pp. 134-139.

*Primary Examiner* — Jennifer Chriss
*Assistant Examiner* — Gregory Clark
(74) *Attorney, Agent, or Firm* — McKenna Long & Aldridge LLP

(57) ABSTRACT

The present invention provides a novel anthracene derivatives and an organic electronic device using the same. The organic electronic device according to the present invention shows excellent properties in terms of efficiency, a driving voltage, and a life span.

18 Claims, 3 Drawing Sheets

ANTHRACENE DERIVATIVES AND ORGANIC ELECTRONIC DEVICE USING SAME

TECHNICAL FIELD

The present invention relates to a novel anthracene derivative and an organic electronic device using the same. This application claims priority to PCT/KR2009/005450, filed on Sep. 24, 2009 and Korean Patent Application No. 10-2008-0093757 filed on Sep. 24, 2008 both of which are hereby incorporated by reference in their entirety.

BACKGROUND ART

In the present specification, an organic electronic device is an electronic device using an organic semiconductor material, and requires exchanging of holes and/or electrons between electrodes and organic semiconductor materials. The organic electronic device may be largely divided into the following categories according to an operation principle. First, there is an electronic device in which an exiton is formed in an organic layer by a photon that flows from an external light source to the device, the exiton is separated into electrons and holes, and the electrons and the holes are transferred to the other electrodes and used as a current source (voltage source). Second, there is an electronic device in which holes and/or electrons are injected into organic semiconductor material layers forming an interface in respects to the electrode by applying a voltage or a current to two or more electrodes, and the device is operated by the injected electrons and holes.

As examples of the organic electronic device, there are an organic light emitting device, an organic solar cell, an organic photoconductor (OPC) drum, an organic transistor and the like, and all of them require an electron/hole injection material, an electron/hole extraction material, an electron/hole transport material or a light emitting material in order to drive the device. Hereinafter, an organic light emitting device will be mainly described in detail. However, in the organic electronic devices, all of the electron/hole injection material, an electron/hole extraction material, an electron/hole transport material or a light emitting material is operated on the basis of the similar principle.

In general, an organic light emitting phenomenon means a phenomenon that converts electric energy into light energy by using an organic material. The organic light emitting device using the organic light emitting phenomenon has a structure which generally includes an anode, a cathode, and an organic layer that is disposed between them. Herein, most organic layers have a multilayered structure that includes different materials in order to increase efficiency and stability of the organic light emitting device, and for example, it may include a hole injection layer, a hole transport layer, a light emitting layer, an electron transport layer, an electron injection layer and the like. In the organic light emitting device structure, if a voltage is applied between two electrodes, holes are injected from an anode to the organic layer and electrons are injected from a cathode to the organic layer, and when the injected holes and the electrons meet each other, an exciton is formed, and light is emitted when the exciton falls to a bottom state. It is known that this organic light emitting device has properties such as magnetic light emission, high brightness, high efficiency, low driving voltage, a wide viewing angle, high contrast, high speed response and the like.

In the organic light emitting device, the material that is used in the organic material layer may be classified into a light emitting material and an electric charge material, for example, a hole injection material, a hole transport material, an electron transport material, an electron injection material according to a function thereof. The light emitting material may be classified into blue, green, and red light emitting materials and yellow and orange light emitting materials in order to realize better natural colors according to the emission color. In addition, in order to increase color purity and increase emission efficiency through transferring of energy, a host/dopant system may be used as the light emitting material. In the principle, by mixing a dopant that has a energy bandwidth gap that is lower than that of host constituting mainly the light emitting layer and has excellent light emission efficiency with a light emitting layer in a small amount, the exciton that is generated in the host is transported to the dopant to ensure light having high efficiency. At this time, since the wavelength of the host is moved to the wavelength bandwidth of the dopant, a desired wavelength of light may be obtained according to the kind of dopant.

In order to sufficiently show excellent properties of the above organic light emitting device, a material constituting the organic material layer in the device, for example, the hole injection material, the hole transport material, the light emitting material, the electron transport material, the electron injection material and the like should be supported by stable and efficient materials. However, the development of a stable and efficient organic material layer material for organic light emitting devices has not yet been made. Therefore, there is a demand for developing a novel material.

DISCLOSURE

Technical Problem

Therefore, the present inventors have found a novel anthracene derivative. In addition, they have found the fact that in the case of when an organic material layer of an organic electron device is formed by using the novel anthracene derivative, effects such as an increase in efficiency of the device, a reduction in driving voltage, a lengthened life span, an increase in stability and the like can be obtained.

Therefore, the present invention aims to provide a novel anthracene derivative and an organic electronic device using the same.

Technical Solution

The present invention provides an anthracene derivative of the following Formula 1:

[Formula 1]

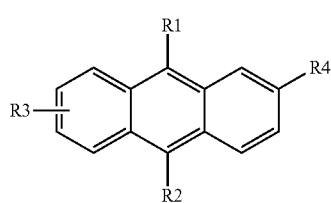

wherein R1 and R2 are the same as or different from each other, and are each independently selected from the group consisting of a $C_6 \sim C_{40}$ aryl group that is unsubstituted or substituted by at least one group that is selected from the group consisting of a halogen, an amino group, a nitrile group, a nitro group, a $C_1 \sim C_{40}$ alkyl group, a $C_2 \sim C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;

a $C_2$~$C_{40}$ heteroaryl group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group; and an arylamino group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group, R3 is selected from the group consisting of hydrogen; a $C_1$~$C_{40}$ alkyl group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;

a $C_3$~$C_{40}$ cycloalkyl group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;

a $C_6$~$C_{40}$ aryl group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;

a $C_2$~$C_{40}$ heteroaryl group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group; and a $C_6$~$C_{40}$ arylamino group that is unsubstituted or substituted by at least one group that is selected from the group consisting of a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group, R4 is represented by the group selected from the following Formulas 2 to 4,

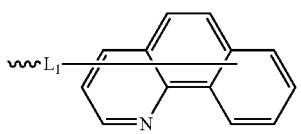

[Formula 2]

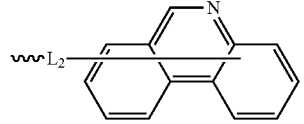

[Formula 3]

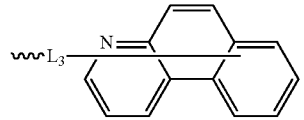

[Formula 4]

wherein $L_1$ to $L_3$ are each independently a direct bond; or are selected from the group consisting of a $C_2$~$C_{40}$ alkenylene group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;

a $C_6$~$C_{40}$ arylene group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;

a $C_2$~$C_{40}$ heteroarylene group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group; and a $C_6$~$C_{40}$ arylamino group that is unsubstituted or substituted by at least one group that is selected from the group consisting of a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group.

In addition, the present invention provides an organic electronic device which comprises a first electrode, a second electrode, and at least one organic material layer that is disposed between the first electrode and the second electrode, wherein at least one layer of the organic material layer comprises the anthracene derivative of Formula 1.

Advantageous Effects

The novel anthracene derivative according to the present invention may be used as a material of the organic light emitting device and the organic material layer of the organic electronic device, and the organic light emitting device using the same and the organic electronic device shows excellent properties in terms of an increase in efficiency of the device, a reduction in driving voltage, a lengthened life span, stability and the like.

BEST MODE

Figure 1:
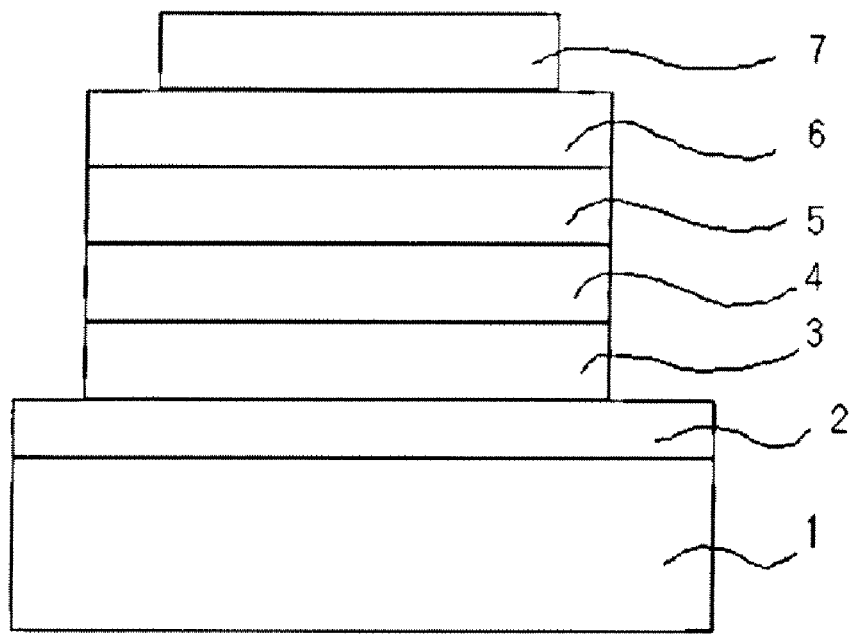
FIG. 1 is a view that illustrates an example of the organic light emitting device according to the present invention.
Figure 2:
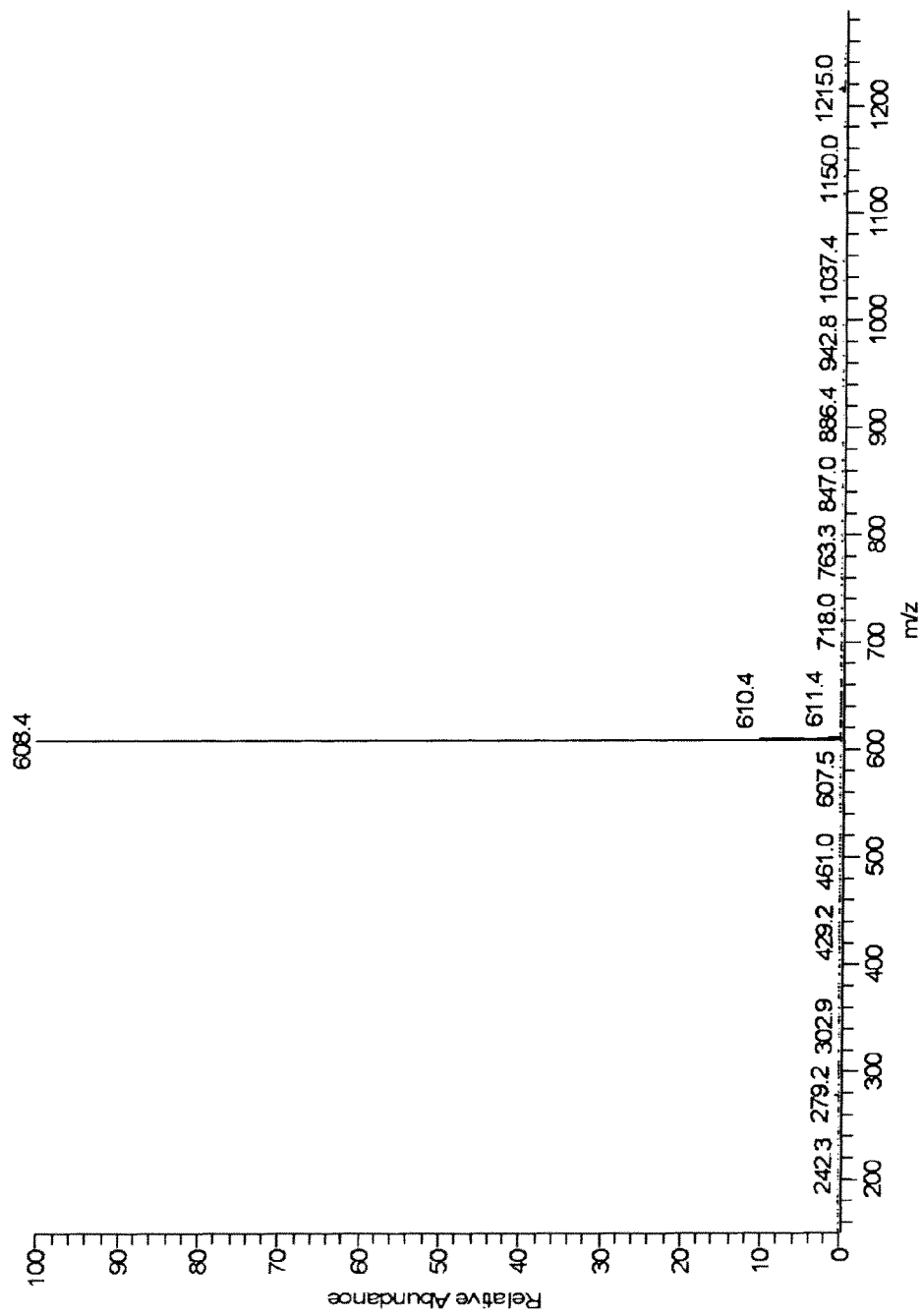
FIG. 2 is a MS graph of a compound of Formula 1-2 of the present invention.
Figure 3:
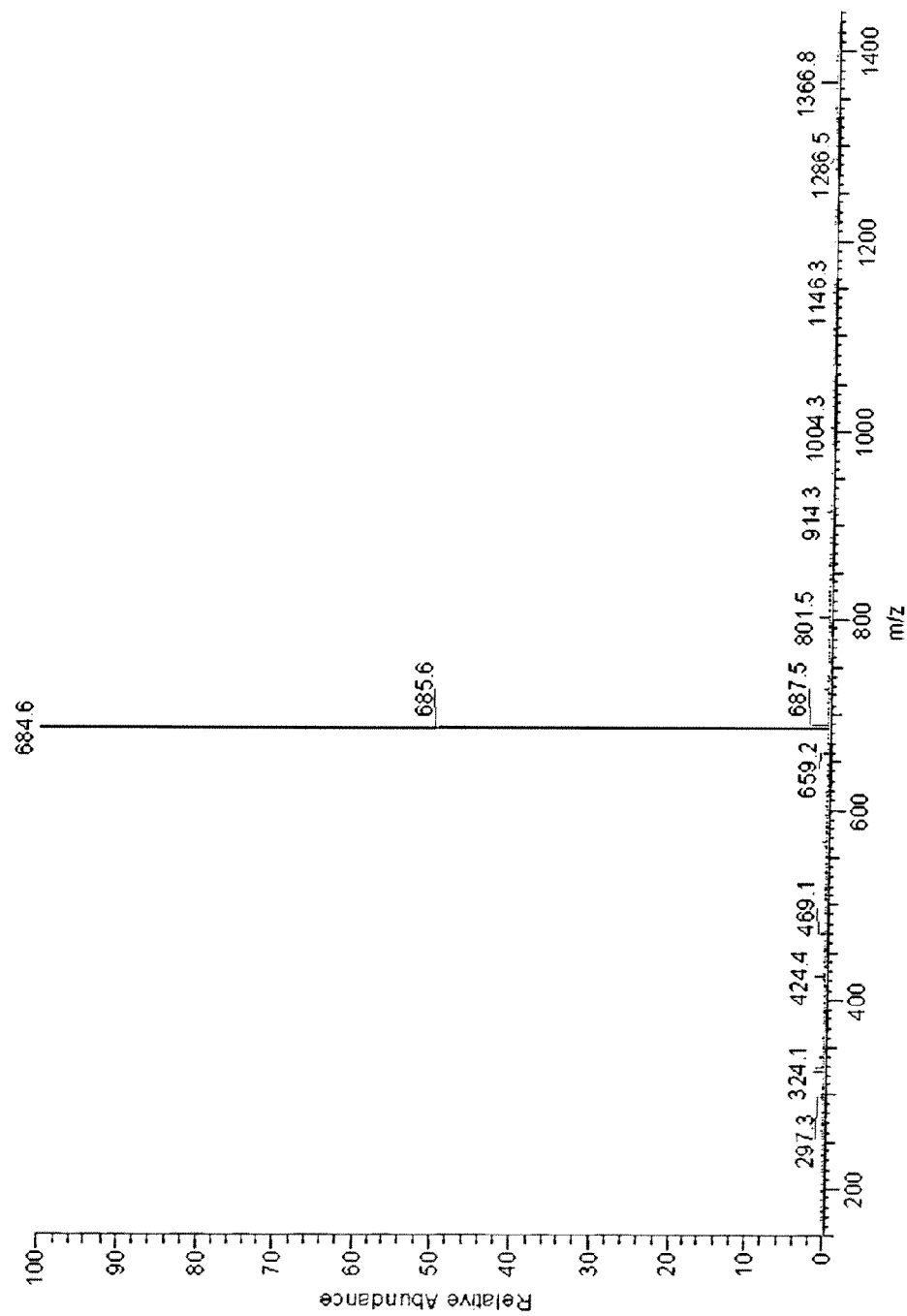
FIG. 3 is a MS graph of a compound of Formula 1-17 of the present invention.

The anthracene derivative according to the present invention is characterized in that it is a compound represented by Formula 1.

It is preferable that Formula 1 according to the present invention is selected from the compounds that are represented by the following Formulas 5 to 9, but it is not limited thereto.

[Formula 5]

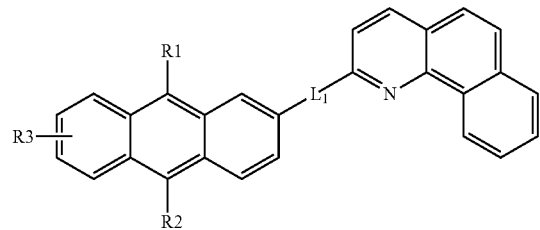

[Formula 6]

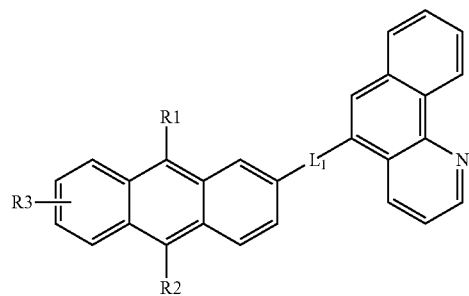

[Formula 7]

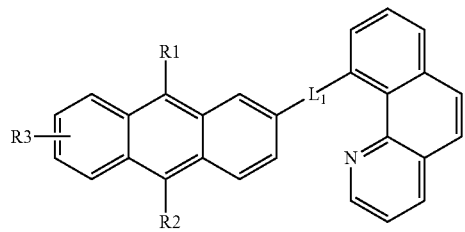

[Formula 8]

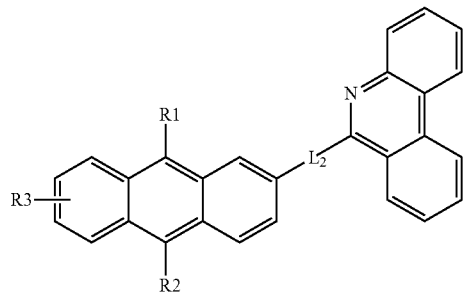

[Formula 9]

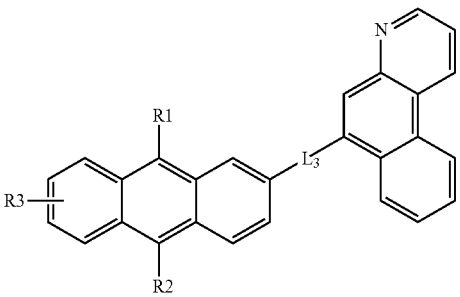

In Formulas 5 to 9, R1 to R3 and $L_1$ to $L_3$ are the same as those defined by Formula 1.

In an embodiment of the present invention, R1 and R2 of Formula 1 may be the same as each other and an aryl group. It is preferable that the aryl group is a substituted or unsubstituted phenyl group, a substituted or unsubstituted biphenyl group, a substituted or unsubstituted naphthyl group, a substituted or unsubstituted fluorene group, or a substituted or unsubstituted phenanthrene group.

In another embodiment of the present invention, R1 and R2 of Formula 1 may be the same as each other and a heteroaryl group. It is preferable that the heteroaryl group is a substituted or unsubstituted pyridyl group, a bipyridyl group, a quinoline group or an isoquinoline group.

In another embodiment of the present invention, R1 and R2 of Formula 1 may be the same as each other and a $C_6$~$C_{40}$ arylamino group that is substituted by a $C_6$~$C_{40}$ aryl group or a $C_2$~$C_{40}$ heteroaryl group.

In another embodiment of the present invention, R1 and R2 of Formula 1 may be selected from the group consisting of the following Structural Formulas.

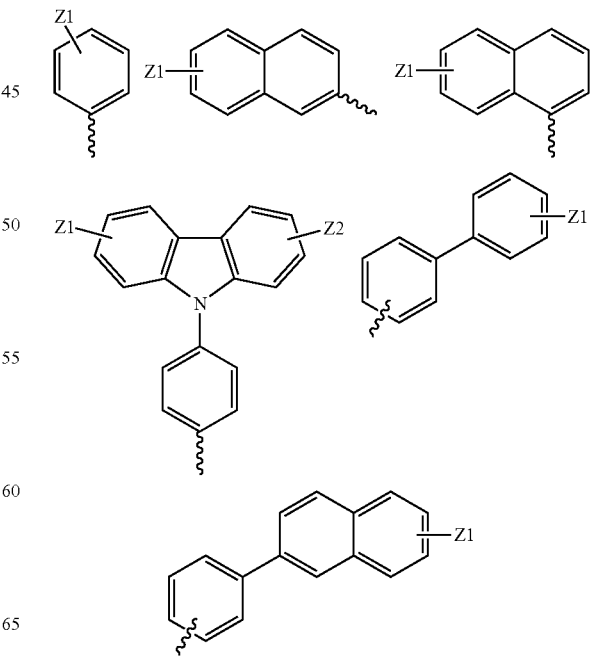

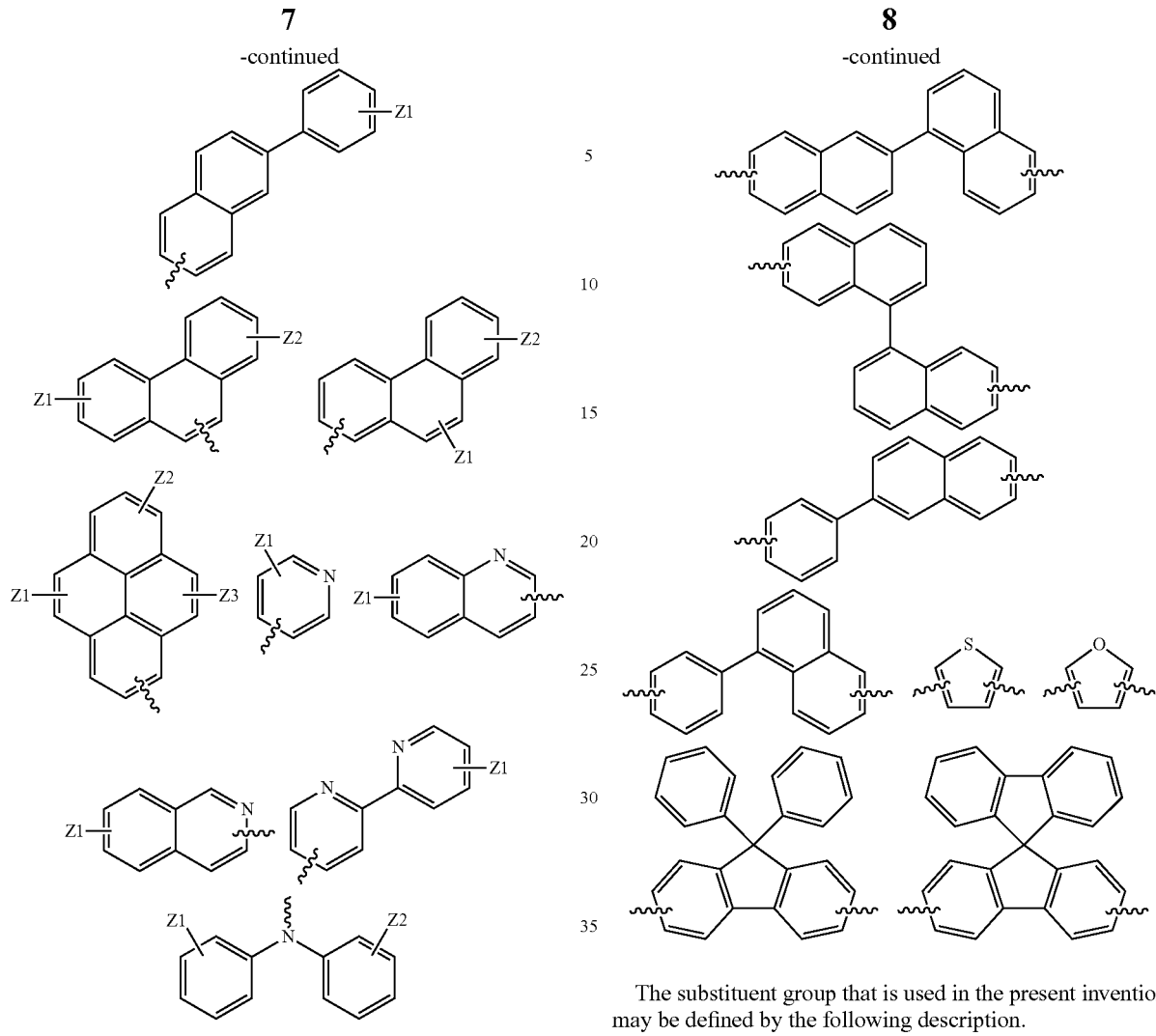

In the Structural Formula, Z1 to Z3 may be the same as or different from each other, and may be selected from the group consisting of hydrogen; a halogen; an amino group; a nitrile group; a nitro group; a $C_1$~$C_{40}$ alkyl group; a $C_2$~$C_{40}$ alkenyl group; a $C_1$~$C_{40}$ alkoxy group; a $C_3$~$C_{40}$ cycloalkyl group; a $C_2$~$C_{40}$ heterocycloalkyl group; a $C_6$~$C_{40}$ arylamino group; a $C_6$~$C_{40}$ aryl group and a $C_2$~$C_{40}$ heteroaryl group.

In another embodiment of the present invention, in Formulas 2 to 4, it is preferable that $L_1$ to $L_3$ are each independently a direct bond or selected from the group consisting of the following Structural Formulas:

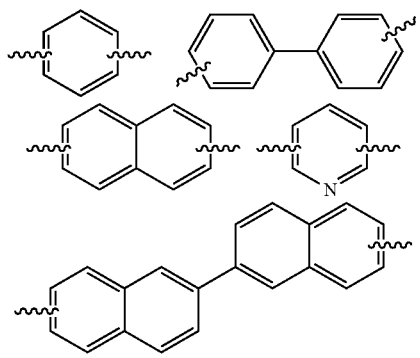

The substituent group that is used in the present invention may be defined by the following description.

It is preferable that the alkyl group does not provide steric obstruction of 1 to 40 carbon atoms. In detail, there are a methyl group, an ethyl group, a propyl group, isopropyl group, a butyl group, a t-butyl group, a pentyl group, a hexyl group and a heptyl group, but it is not limited thereto.

It is preferable that the cycloalkyl group does not provide steric obstruction of 3 to 40 carbon atoms. In detail, there are a cyclopentyl group, a cyclohexyl group and the like, but it is not limited thereto.

As the alkenyl group, an alkenyl group having 2 to 40 carbon atoms is preferable, and in detail, an alkenyl group that is substituted by the aryl group such as a stylbenyl group, a styrenyl group and the like are preferable, but it is not limited thereto.

It is preferable that the alkoxy group is an alkoxy group having 1 to 40 carbon atoms.

It is preferable that the aryl group has 6 to 40 carbon atoms. In detail, there are a phenyl group, a naphthyl group, an anthracenyl group, a biphenyl group, a pyrenyl group, a perylene group, a fluorene group, a phenanthrene group and a derivative thereof and the like, but it is not limited thereto.

As examples of the arylamino group, there are a phenylamino group, a naphthylamino group, a biphenylamino group, an anthracenylamino group, a 3-methyl-phenylamino group, a 4-methyl-naphthylamino group, a 2-methyl-biphenylamino group, a 9-methyl-anthracenylamino group, a diphenyl amino group, a phenyl naphthyl amino group, a ditolyl amino group, a phenyl tolyl amino group, a triphenyl amino group and the like, but it is not limited thereto.

As examples of the heteroaryl group, there are a pyridyl group, a bipyridyl group, a triazine group, an acrydyl group, a thiophene group, a furane group, an imidazole group, an oxazole group, a thiazole group, a triazole group, a quinoline group, an isoquinoline group, a carbazole group and the like, but it is not limited thereto.

As examples of the halogen group, there are a fluorine, a chlorine, a bromine, or an iodine.

The term "substituted or unsubstituted" means that it is unsubstituted or substituted by at least one group selected from the group consisting of a halogen, an amino group, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_2\text{~}C_{40}$ heteroaryl group.

As preferable detailed examples of the compound of Formula 1, there are the compounds of the following Formulas 1-1 to 1-120, but it is not limited thereto.

[Formula 1-1]

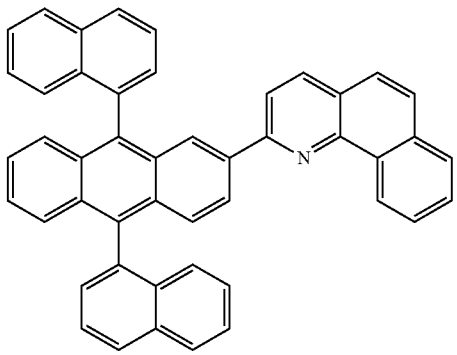

[Formula 1-2]

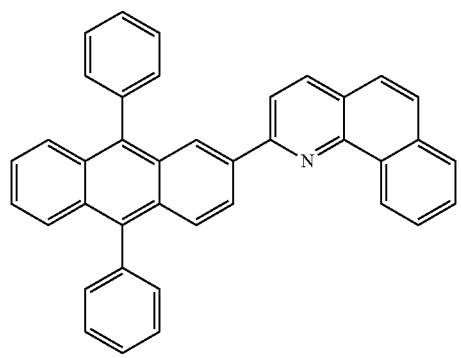

-continued

[Formula 1-3]

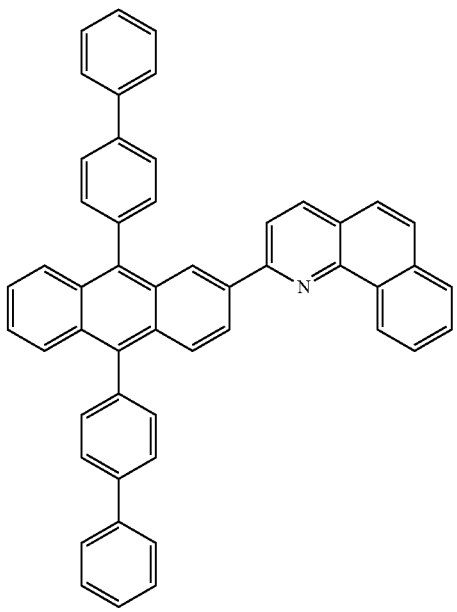

[Formula 1-4]

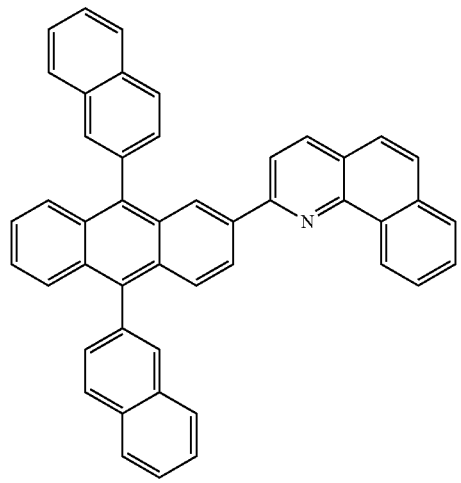

[Formula 1-5]

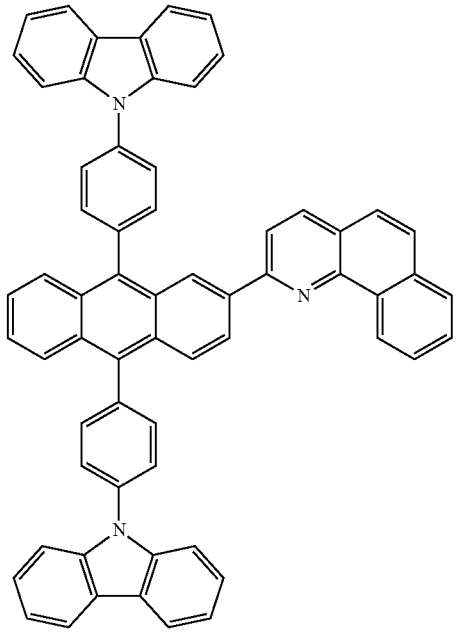

[Formula 1-6]
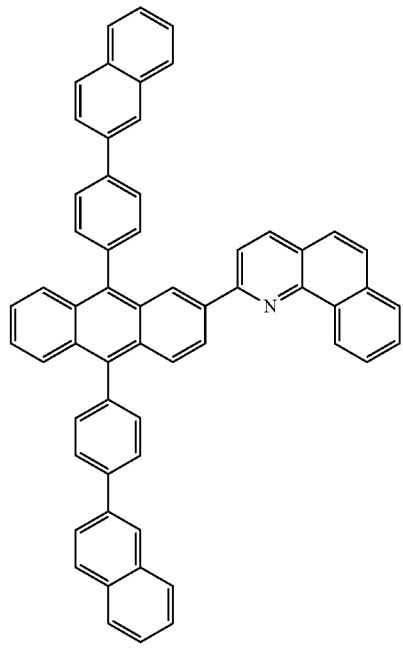
[Formula 1-7]
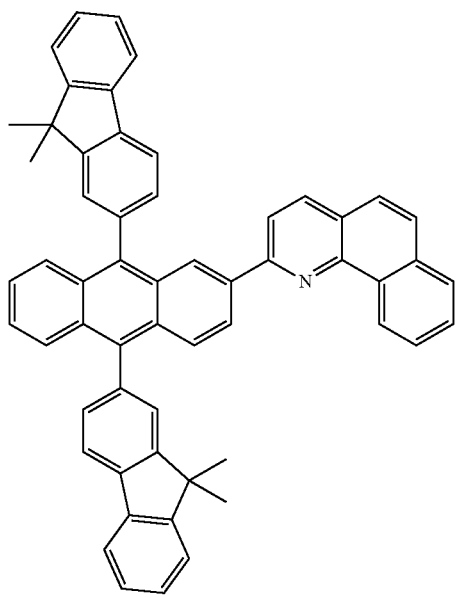
[Formula 1-8]
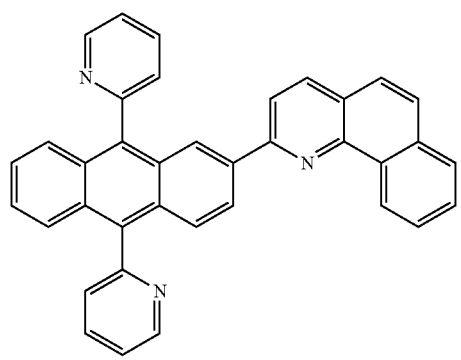
[Formula 1-9]
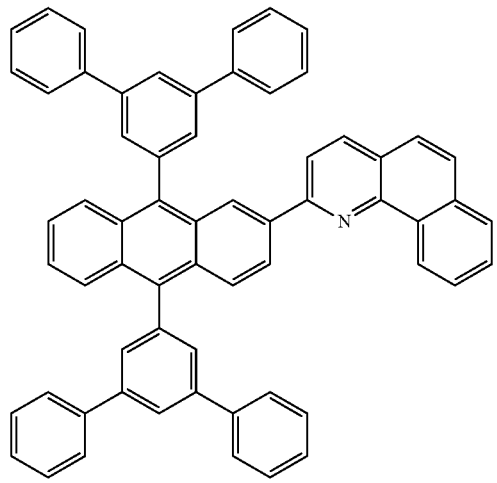
[Formula 1-10]
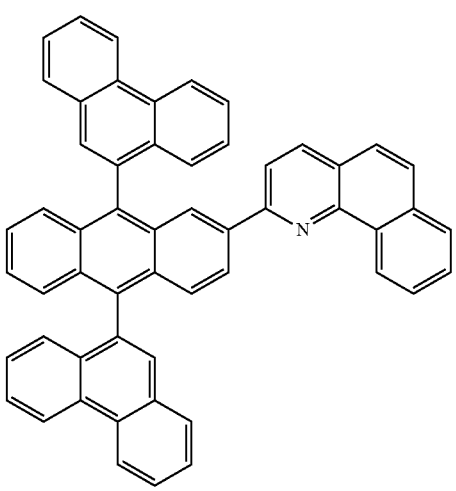
[Formula 1-11]
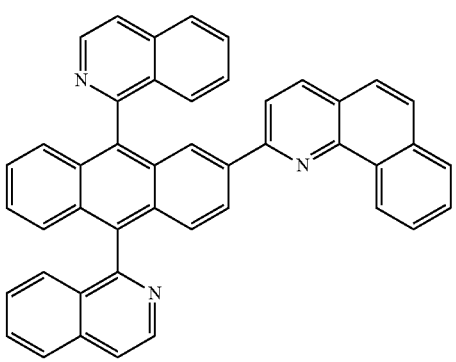

[Formula 1-12]
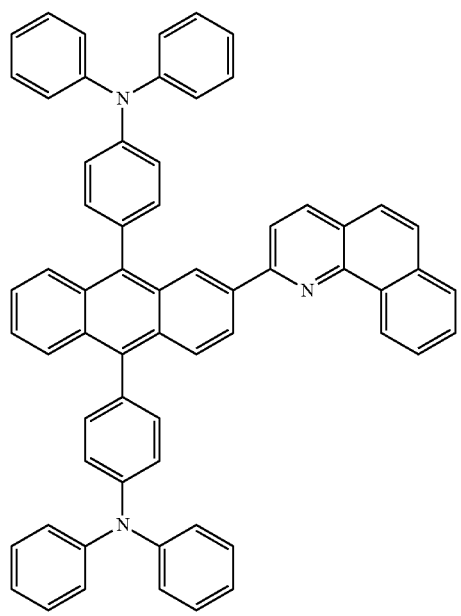
[Formula 1-13]
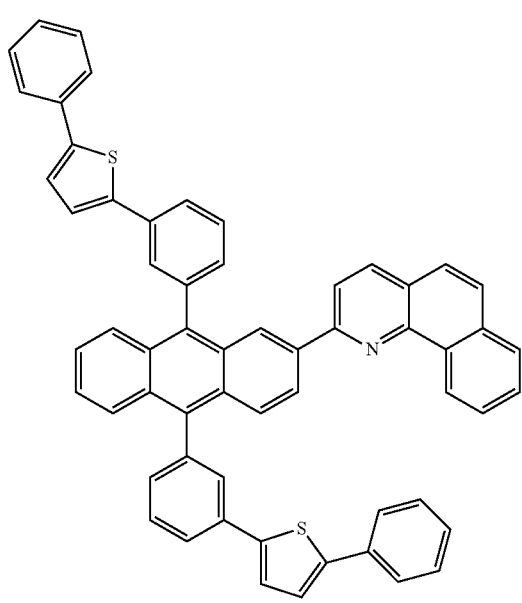
[Formula 1-14]
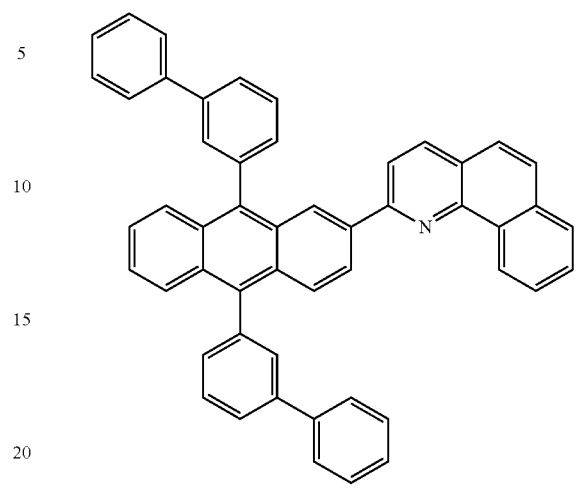
[Formula 1-15]
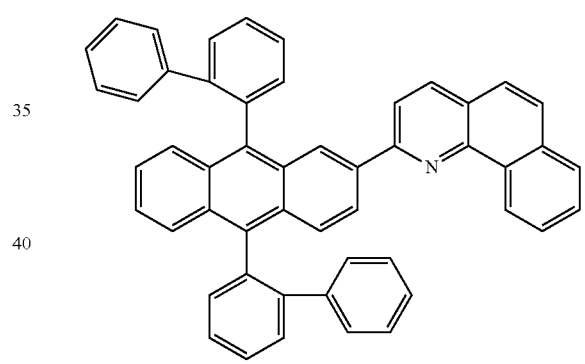
[Formula 1-16]
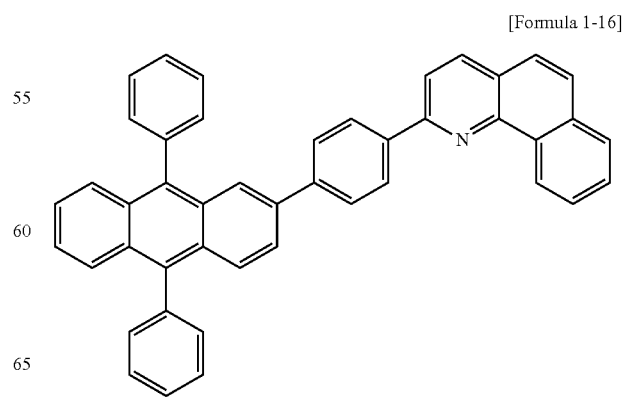

[Formula 1-17]
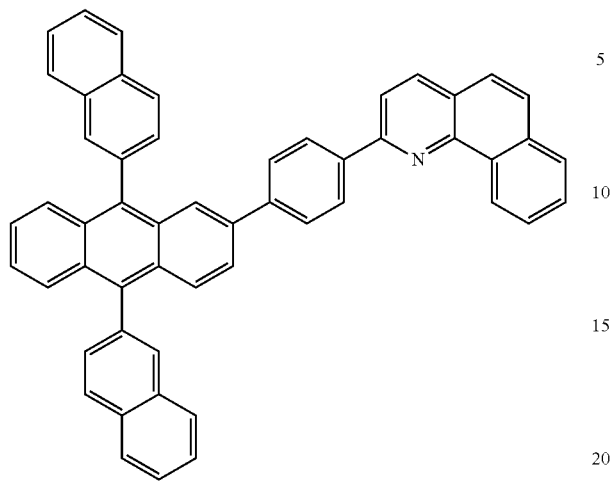
[Formula 1-18]
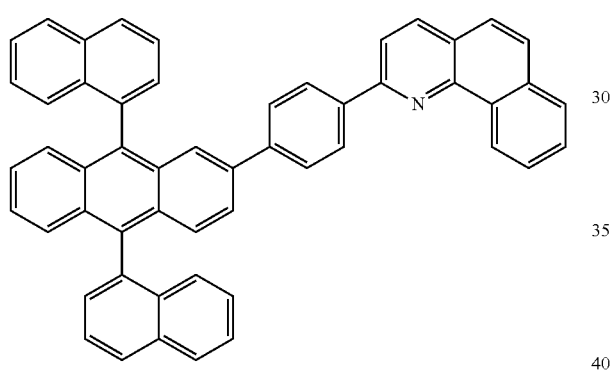
[Formula 1-19]
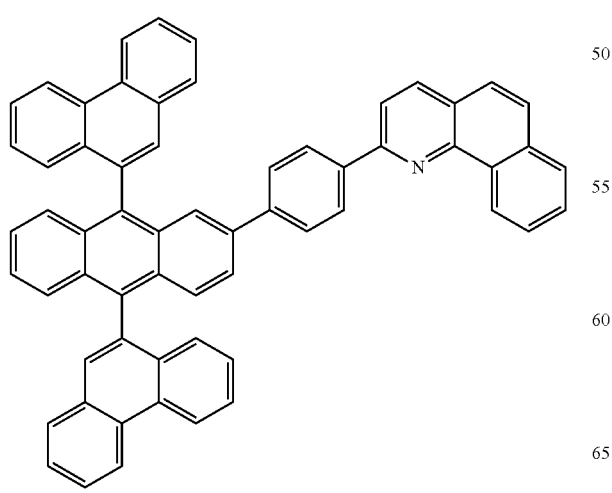
[Formula 1-20]
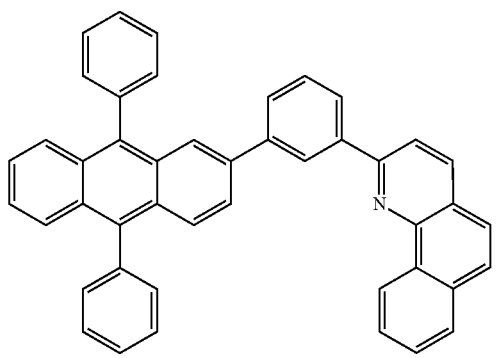
[Formula 1-21]
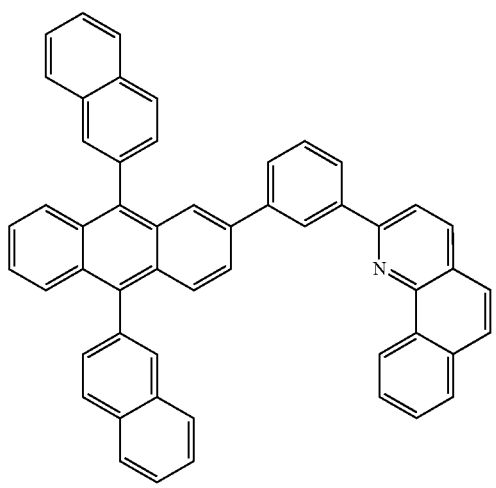
[Formula 1-22]
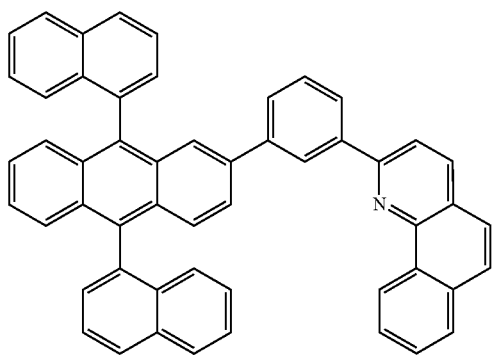

[Formula 1-23]
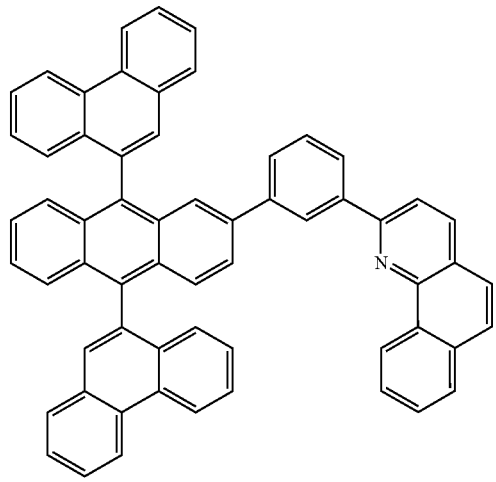
[Formula 1-24]
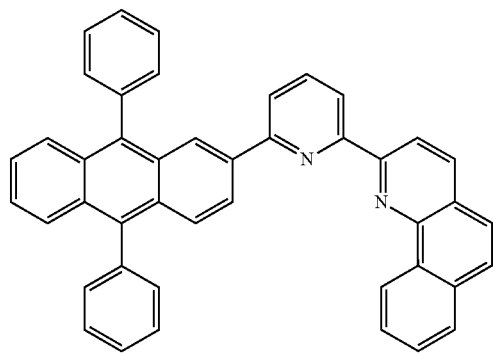
[Formula 1-25]
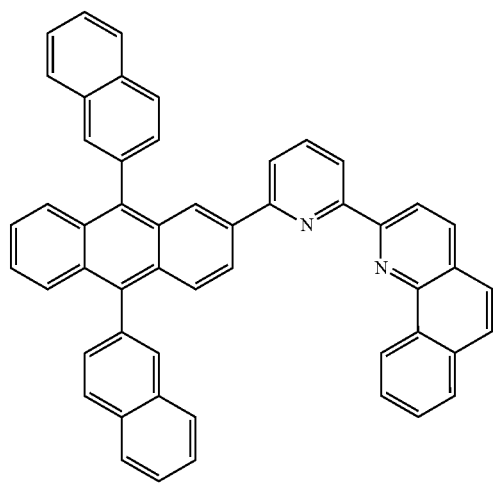
[Formula 1-26]
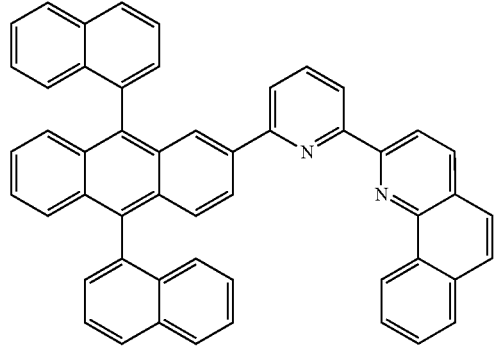
[Formula 1-27]
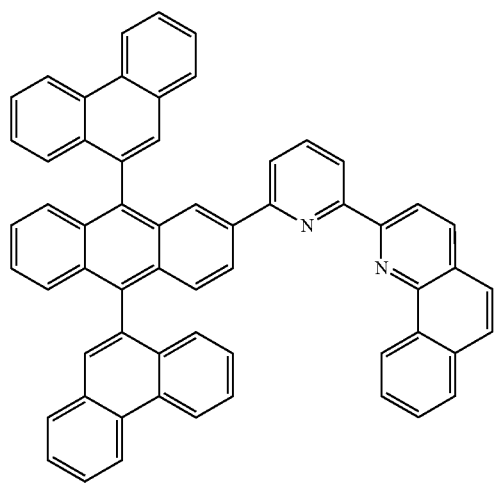
[Formula 1-28]
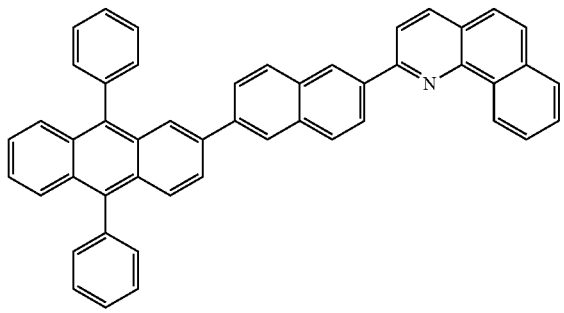
[Formula 1-29]
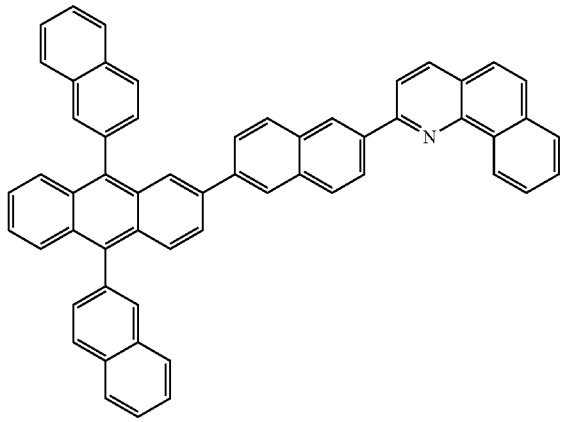

[Formula 1-30]
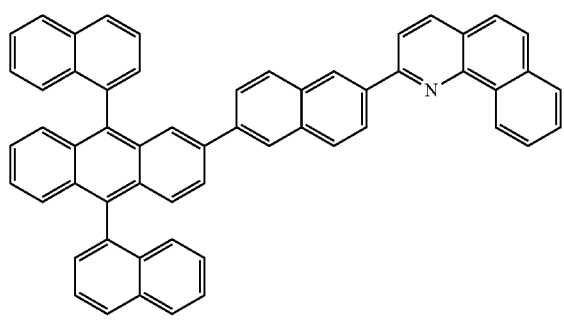
[Formula 1-33]
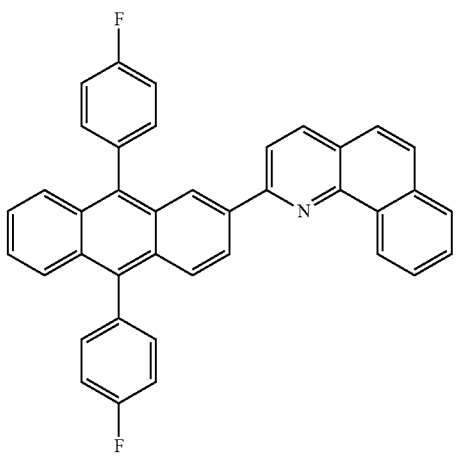
[Formula 1-31]
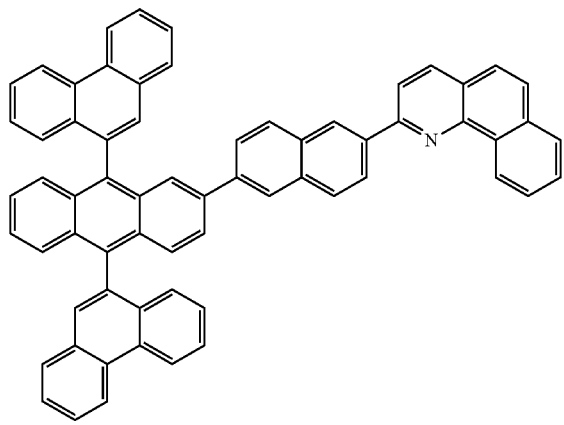
[Formula 1-34]
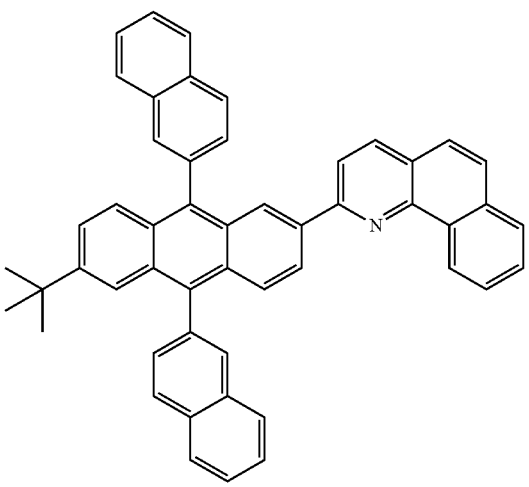
[Formula 1-32]
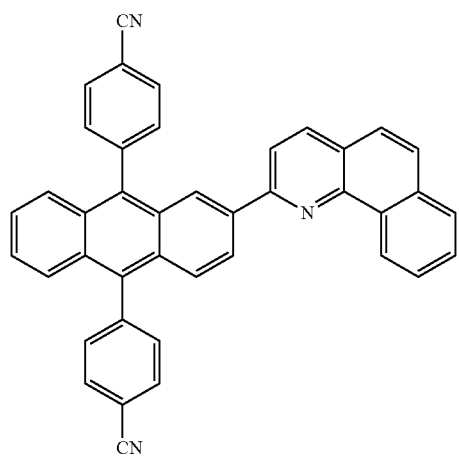
[Formula 1-35]
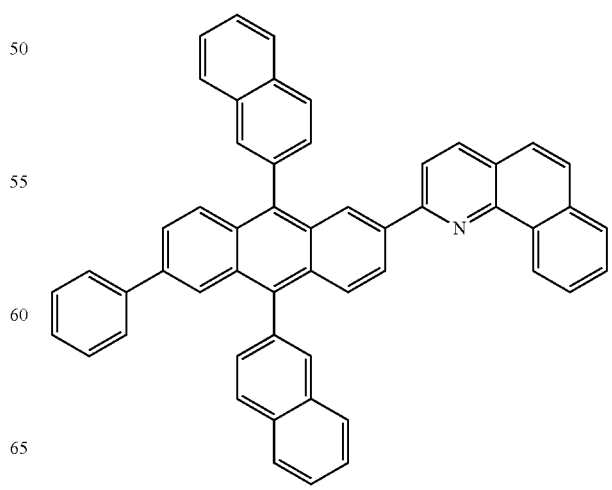

[Formula 1-36]
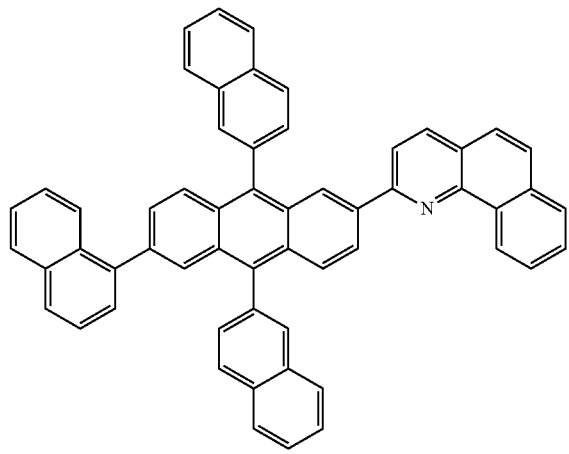
[Formula 1-37]
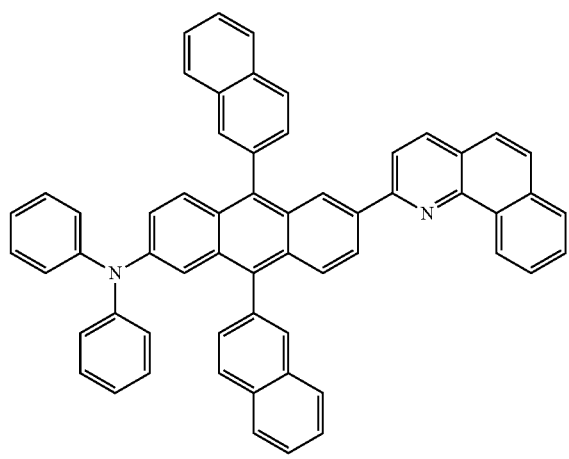
[Formula 1-38]
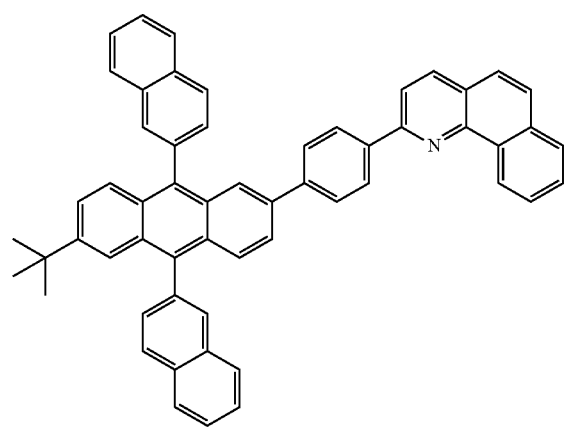
[Formula 1-39]
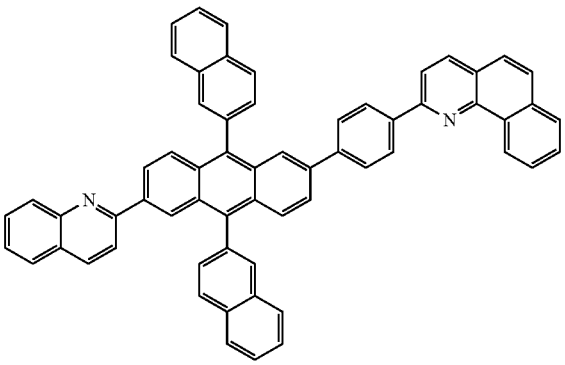
[Formula 1-40]
[Formula 1-41]
[Formula 1-42]

[Formula 1-43]
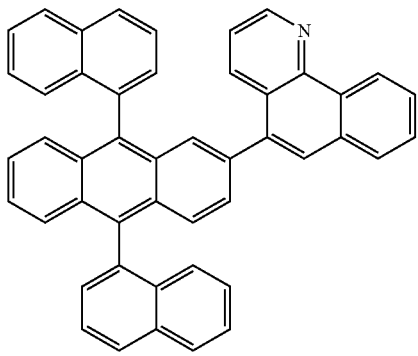
[Formula 1-44]
[Formula 1-45]
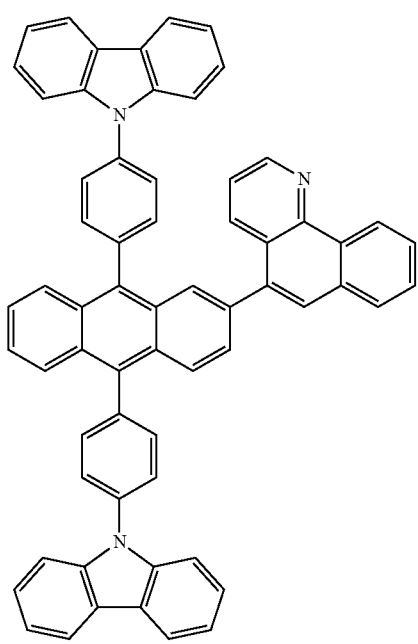
[Formula 1-46]
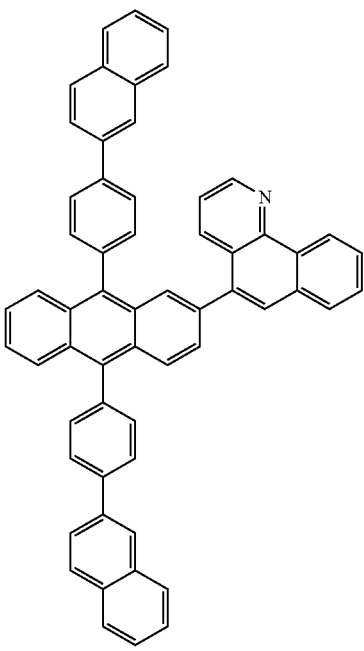
[Formula 1-47]
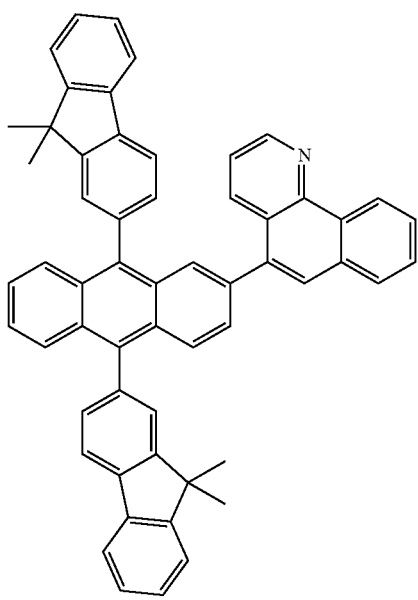
[Formula 1-48]
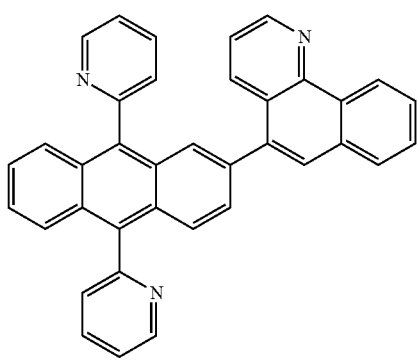

[Formula 1-49]
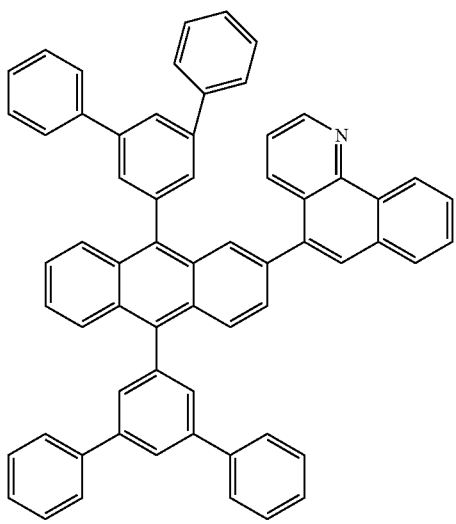
[Formula 1-50]
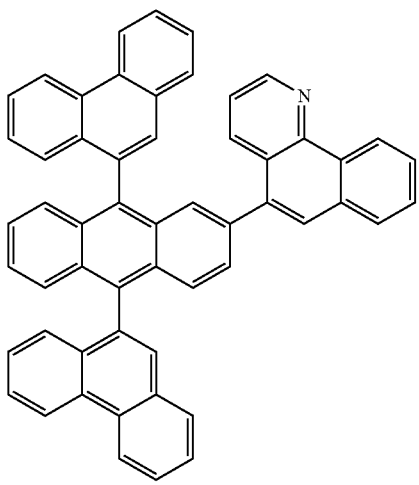
[Formula 1-51]
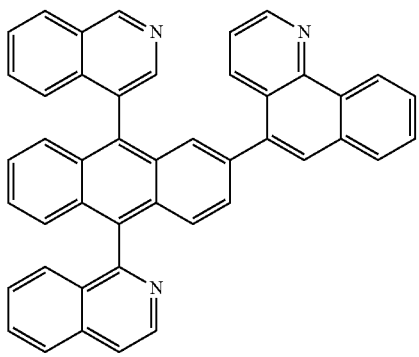
[Formula 1-52]
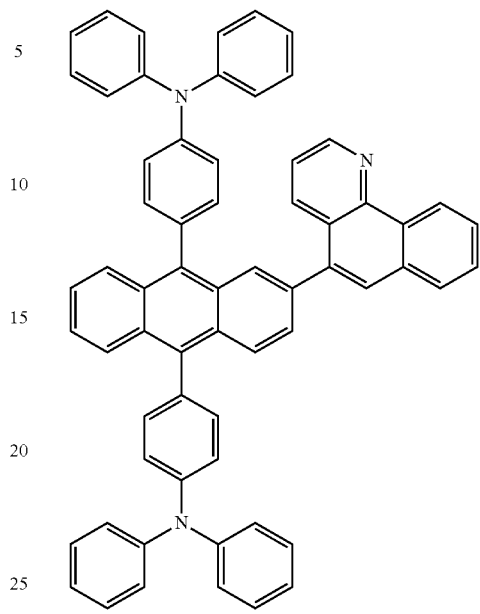
[Formula 1-53]
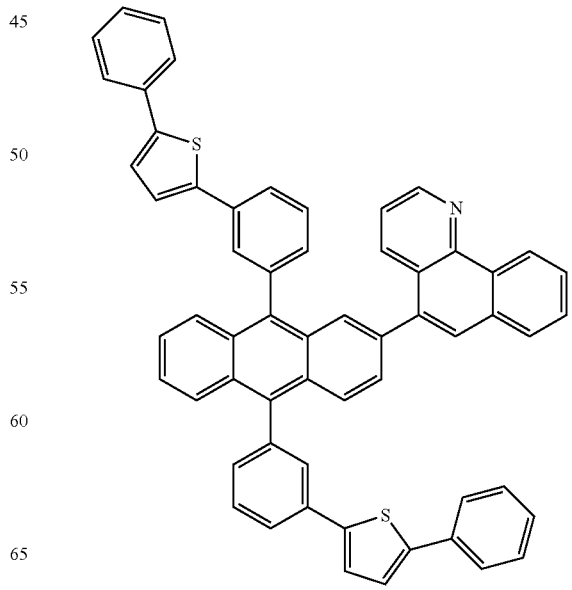

[Formula 1-54]
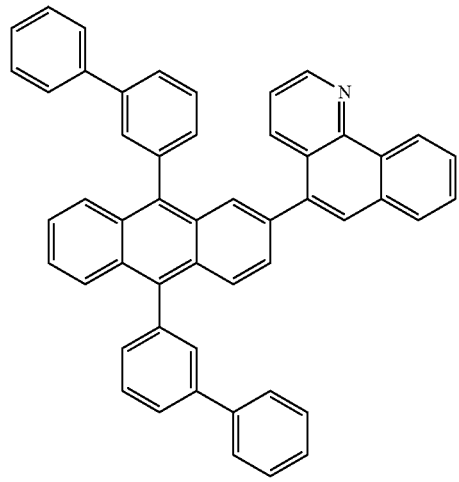
[Formula 1-55]
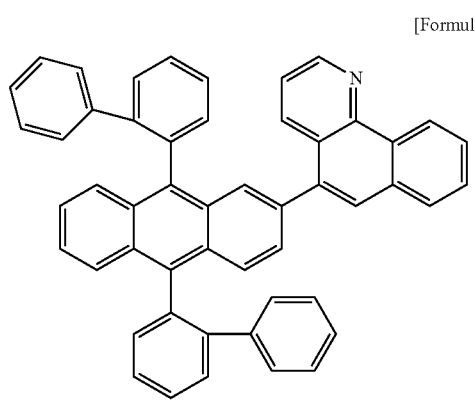
[Formula 1-56]
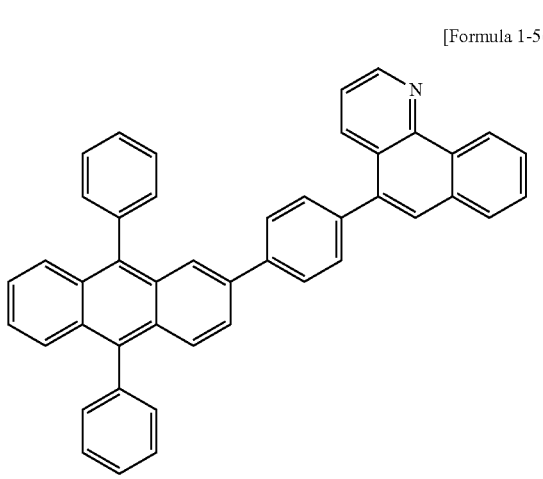
[Formula 1-57]
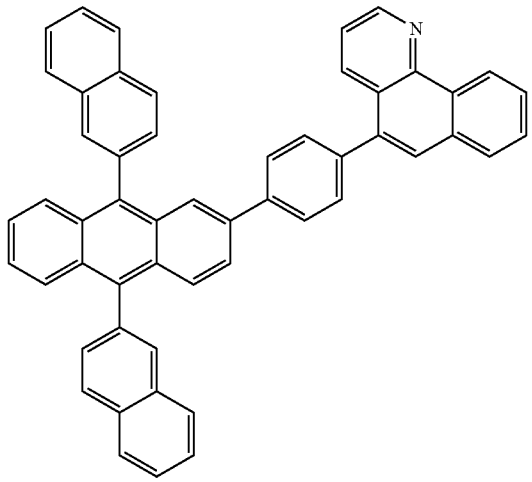
[Formula 1-58]
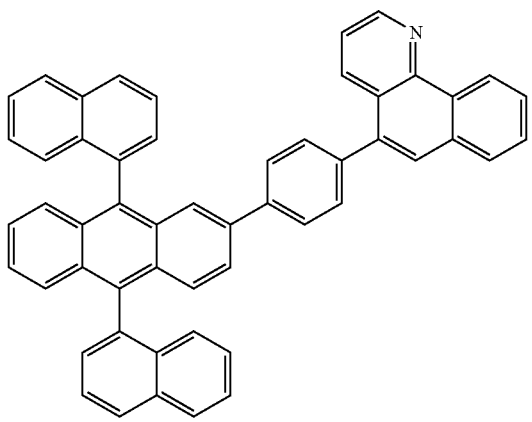
[Formula 1-59]
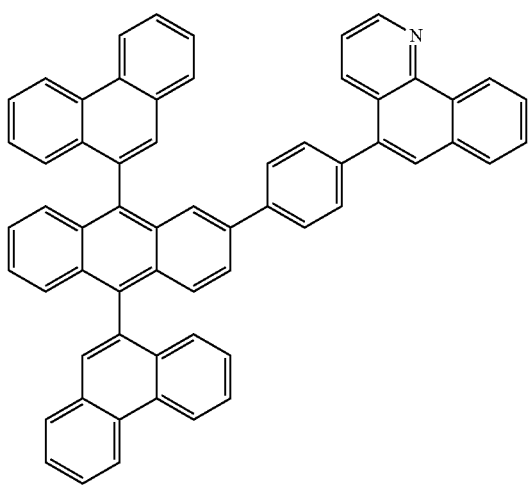

[Formula 1-60]
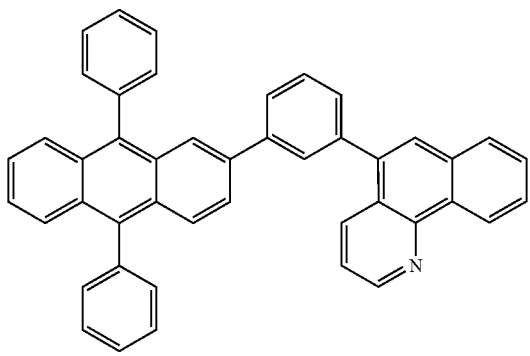
[Formula 1-63]
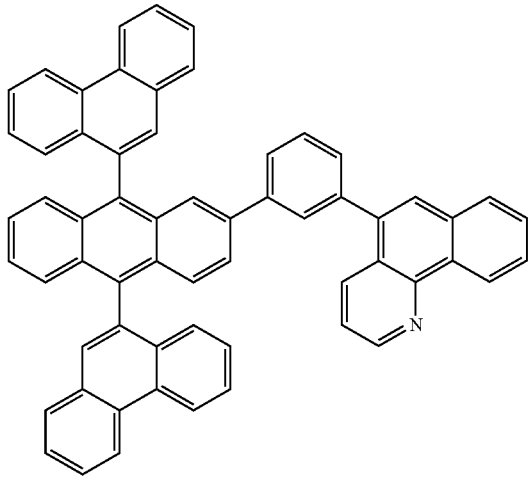
[Formula 1-61]
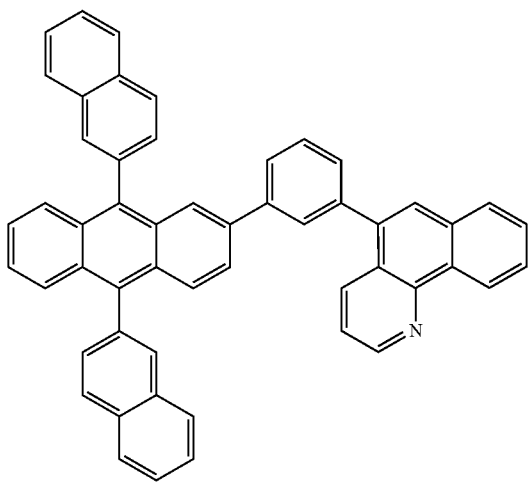
[Formula 1-64]
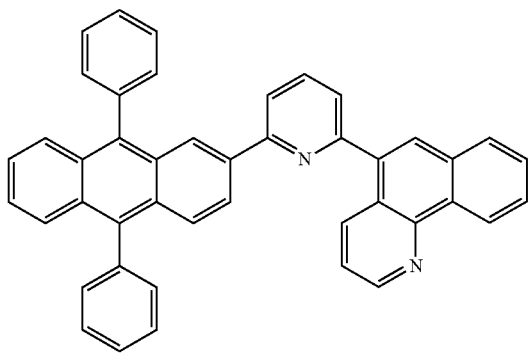
[Formula 1-62]
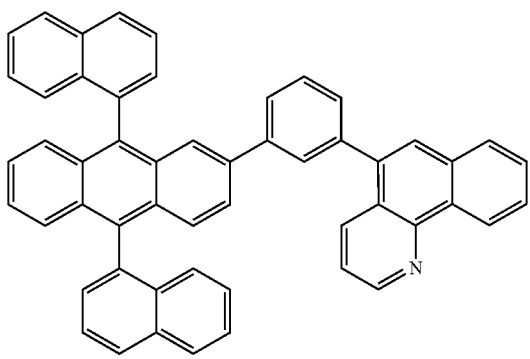
[Formula 1-65]
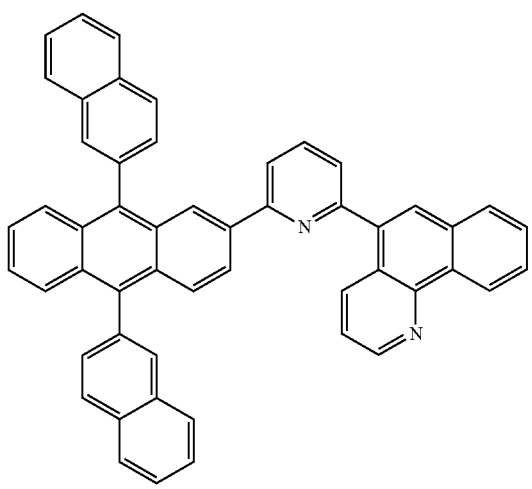

[Formula 1-66]
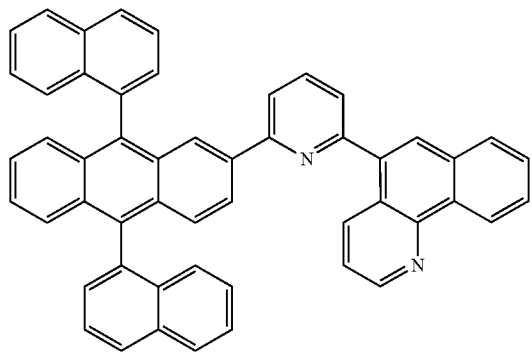
[Formula 1-67]
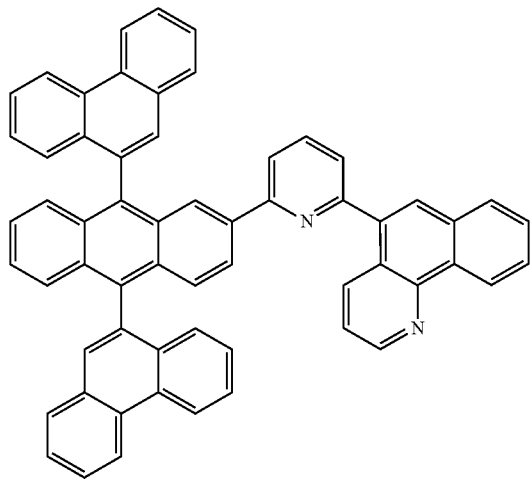
[Formula 1-68]
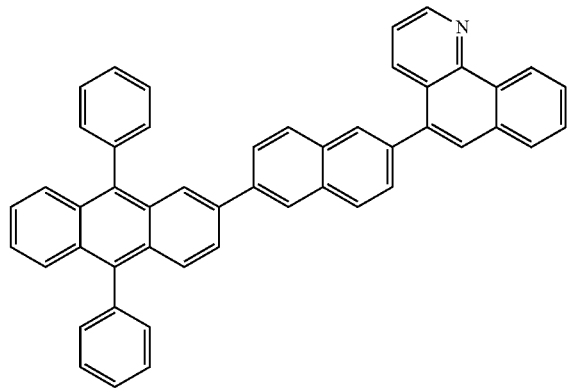
[Formula 1-69]
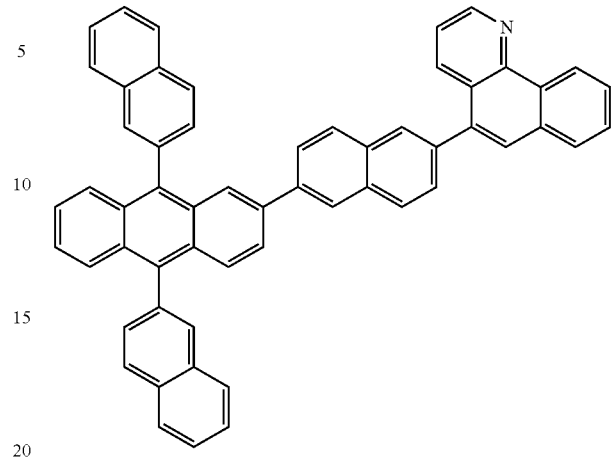
[Formula 1-70]
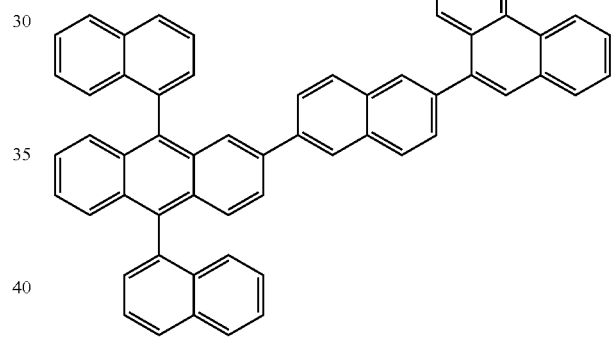
[Formula 1-71]
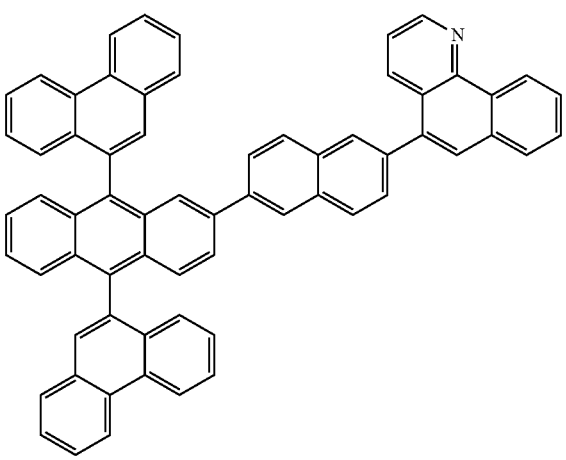

[Formula 1-72]
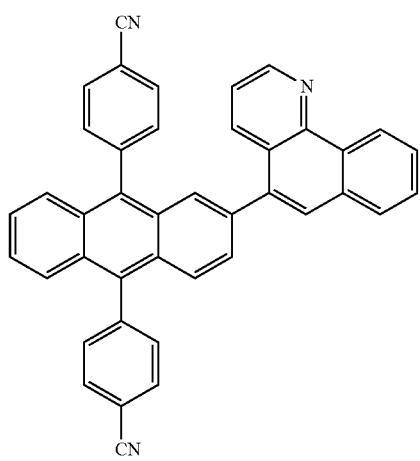
[Formula 1-73]
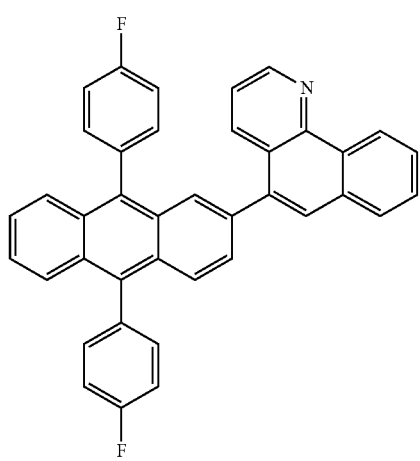
[Formula 1-74]
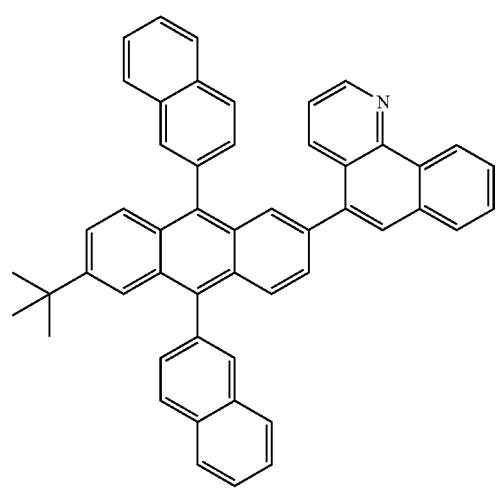
[Formula 1-75]
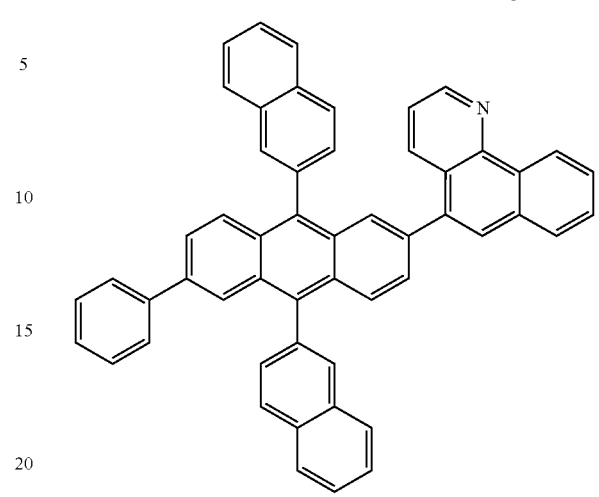
[Formula 1-76]
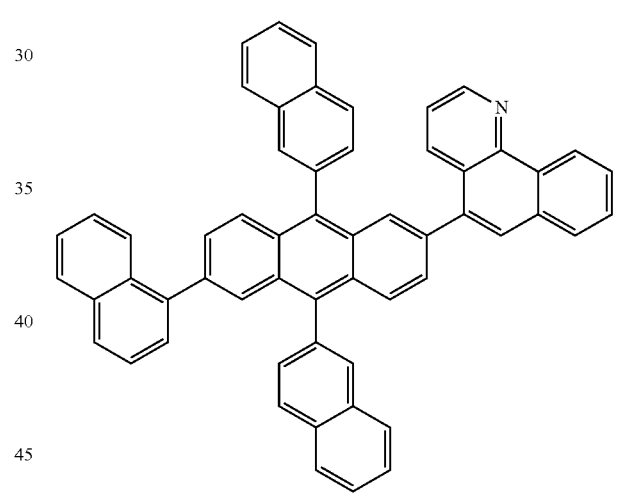
[Formula 1-77]
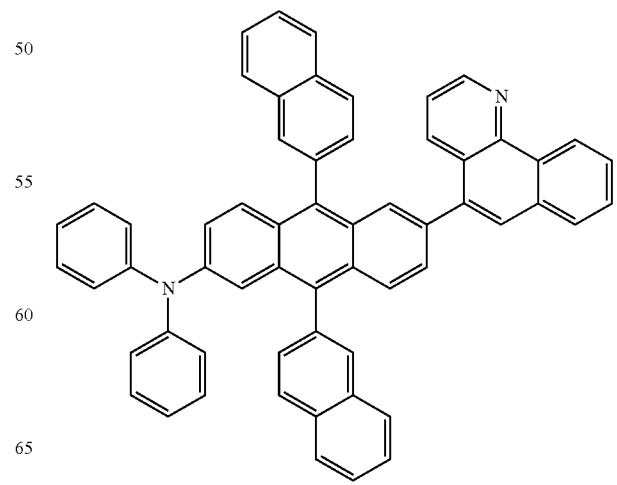

[Formula 1-78]
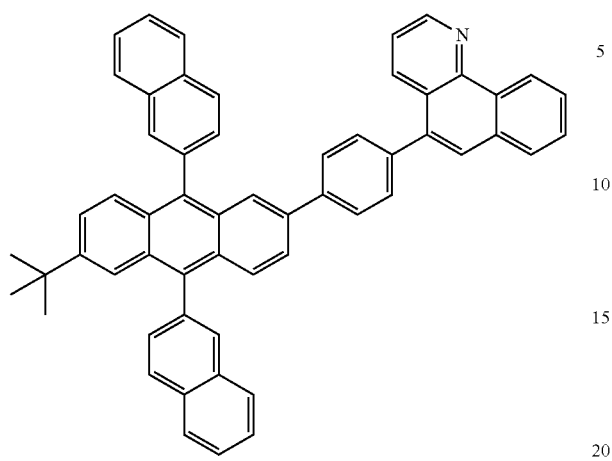
[Formula 1-79]
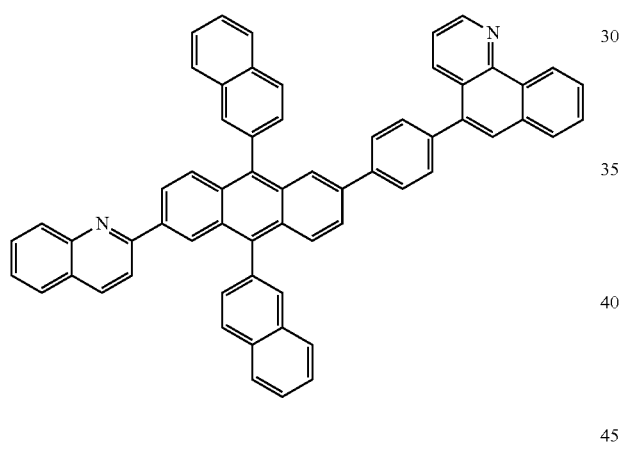
[Formula 1-80]
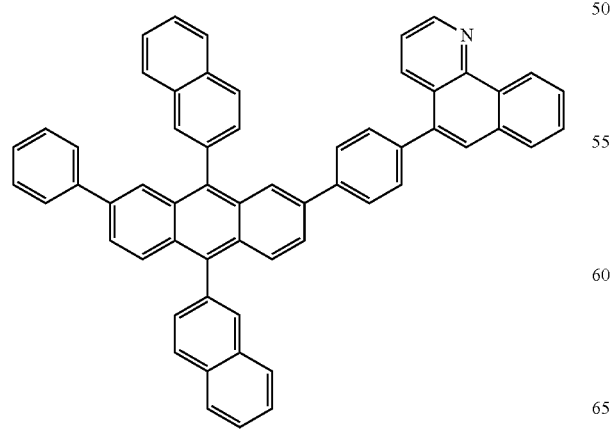
[Formula 1-81]
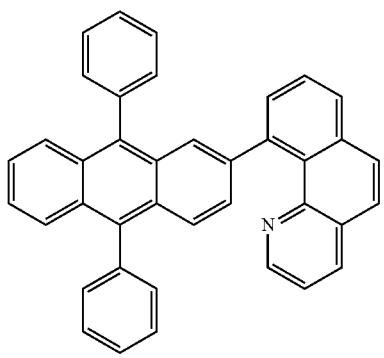
[Formula 1-82]
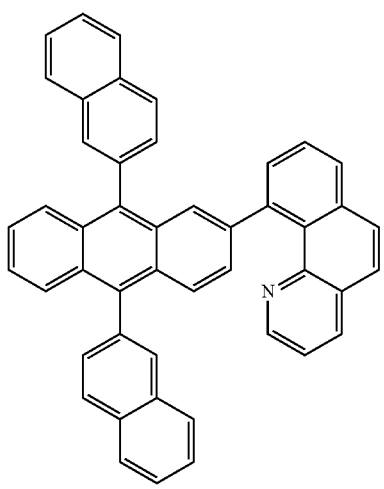
[Formula 1-83]
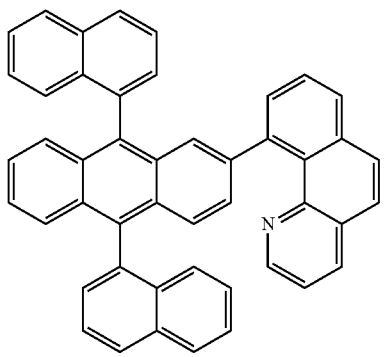

[Formula 1-84]
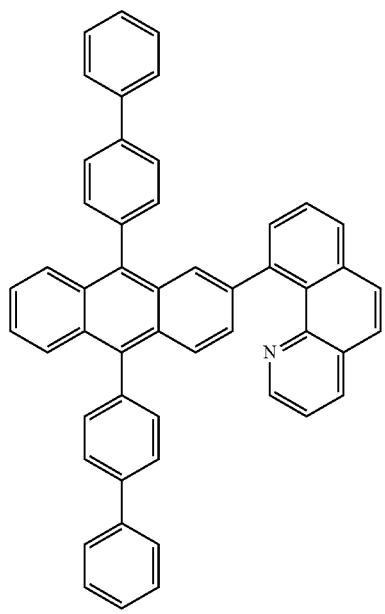
[Formula 1-85]
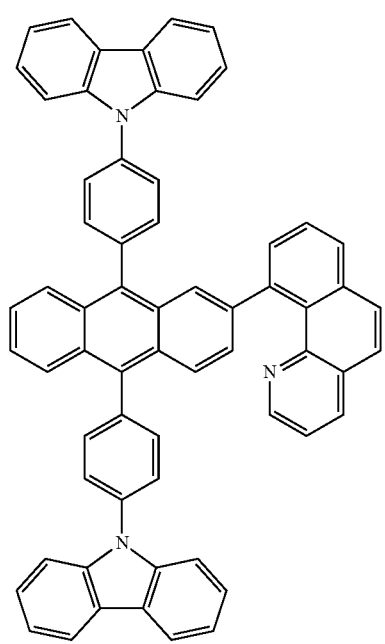
[Formula 1-86]
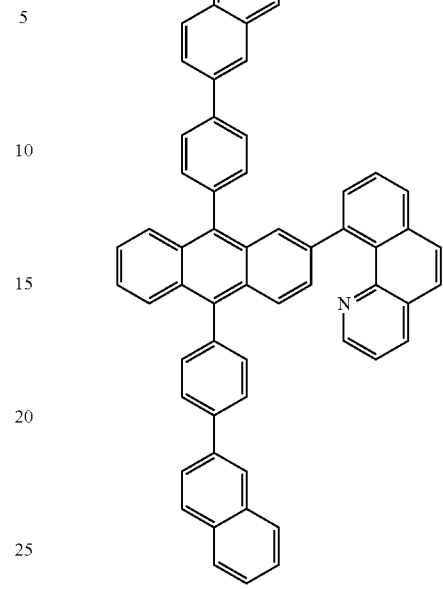
[Formula 1-87]
[Formula 1-88]
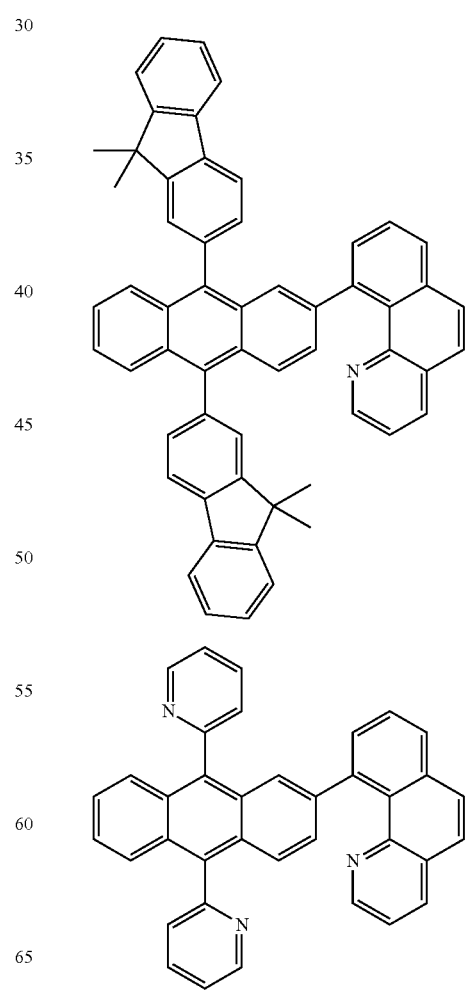

[Formula 1-89]
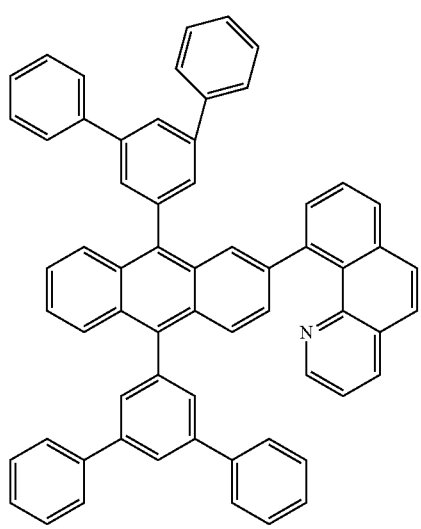
[Formula 1-90]
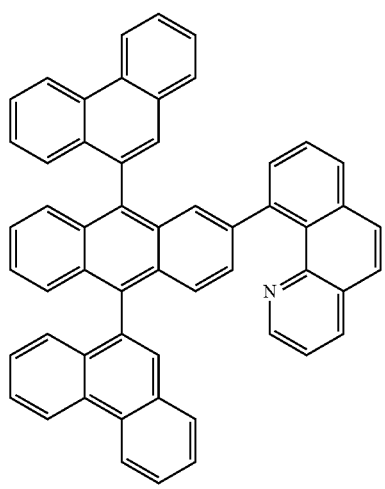
[Formula 1-91]
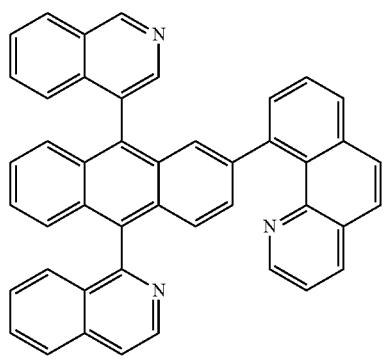
[Formula 1-92]
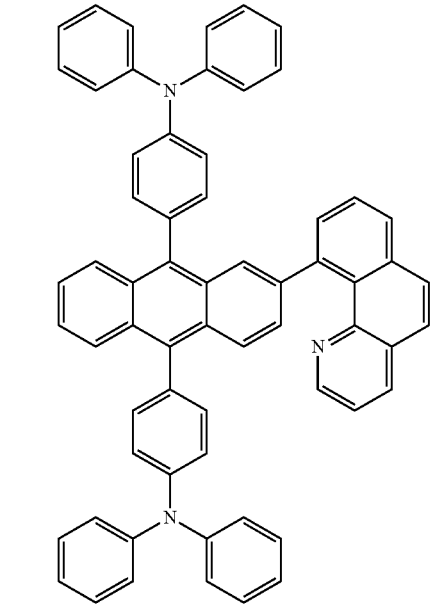
[Formula 1-93]
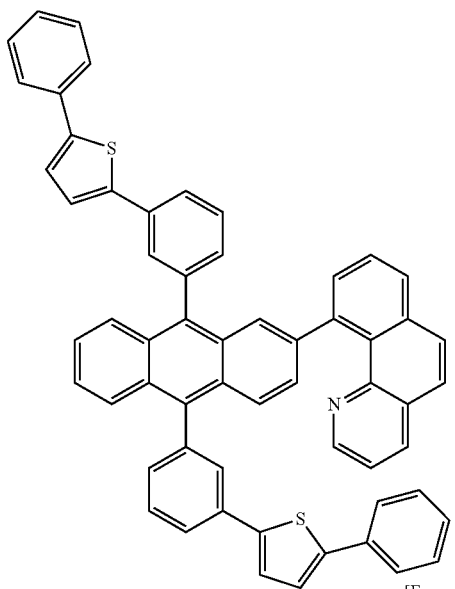
[Formula 1-94]
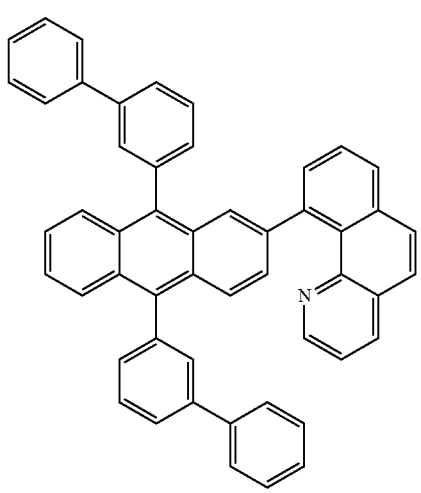

[Formula 1-95]
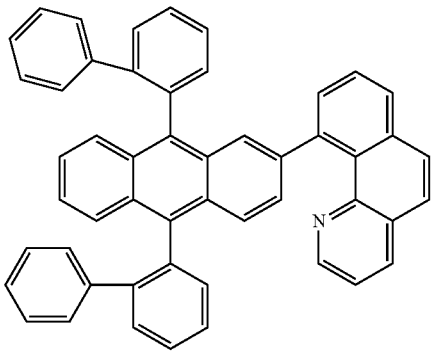
[Formula 1-96]
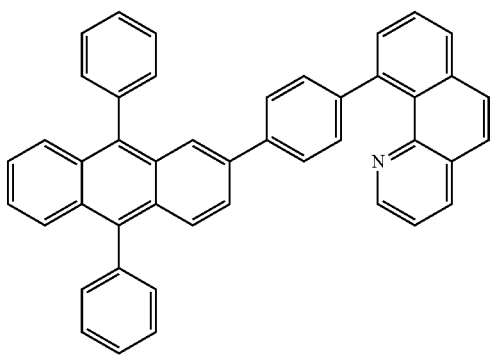
[Formula 1-97]
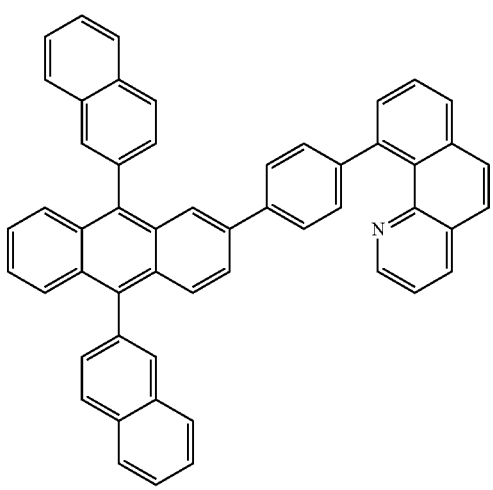
[Formula 1-98]
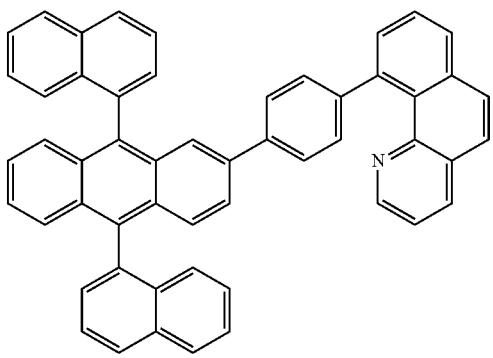
[Formula 1-99]
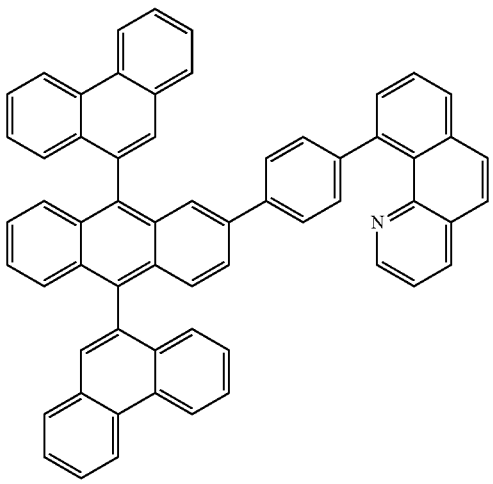
[Formula 1-100]
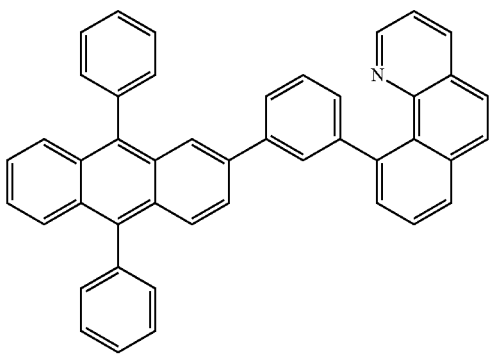
[Formula 1-101]
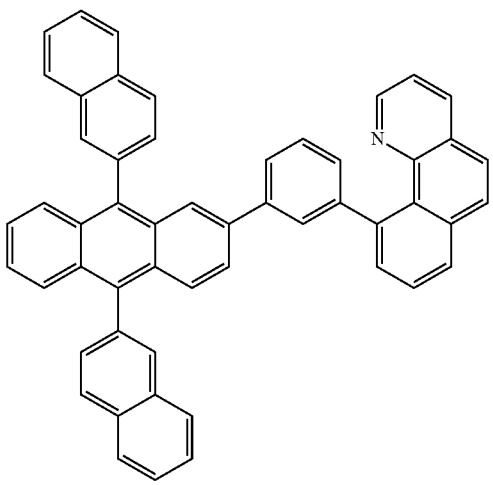

[Formula 1-102]
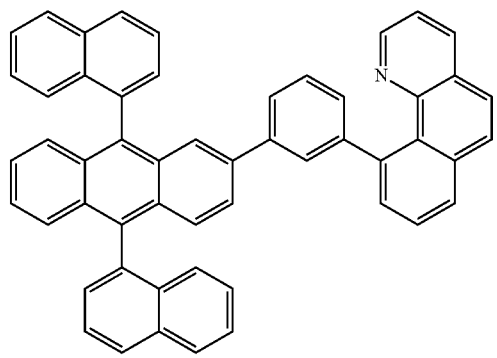
[Formula 1-105]
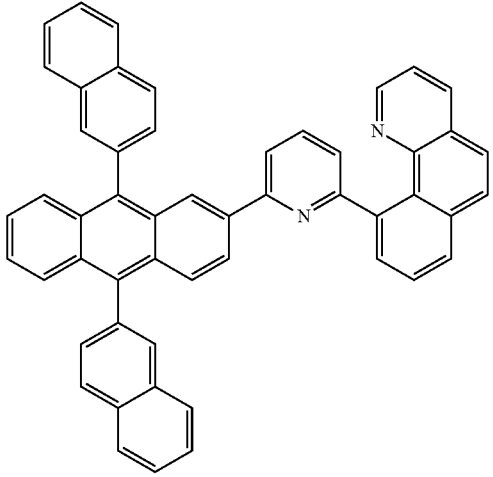
[Formula 1-103]
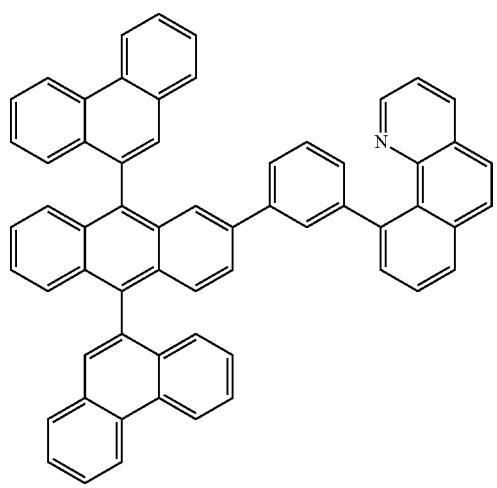
[Formula 1-106]
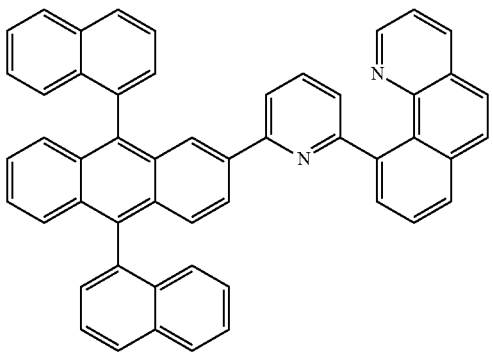
[Formula 1-104]
[Formula 1-107]
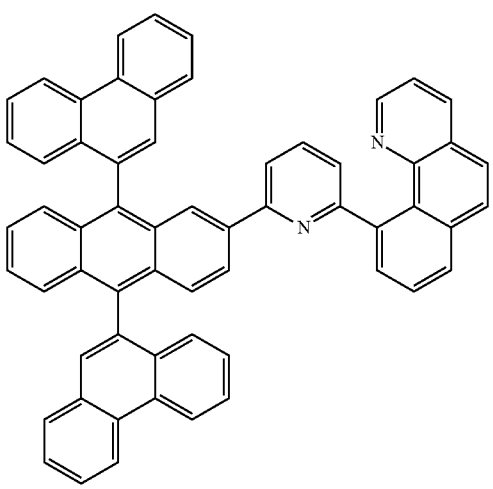

[Formula 1-108]
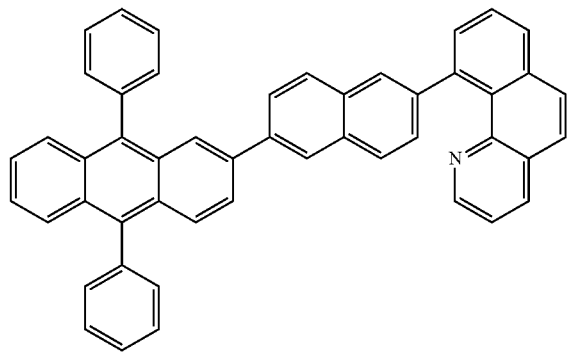
[Formula 1-109]
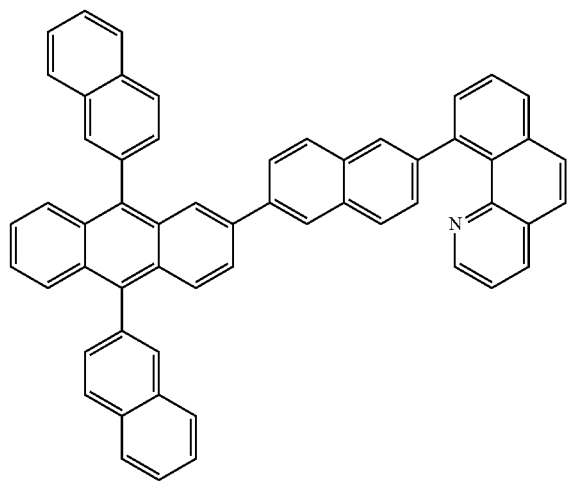
[Formula 1-110]
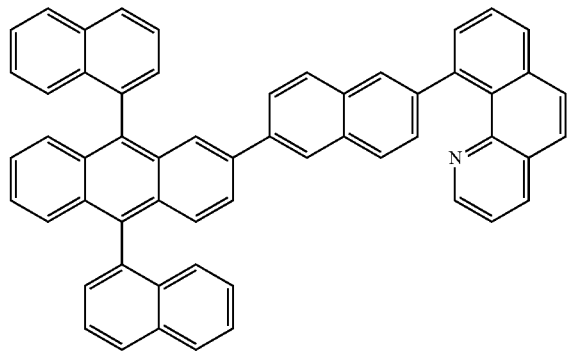
[Formula 1-111]
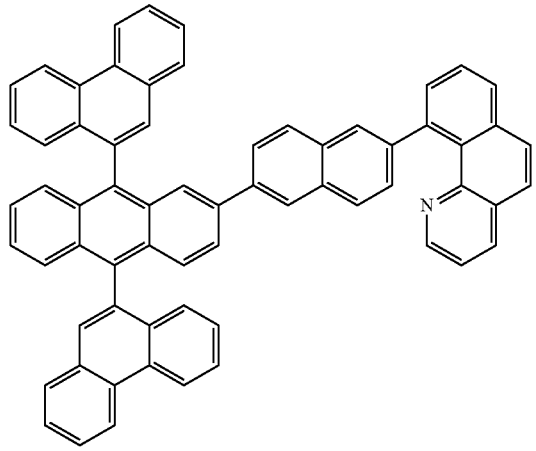
[Formula 1-112]
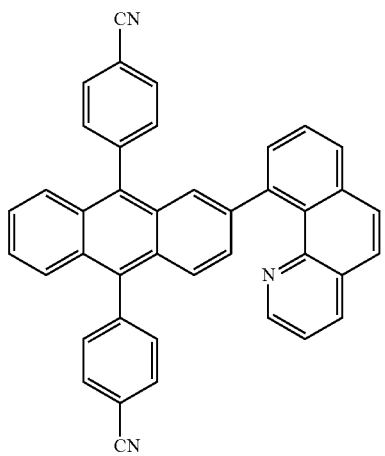
[Formula 1-113]
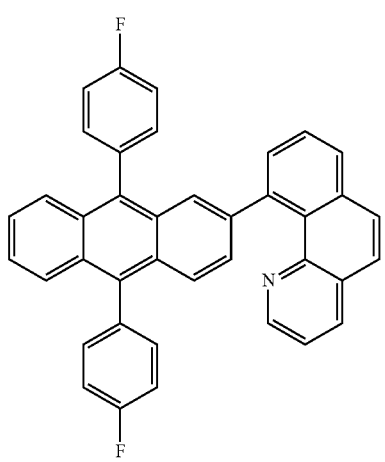

[Formula 1-114]
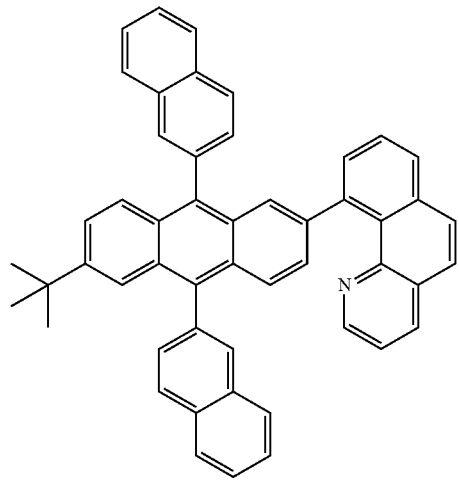
[Formula 1-115]
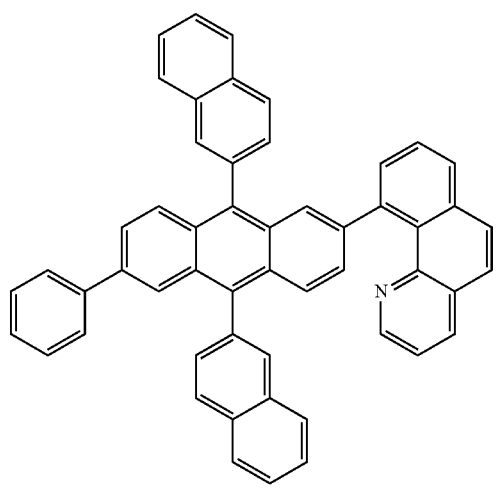
[Formula 1-116]
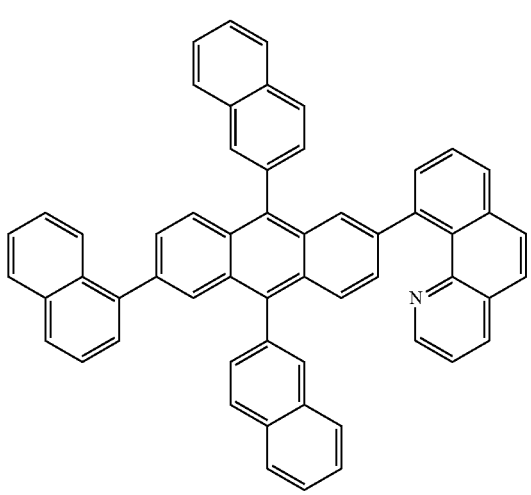
[Formula 1-117]
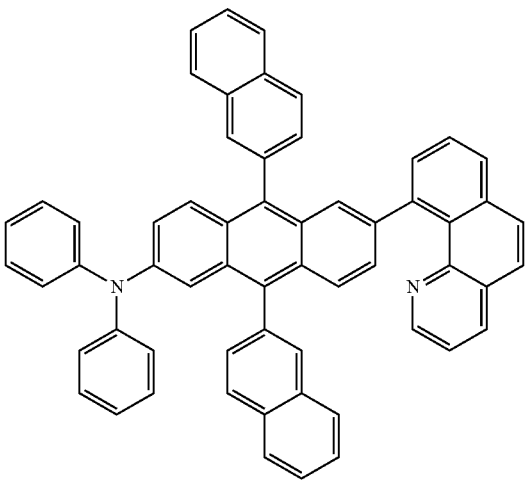
[Formula 1-118]
[Formula 1-119]
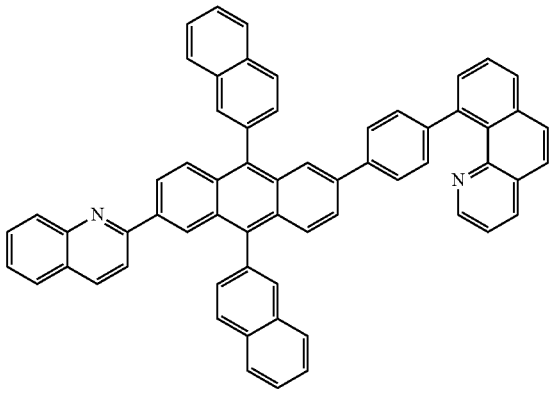

[Formula 1-120]
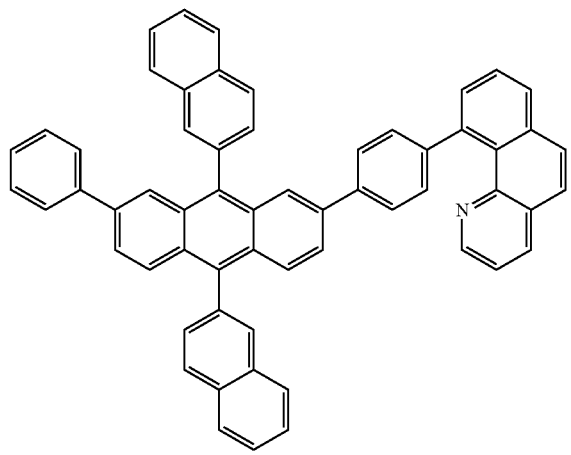
In addition, as preferable detailed examples of the compound of Formula 1, there are the compounds of the following Formulas 2-1 to 2-40, but it is not limited thereto.
[Formula 2-1]
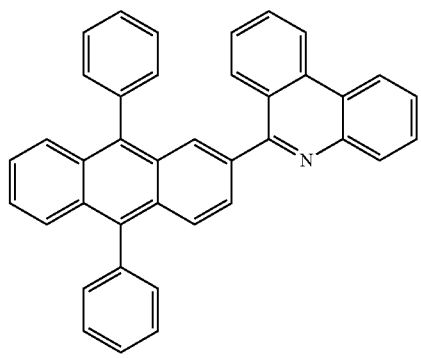
[Formula 2-2]
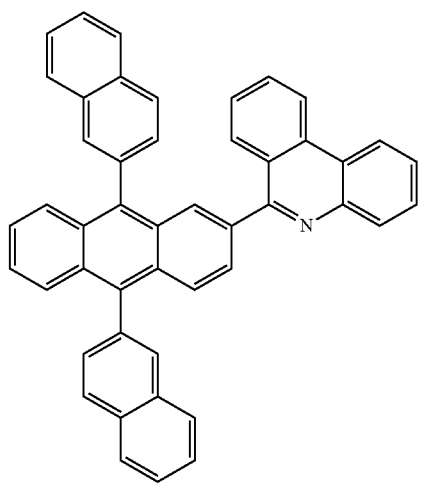
[Formula 2-3]
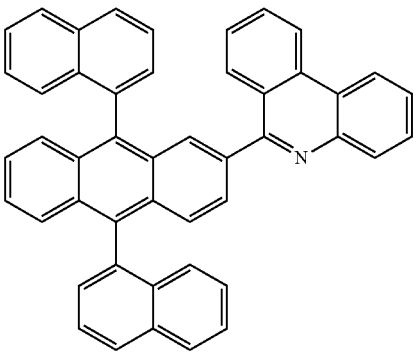
[Formula 2-4]
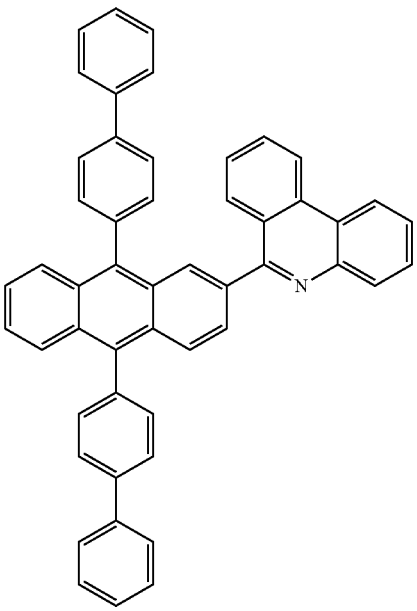
[Formula 2-5]
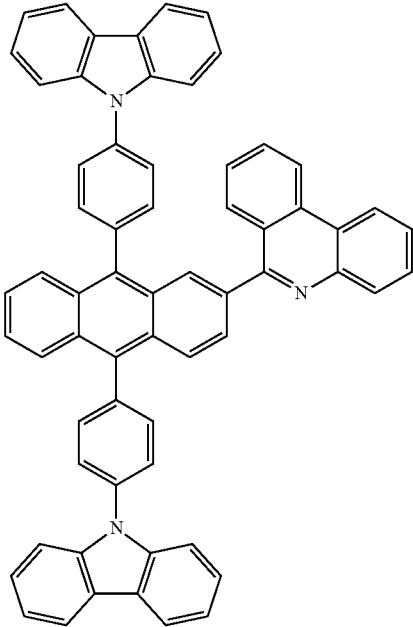

[Formula 2-6]
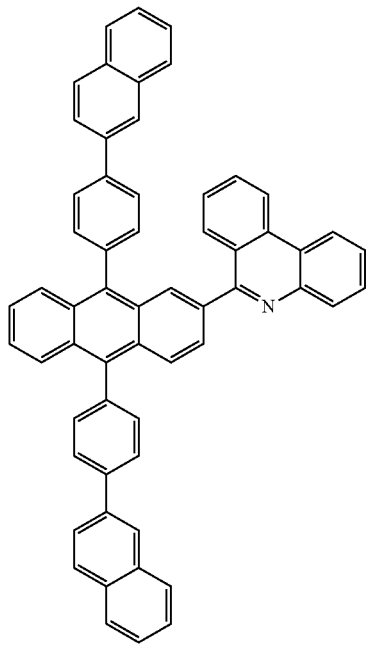
[Formula 2-7]
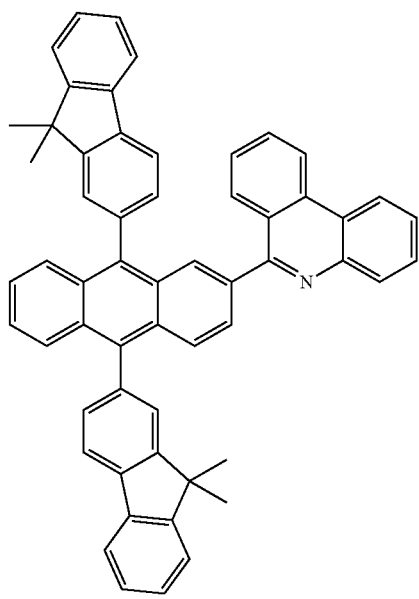
[Formula 2-8]
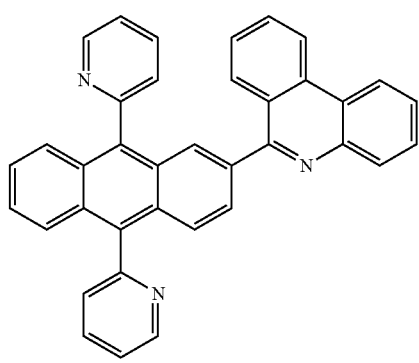
[Formula 2-9]
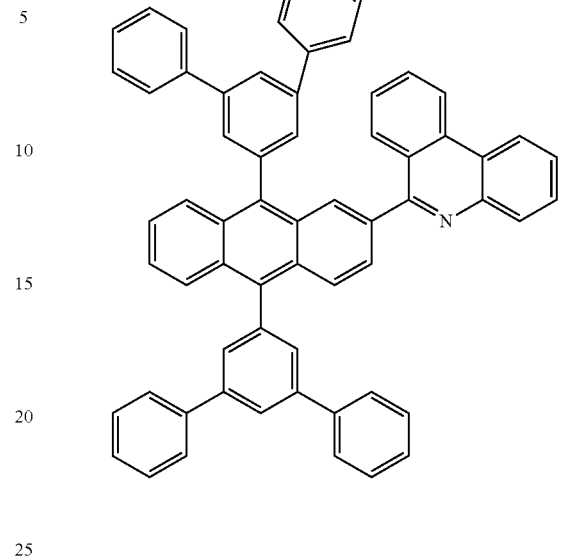
[Formula 2-10]
[Formula 2-11]

[Formula 2-12]
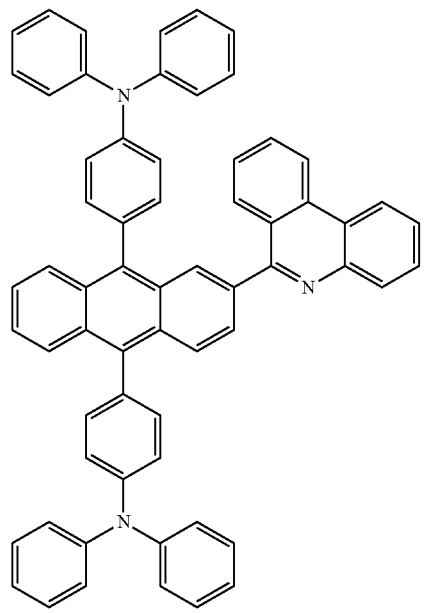
[Formula 2-13]
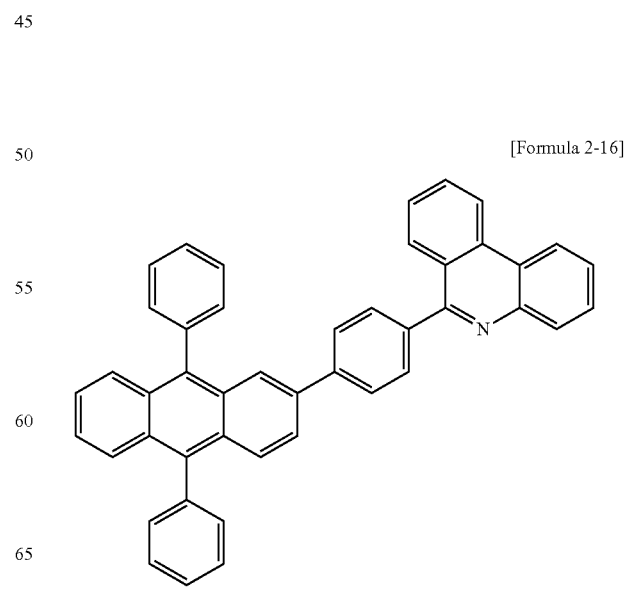
[Formula 2-14]
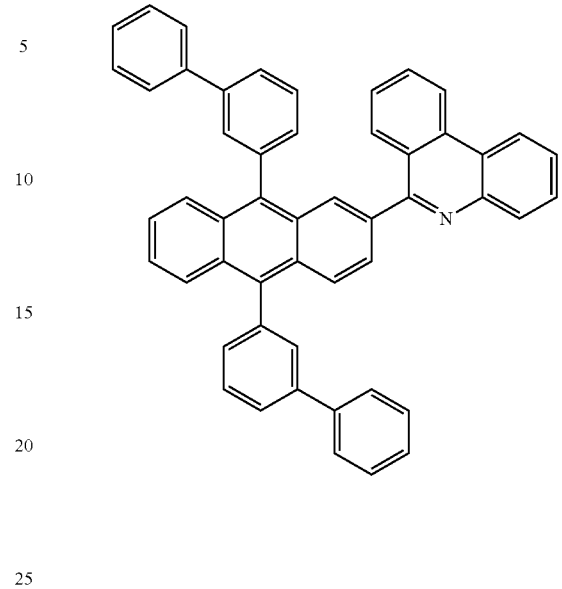
[Formula 2-15]
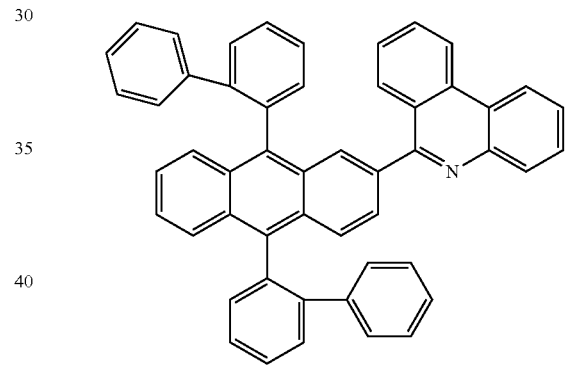
[Formula 2-16]

[Formula 2-17]
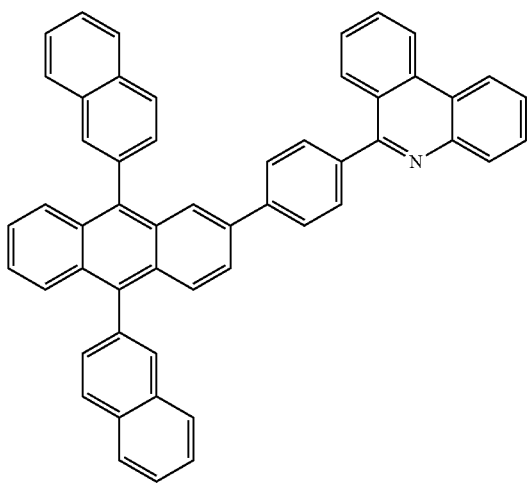
[Formula 2-18]
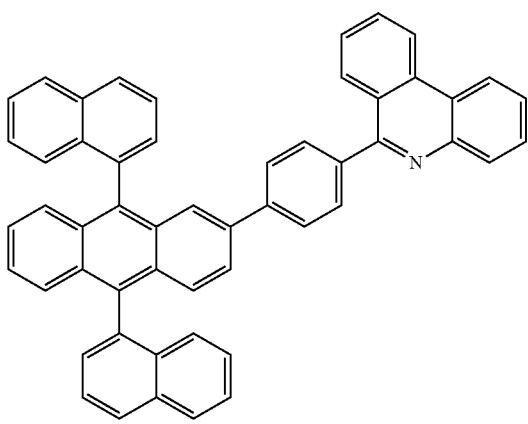
[Formula 2-19]
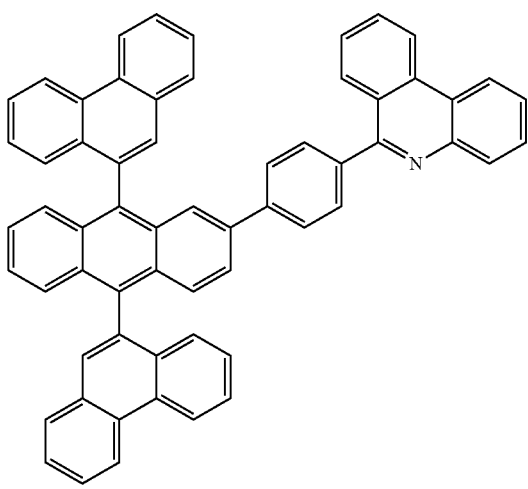
[Formula 2-20]
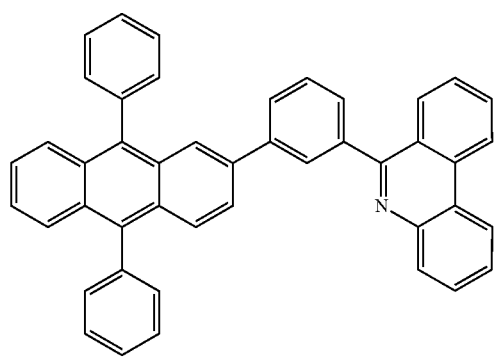
[Formula 2-21]
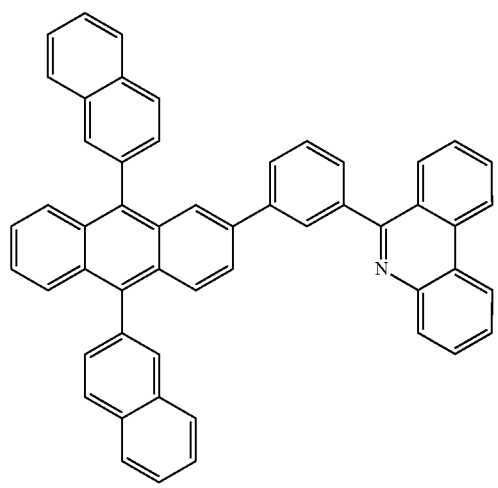
[Formula 2-22]
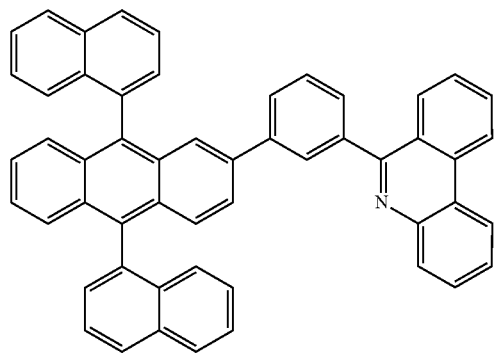

[Formula 2-23]
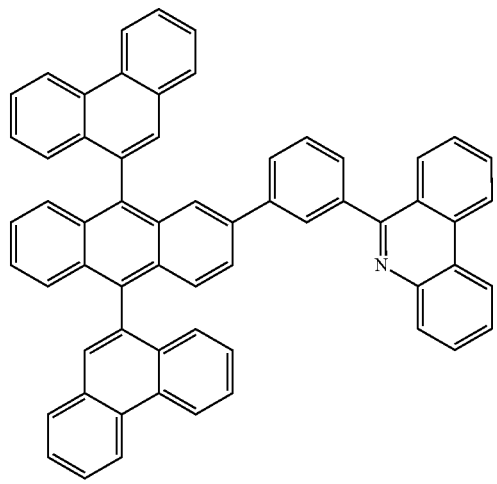
[Formula 2-24]
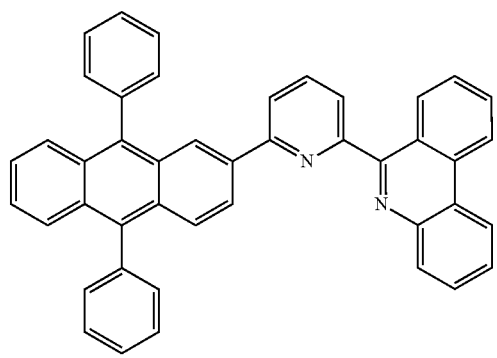
[Formula 2-25]
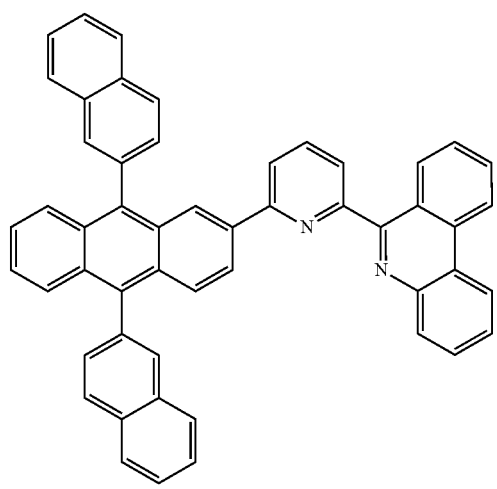
[Formula 2-26]
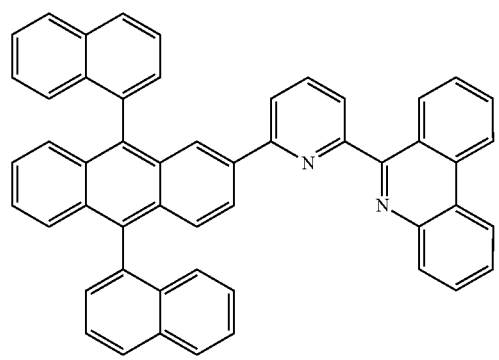
[Formula 2-27]
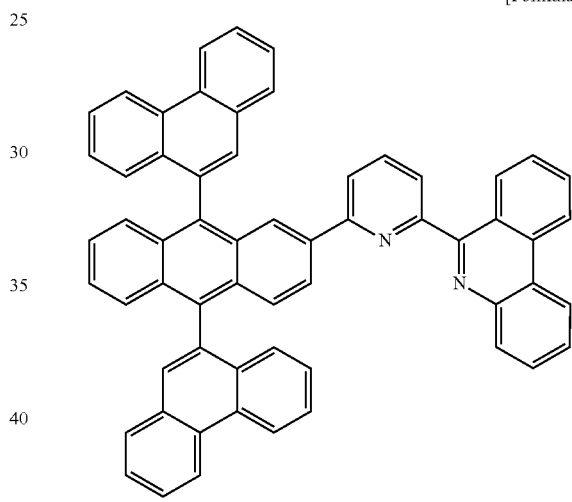
[Formula 2-28]
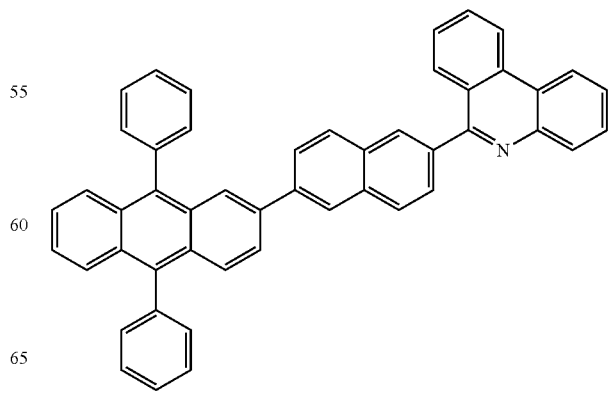

[Formula 2-29]
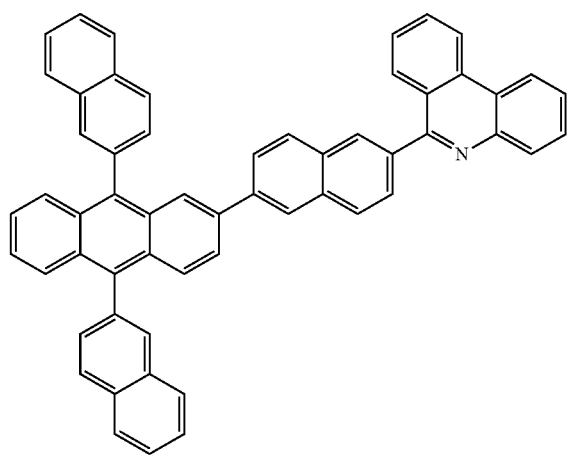
[Formula 2-32]
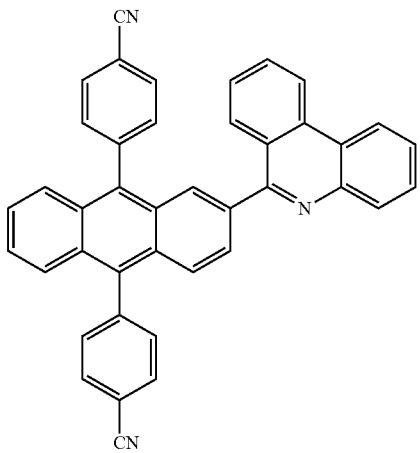
[Formula 2-30]
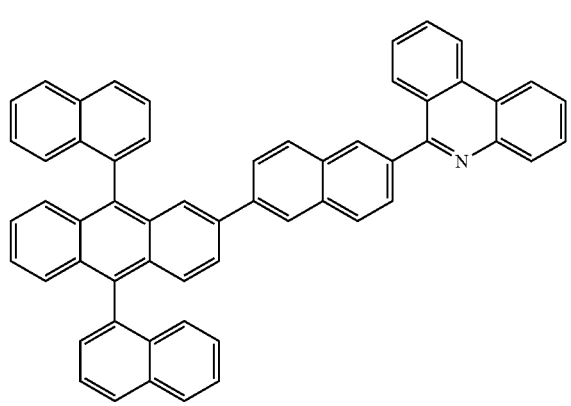
[Formula 2-33]
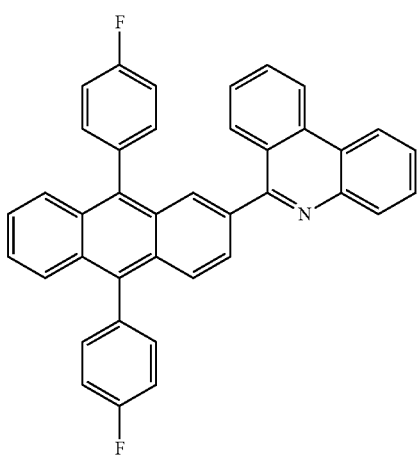
[Formula 2-31]
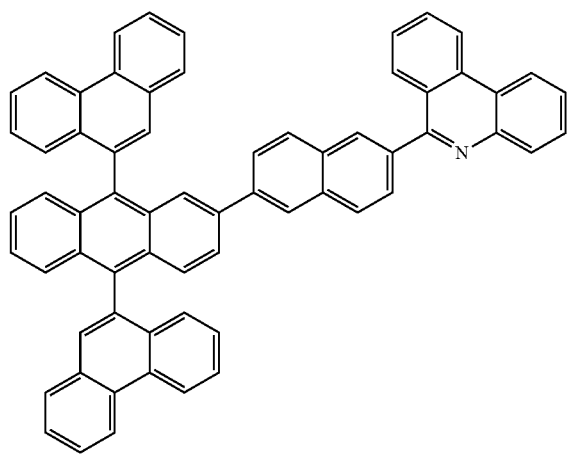
[Formula 2-34]
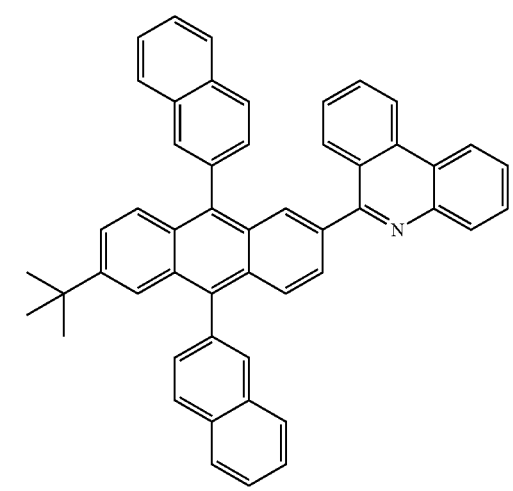

[Formula 2-35]
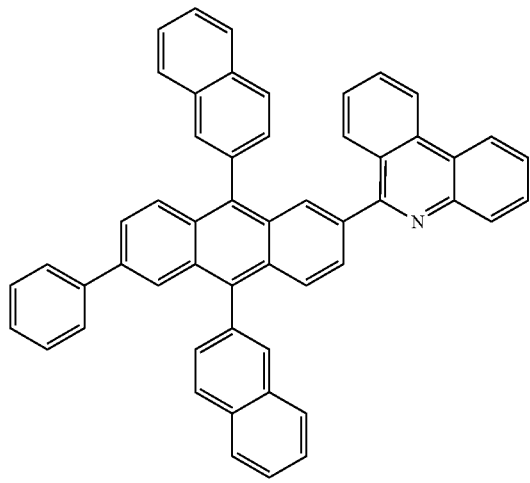
[Formula 2-36]
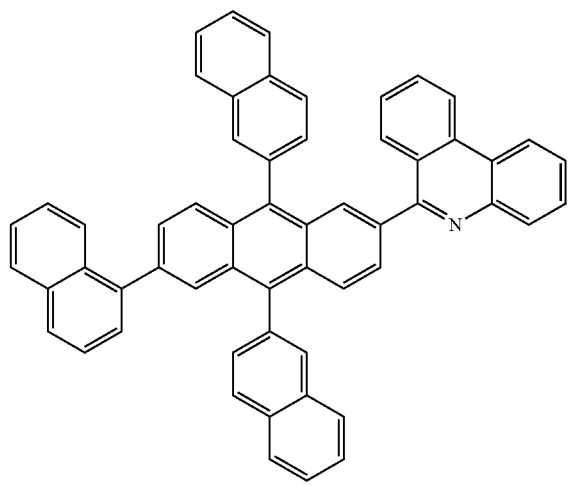
[Formula 2-37]
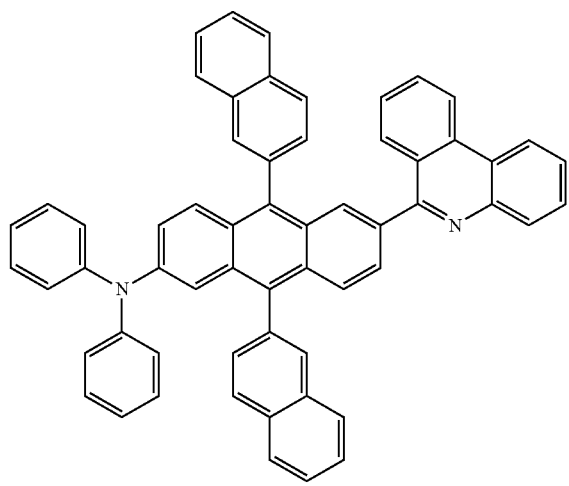
[Formula 2-38]
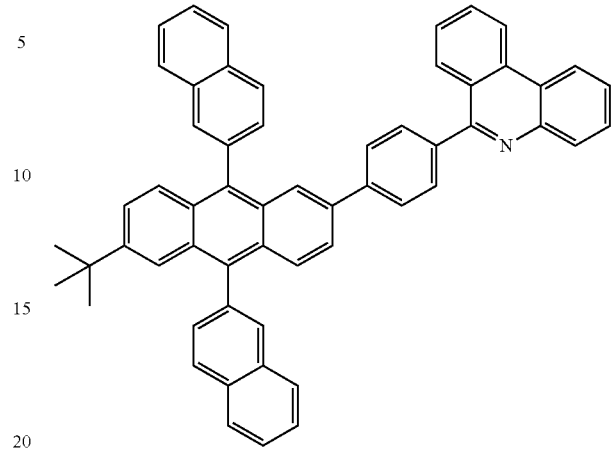
[Formula 2-39]
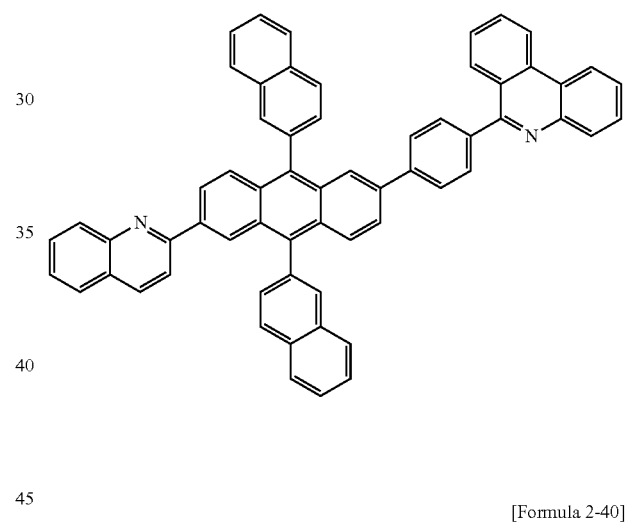
[Formula 2-40]
In addition, as preferable detailed examples of the compound of Formula 1, there are the compounds of the following Formulas 3-1 to 3-40, but it is not limited thereto.

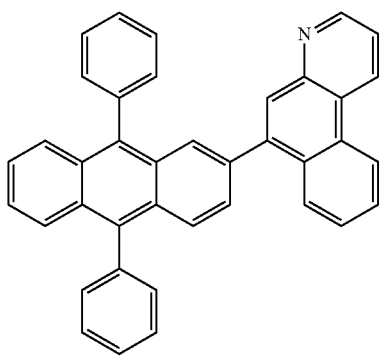
[Formula 3-1]
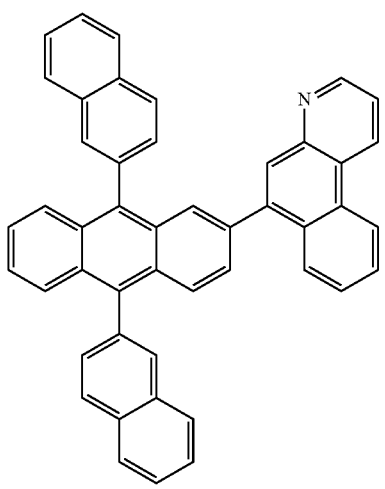
[Formula 3-2]
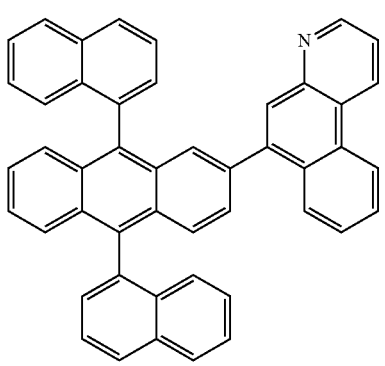
[Formula 3-3]
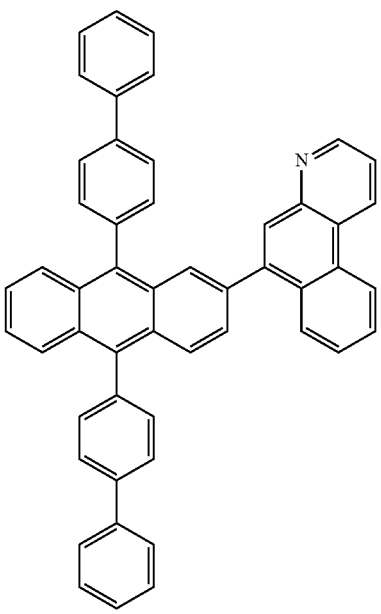
[Formula 3-4]
[Formula 3-5]

[Formula 3-6]
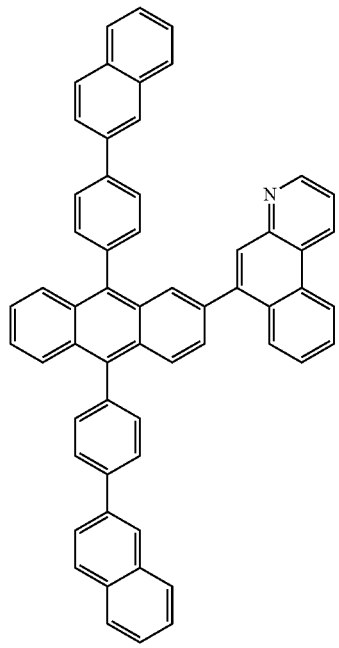
[Formula 3-7]
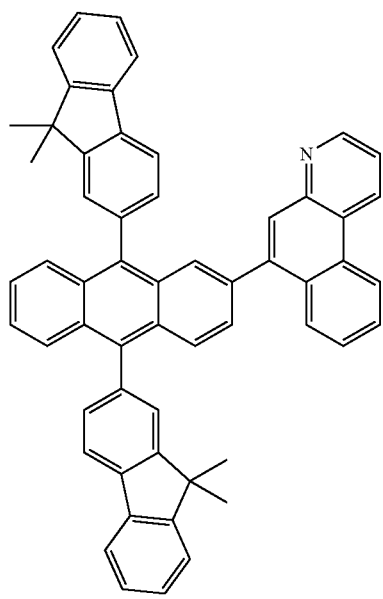
[Formula 3-8]
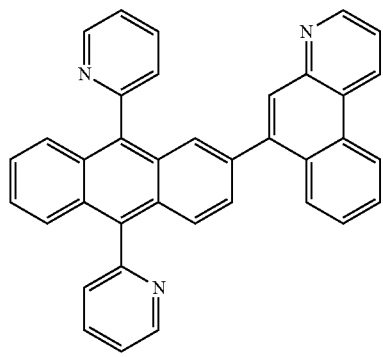
[Formula 3-9]
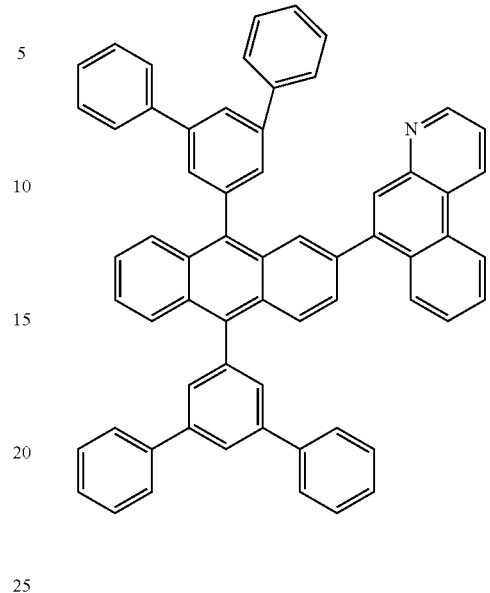
[Formula 3-10]
[Formula 3-11]
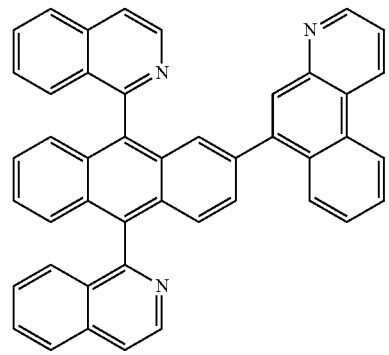

[Formula 3-12]
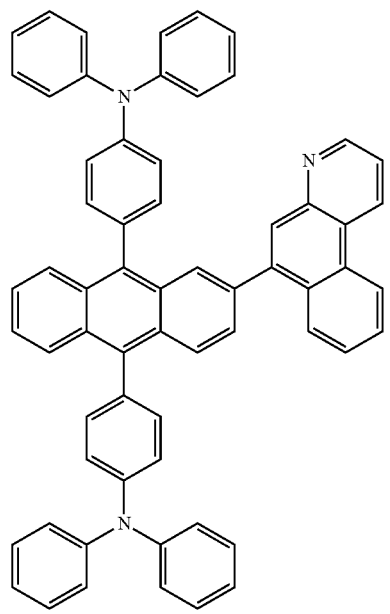
[Formula 3-13]
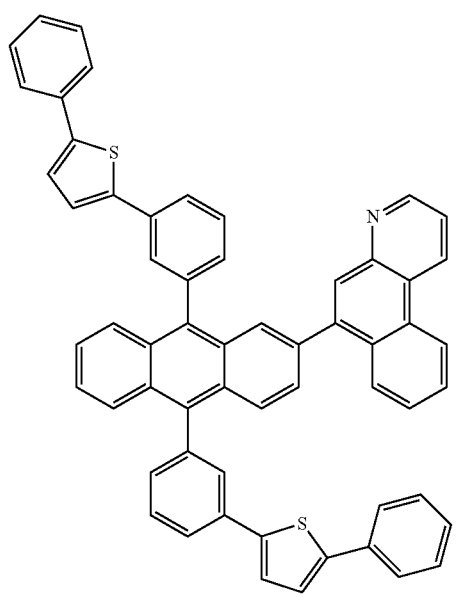
[Formula 3-14]
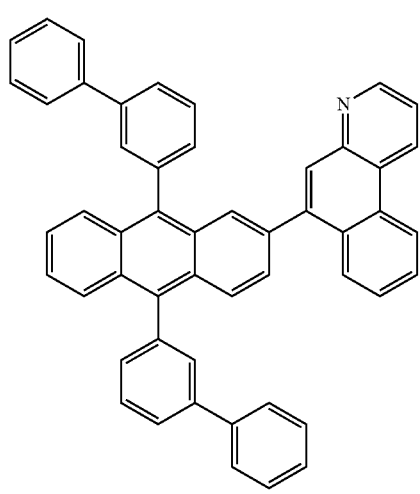
[Formula 3-15]
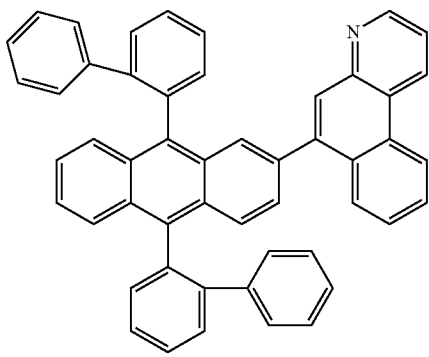
[Formula 3-16]
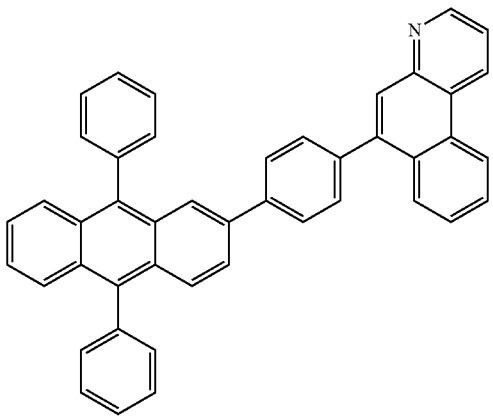
[Formula 3-17]
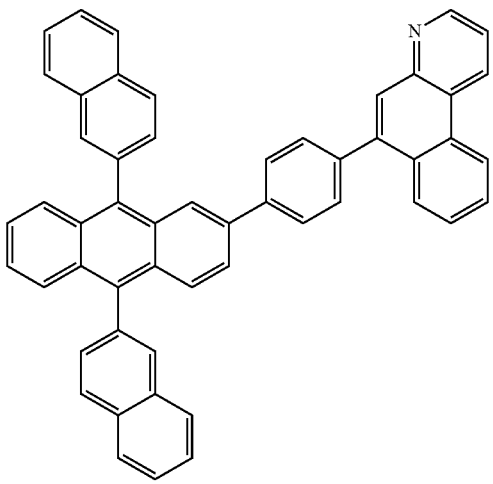

-continued
[Formula 3-18]
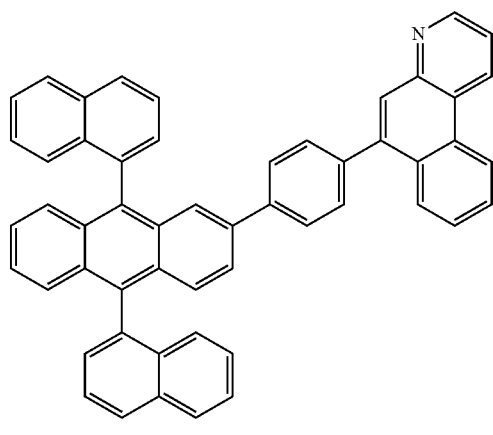
[Formula 3-19]
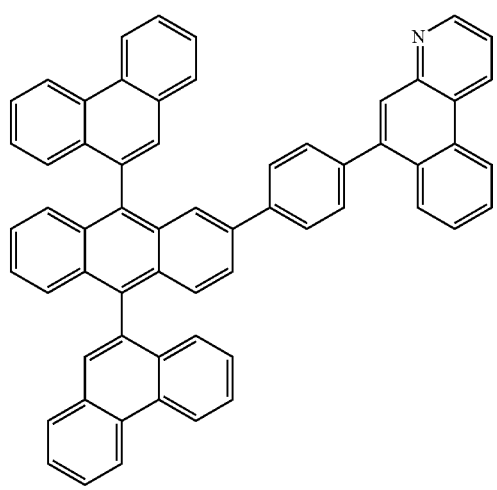
[Formula 3-20]
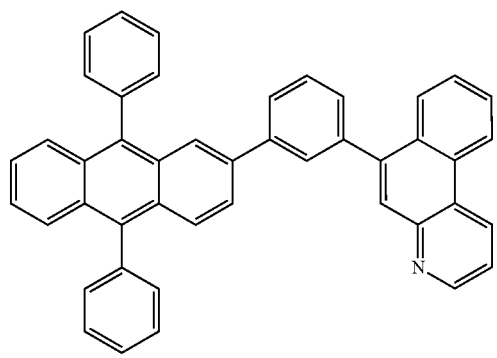
-continued
[Formula 3-21]
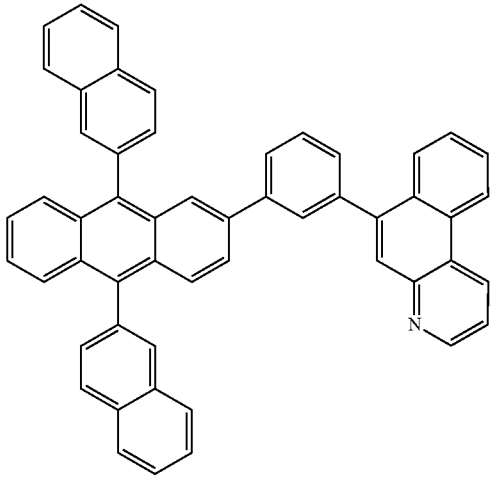
[Formula 3-22]
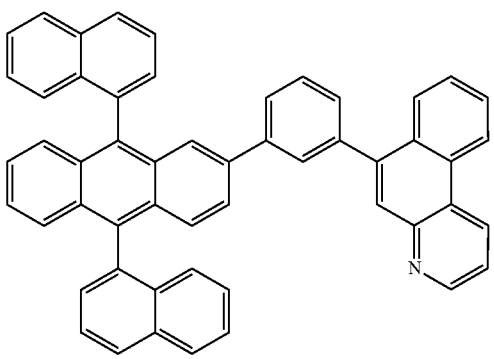
[Formula 3-23]
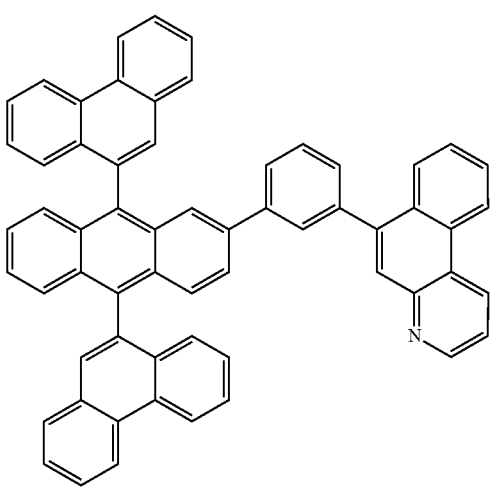

[Formula 3-24]
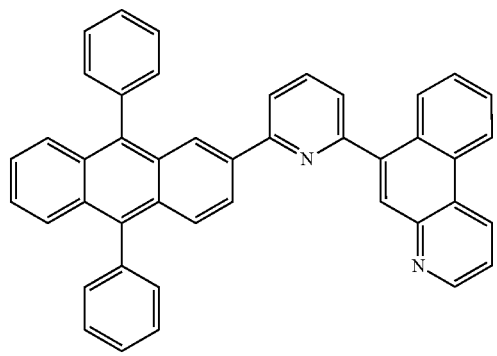
[Formula 3-25]
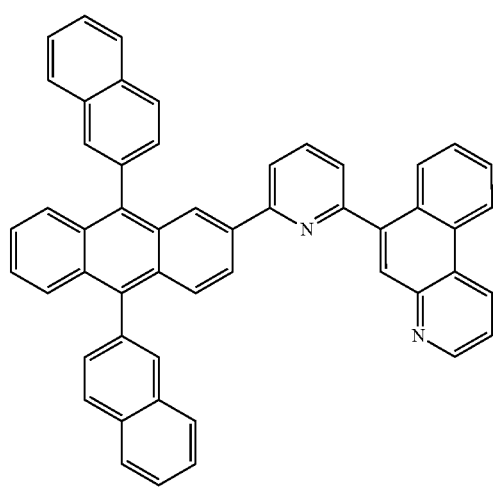
[Formula 3-26]
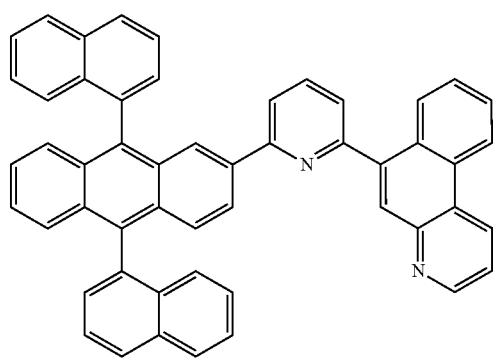
[Formula 3-27]
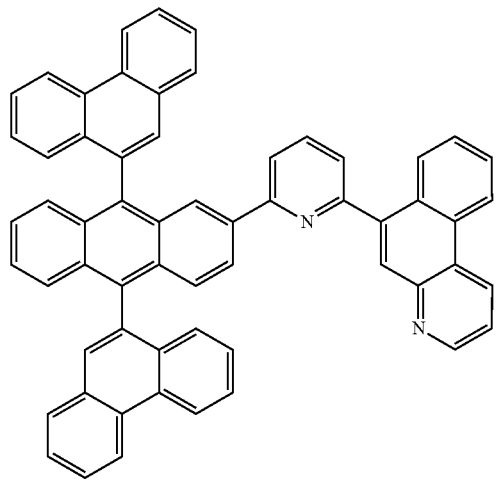
[Formula 3-28]
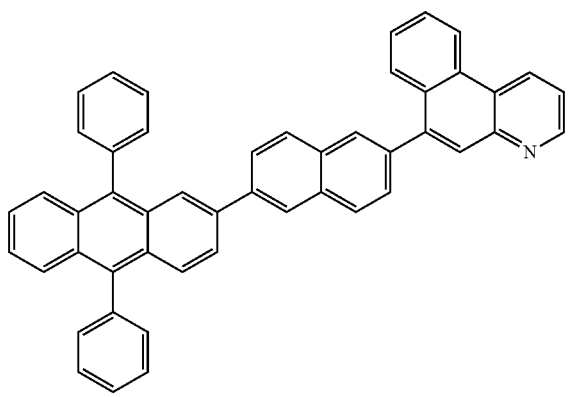
[Formula 3-29]
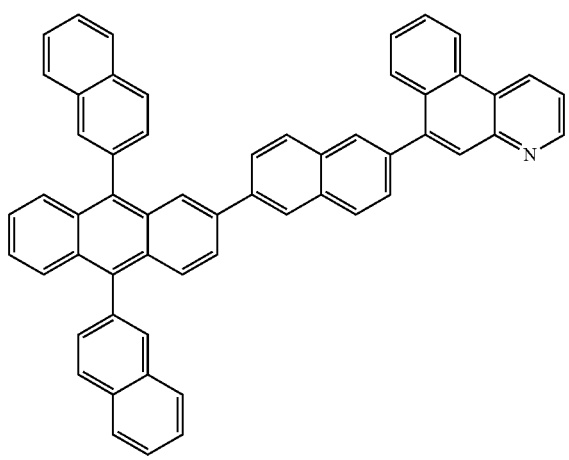

[Formula 3-30]
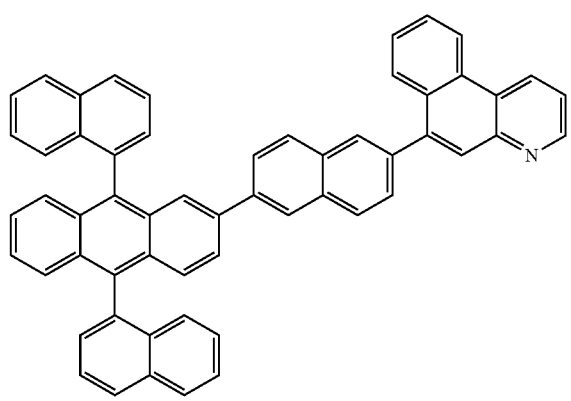
[Formula 3-31]
[Formula 3-32]
[Formula 3-33]
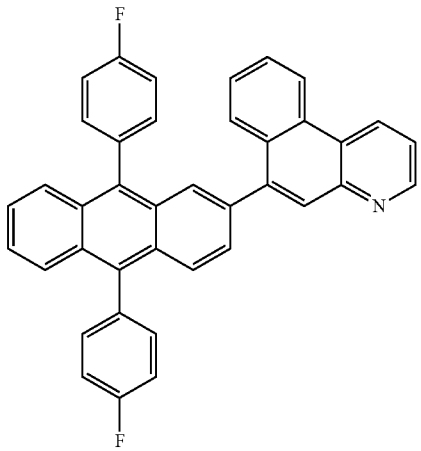
[Formula 3-34]
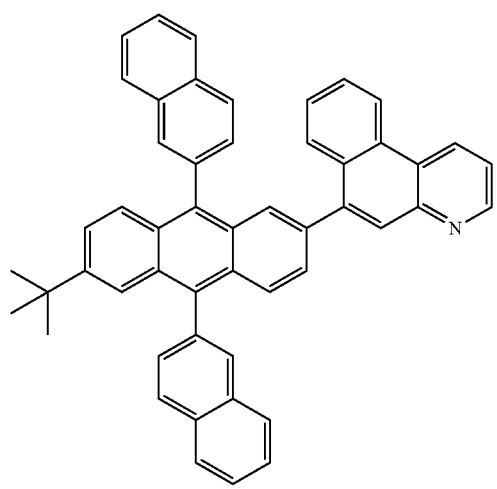
[Formula 3-35]
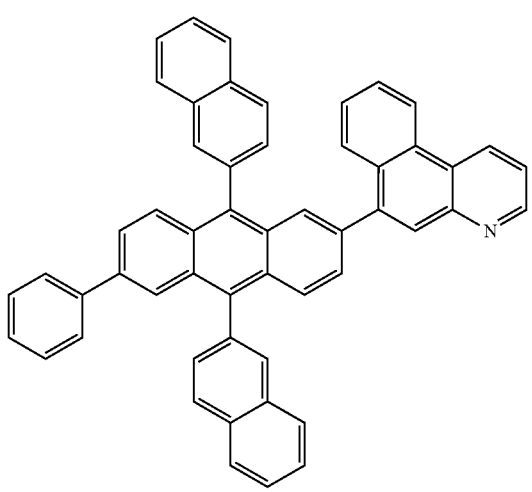

[Formula 3-36]

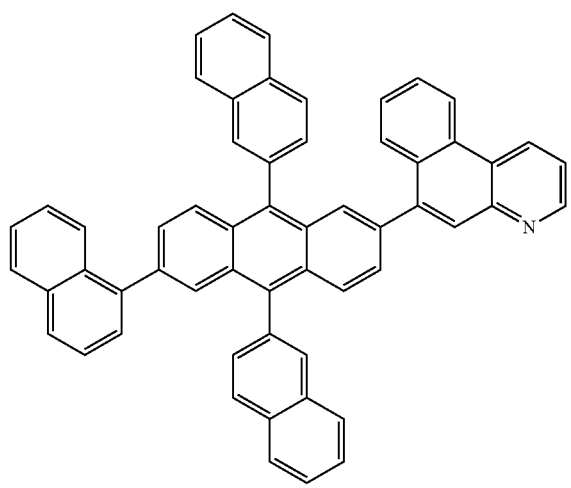

[Formula 3-37]

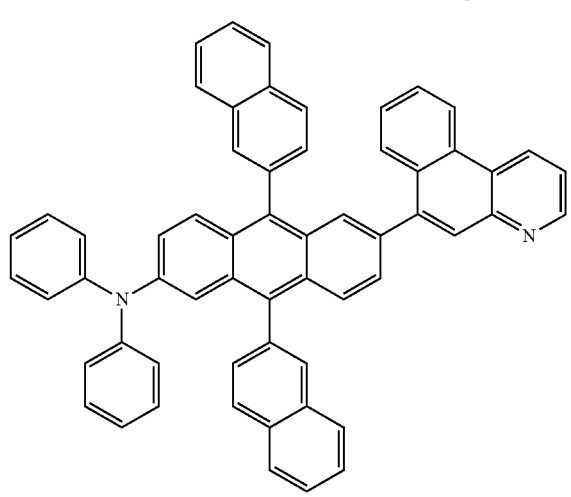

[Formula 3-38]

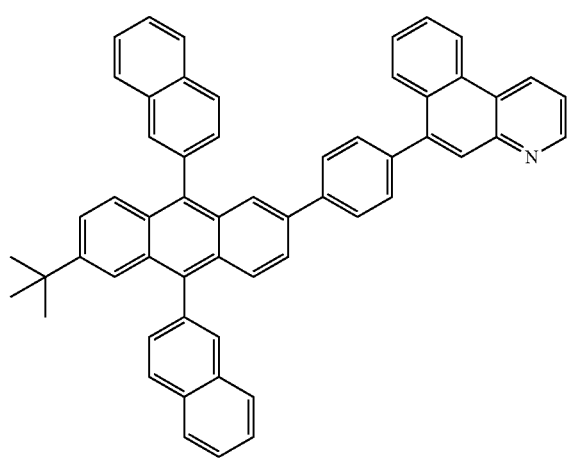

[Formula 3-39]

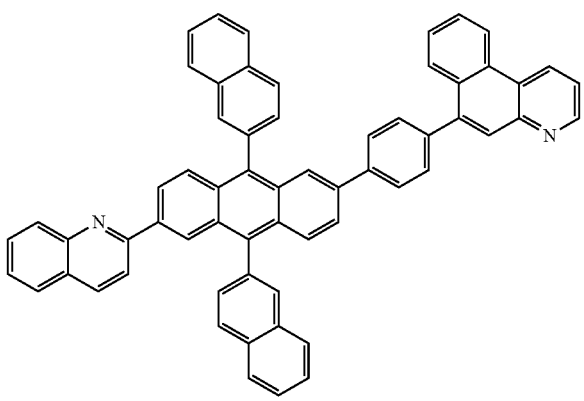

[Formula 3-40]

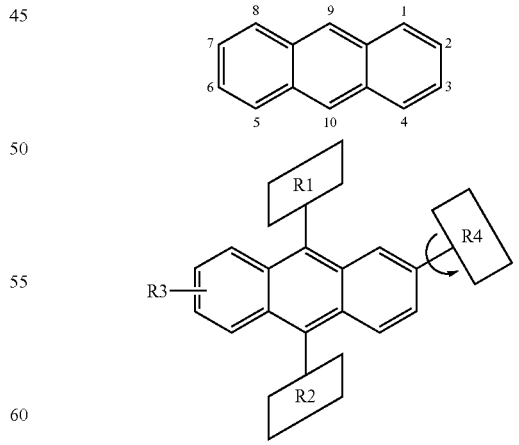

The steric structure of the compound of Formula 1 according to the present invention may be the following Formula. R1 and R2 at 9, 10 positions of anthracene form a large dihedral angle because of the steric hindrance. This shows an effect that suppresses formation of excited excimer or excited exciplex that may be included in a flat structure like anthracene.

R4 that is introduced at 2 position of anthracene, which has relatively small steric hindrance as compared to 9, 10 positions of anthracene, forms a small R4 is the substituent group that includes a benzoquinoline having an ability of electron transport and injection, and may increase the electron transport ability through conjugation with anthracene. In addition, anthracene that has relatively small steric hindrance and R4 have structural flexibility, improves an interfacial property with a cathode, and has a structure that is capable of advantageously being used in views of electron injection ability and device life span. Accordingly, efficiency of the device, a driving voltage, and a life span are improved by applying the compound having the above structure to the organic electronic device.

Hereinafter, a method for manufacturing the compound of Formula 1 will be described.

According to an embodiment of the present invention, the compound of Formula 1 may be manufactured by using a method that includes the steps of:

1) manufacturing an anthraquinone derivative that is substituted by R4 by Suzuki coupling the anthraquinone derivative that is substituted by the halogen group and the boronic acid or boron ester compound having the R4 substituent body under the Pd catalyst.

2) manufacturing a dialcohol derivative from the anthraquinone derivative manufactured in the step 1), and 3) manufacturing the anthracene derivative by reducing the dialcohol derivative manufactured in the step 2). The manufacturing method may be represented by the following Reaction Equation 1.

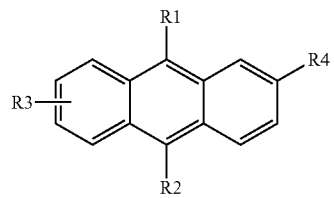

In Reaction Equation, R1 to R4 are the same as those defined by Formula 1. According to an embodiment of the present invention, the compound of Formula 1 may be manufactured by using a method that includes the steps of:

1) manufacturing a dialcohol derivative from the anthraquinone derivative that is substituted by the halogen group, 2) manufacturing an anthracene derivative by reducing a dialcohol derivative manufactured in the step 1), 3) manufacturing the anthracene derivative manufactured in the step 2) to a anthracene boron ester derivative or an anthracene boronic acid derivative, and 4) manufacturing the compound of Formula 1 that is substituted by R4 by Suzuki coupling the anthracene boron ester derivative or an anthracene boronic acid derivative manufactured in the step 3) and halogenates of R4 or R4-O—SO$_2$—CF$_3$ under the Pd catalyst. The manufacturing method may be represented by the following Reaction Equation 2.

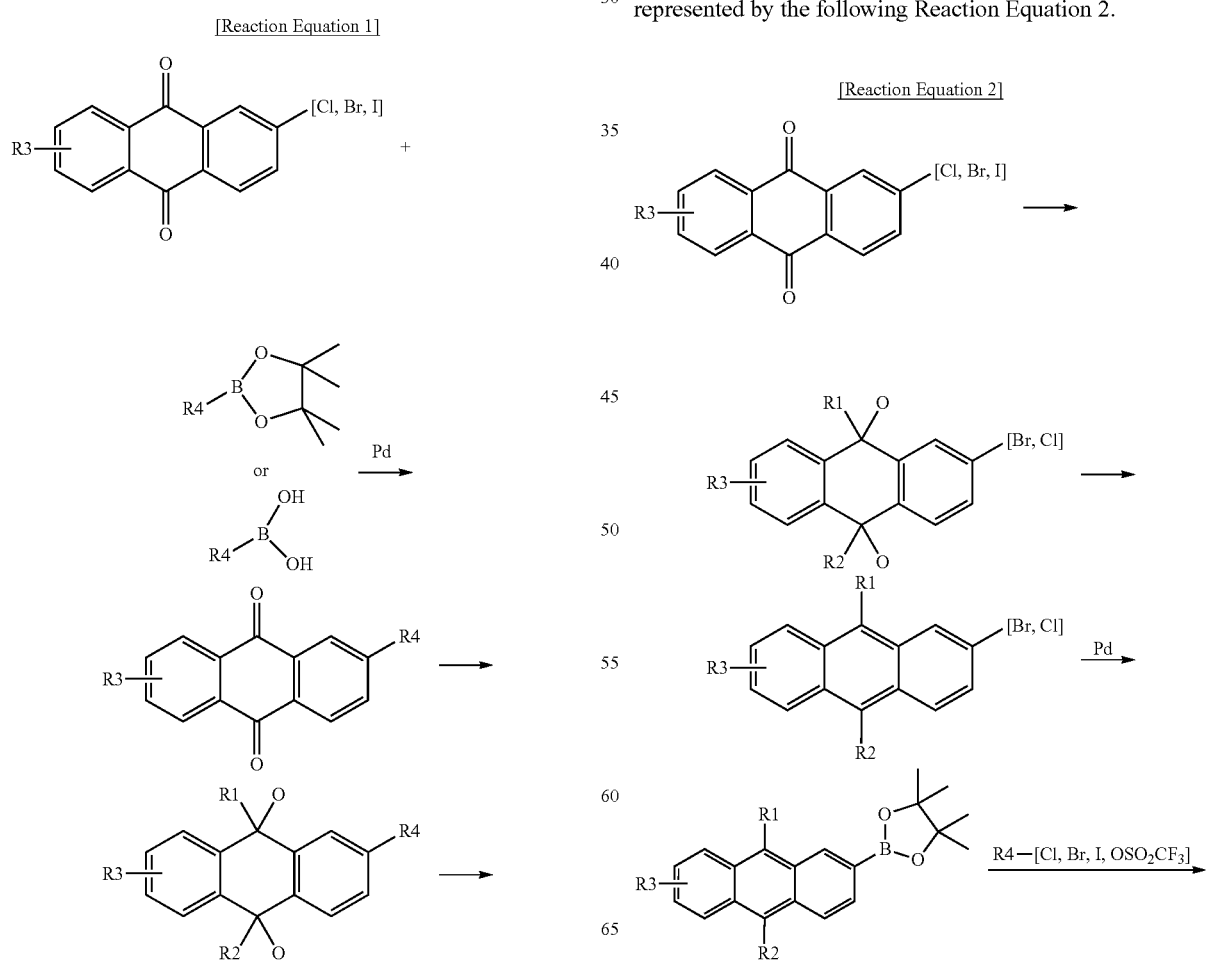

-continued

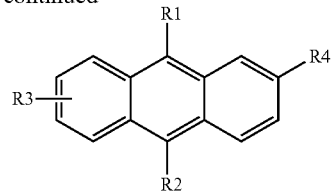

In Reaction Equation, R1 to R4 are the same as those defined by Formula 1.

Among the methods used in the manufacturing of the compound of Formula 1, reactions that are not the Suzuki reaction may use a general method known in the art.

In addition, the present invention provides an organic electronic device which comprises a first electrode, a second electrode, and at least one organic material layer that is disposed between the first electrode and the second electrode, wherein at least one layer of the organic material layer comprises the compound of Formula 1.

The organic electronic device according to the present invention may be manufactured by using a manufacturing method and a material of a general organic electronic device, except that one or more organic material layers are formed by using the above compounds.

Hereinafter, the organic light emitting device will be described.

In an embodiment of the present invention, the organic light emitting device may have a structure that includes a first electrode, a second electrode, and an organic material layer that is disposed between them. The organic material layer of the organic light emitting device according to the present invention may have a single layer structure including one layer and a multilayered structure that includes two or more layers including a light emitting layer. In the case of when the organic material layer of the organic light emitting device according to the present invention has the multilayered structure, for example, this may be a structure in which hole injection layer, hole transport layer, light emitting layer, electron transport layer and the like are layered. However, the structure of the organic light emitting device is not limited to this, but may comprise a smaller number of organic material layers. For example, the organic light emitting device according to the present invention may have the same structure as the structure shown in FIG. 1. In FIG. 1, reference numeral 1 represents a substrate, reference numeral 2 represents an anode, reference numeral 3 represents a hole injection layer, reference numeral 4 represents a hole transport layer, reference numeral 5 represents an organic light emitting layer, reference numeral 6 represents an electron transport layer, and reference numeral 7 represents a cathode. The organic light emitting device having the structure that is same as that of FIG. 1 is referred to as an organic light emitting device having a positive direction structure, but the present invention is not limited thereto and includes an organic light emitting device having an inversion direction structure. That is, the organic light emitting device may have a structure in which a substrate, a cathode, an electron transport layer, an organic light emitting layer, a hole transport layer, a hole injection layer and an anode are sequentially layered.

In the case of when the organic light emitting device according to the present invention includes an organic material layer having a multilayered structure, the compound of Formula 1 may be included in a light emitting layer, hole transport layer, a layer that performs simultaneously hole transport and light emission, a layer that performs simultaneously light emission and electron transport, an electron transport layer, an electron transport and/or injection layer. In the present invention, it is preferable that the compound of Formula 1 is included in the electron injection and/or transport layer or the light emitting layer.

In particular, in the case of when the compound of Formula 1 according to the present invention is included in the electron transport layer, the electron transport layer may include alkali metal, an alkali metal compound, alkali earth metal, an alkali earth metal compound or a combination thereof.

The organic light emitting device according to the present invention may be manufactured by using a manufacturing method and a material of a general organic electronic device, except that the compound of Formula 1 is used in one or more layers of the organic material layer of the organic light emitting device. For example, the organic light emitting device according to the present invention may be manufactured by forming an anode by depositing metal or metal oxides having the conductivity or an alloy thereof on a substrate by using a PVD (physical vapor deposition) method such as sputtering or e-beam evaporation, forming the organic material layer that includes hole injection layer, hole transport layer, light emitting layer and electron transport layer thereon, and depositing the material that is capable of being used as a cathode thereon. In addition to the above method, in order to manufacture the organic light emitting device having the inversion direction structure, the organic light emitting device may be manufactured by sequentially depositing a cathode material, an organic material layer, and an anode material on a substrate.

The organic material layer may be manufactured in a smaller number of layer by using various polymer materials and by using not a deposition method but a solvent process, for example, spin coating, dip coating, doctor blading, screen printing, inkjet printing, heat transferring method and the like.

As the anode material, in general, it is preferable to use the material having the large work function so as to smoothly perform hole injection into the organic material layer. As examples of the anode material that is capable of being used in the present invention, there are metal or alloy thereof such as vanadium, chrome, copper, zinc, gold and the like; metal oxides such as zinc oxides, indium oxides, indium tin oxides (ITO), indium zinc oxides (IZO) and the like; a combination of metal and oxides such as ZnO:Al or $SnO_2$:Sb; conductive polymers such as poly(3-methylthiophene), poly[3,4-(ethylene-1,2-dioxy)thiophene](PEDOT), polypyrole and polyaniline, but it is not limited thereto.

As the cathode material, in general, it is preferable to use the material having the small work function so as to smoothly perform electron injection into the organic material layer. As detailed examples of the cathode material, there are metal such as magnesium, calcium, sodium, potassium, titanium, indium, yttrium, lithium, gadolinium, aluminium, silver, tin, and lead or an alloy thereof; a multilayered structure material such as LiF/Al or $LiO_2$/Al, but it is not limited thereto.

The hole injection material is a material that is capable of well receiving holes from the anode at a low voltage, and it is preferable that the HOMO (highest occupied molecular orbital) of the hole injection material is a value between the work function of the anode material and the HOMO of the organic material layer around them. As detailed examples of the hole injection material, there are metal porphyrine, oligothiophene, arylamine-based organic material, hexanitrilehexaazatriphenylene-based organic material, quinacridone-based organic material, perylene-based organic material, anthraquinone and polyaniline and polythiophene-based conductive polymers, but it is not limited thereto.

The hole transport material is a material that receives the holes from the anode or the hole injection layer and transfer them to the light emitting layer, and it is preferable to use the material having the large mobility to the holes. As detailed examples thereof, there are arylamine-based organic material, a conductive polymer, and a block copolymer in which a conjugate portion and a non-conjugate portion are simultaneously included, but it is not limited thereto.

The light emitting material is a material that receives the holes and the electrons from the hole transport layer and the electron transport layer, combines them, such that light at a range of visible rays is emitted, and it is preferable to use the material having excellent photon efficiency to fluorescence or phosphorescence. As detailed examples thereof, there are a 8-hydroxy-quinoline aluminium complex ($Alq_3$); a carbazole-based compound; a dimerized styryl compound; a bis-methyl-8-hydroxyquinoline paraphenylphenol aluminium complex (Balq); a 10-hydroxybenzo quinoline-metal compound; a benzoxazole, benzthiazole and benzimidazole-based compound; a poly(p-phenylenevinylene) (PPV)-based polymer; a spiro compound; polyfluorene, lubrene and the like, but it is not limited thereto.

The electron transport material is a material that receives the electrons from the cathode and transfers them to the light emitting layer, and it is preferable to use the material having the large mobility to the electrons. As detailed examples thereof, there are a 8-hydroxyquinoline Al complex; a complex including $Alq_3$; an organic radical compound; a hydroxyflavone metal complex and the like, but it is not limited thereto.

The organic light emitting device according to the present invention may be a front side light emitting type, a rear side light emitting type, or a both sides light emitting type according to the used material.

The novel anthracene derivative according to the present invention may be operated in a principle that is similar to a principle applied to the organic light emitting device in organic solar cell, organic photoconductor, organic transistor, and organic electronic device.

MODE FOR INVENTION

Hereinafter, preferable embodiment will be described in order to help understanding of the present invention. However, the following Examples are set forth to illustrate the present invention, but the scope of the present invention is not limited thereto.

Preparation Example 1

Synthesis of the Compound of the Following Formula 1-A

[Formula 1-A]

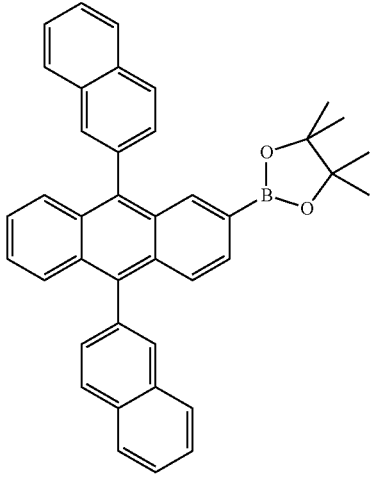

2-bromo-9,10-di(2-naphthyl)anthracene (5.00 g, 9.82 mmol), bis(pinacolato)diboron (2.75 g, 10.9 mmol) and potassium acetate (2.89 g, 29.4 mmol) were suspended in dioxane (50 mL). To the suspension solution, palladium (diphenylphosphinopherocene) chloride (0.24 g, 3 mol %) was applied. The obtained mixture was agitated for about 6 hours at 80° C., and cooled to room temperature. The mixture was diluted with water (50 mL), and extracted with dichloromethane (3×50 mL). The organic extract material was dried over magnesium sulfate and concentrated under the vacuum. The coarse product was washed with ethanol, and dried under the vacuum to manufacture the compound of Formula 1-A (5.46 g, 92%).

MS: $[M+H]^+=557$

Preparation Example 2

Synthesis of the Compounds of the Following Formula 1-B, 1-C, and 1-D

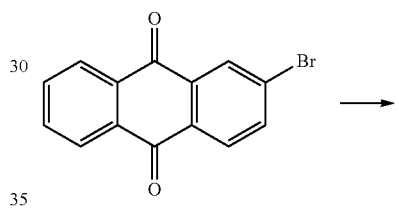

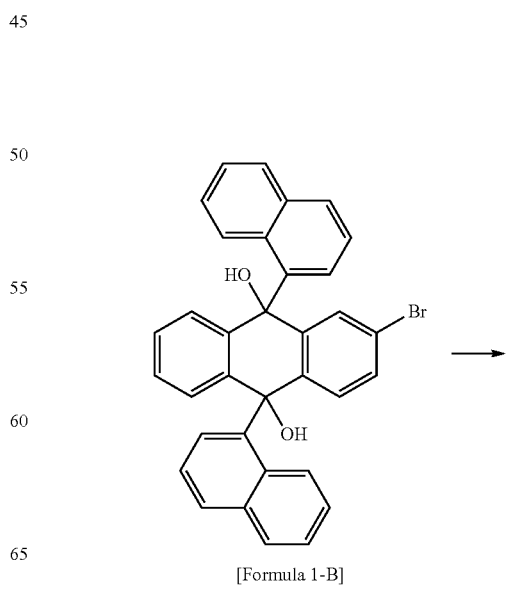

[Formula 1-B]

83

-continued

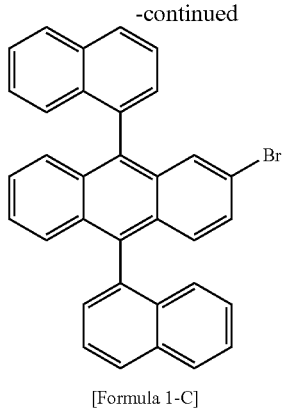

[Formula 1-C]

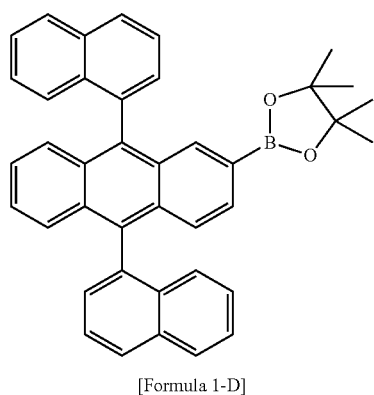

[Formula 1-D]

[Formula 1-B]

1-bromonaphthalene (34.8 g, 168.2 mmol) was dissolved in tetrahydrofurane (170 ml), and cooled to −78° C., n-butyl lithium (67.3 ml, 168.2 mmol) was slowly added thereto, and it was agitated for 1 hour. 2-bromoanthraquinone (21 g, 73.1 mmol) was added, the temperature was increased to normal temperature, and it was agitated for 3 hours. The saturated ammonium chloride aqueous solution was added, the water layer was removed, dried with anhydrous magnesium sulfate, filtered, and dried under reduced pressure. It was recrystallized with ethyl ether and petroleum ether to manufacture the compound of Formula 1-B (32.3 g, 82%).

MS: $[M+H]^+=544$

[Formula 1-C]

The compound of Formula 1-B (32.3 g, 59.5 mmol), potassium iodide (29.6 g, 178.4 mmol), sodium hyphophosphite (38 g, 256.8 mmol) were put into the acetic acid (40 mL), heated and agitated for 3 hours, cooled to normal temperature, and the precipitate was filtered, and recrystallized with ethanol to manufacture the compound of Formula 1-C (25.5 g, 84%).

MS: $[M+H]^+=510$

[Formula 1-D]

In the synthesis of the compound of Formula 1-A of Preparation Example 1, it was synthesized using the same method as the synthesis method of the compound of Formula 1-A, except that Formula 1-C was used instead of 2-bromo-9,10-di(2-naphthyl)anthracene, to manufacture Formula 1-D.

MS: $[M+H]^+=557$

84

Preparation Example 3
Synthesis of the Compound of the Following
Formula 1-E

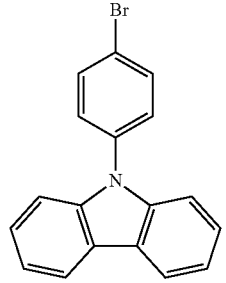

[Formula 1-E]

Carbazole (3.3 g, 20 mmol), 1-bromo-4-iodobenzene (3.0 mL, 24 mmol), potassium carbonate ($K_2CO_3$, 5.6 g, 40 mmol), copper iodide (CuI, 1.9 g, 1.0 mmol) and xylene 50 mL were refluxed under a nitrogen atmosphere. After it was cooled to normal temperature, the product was extracted with ethyl acetate and water was removed with anhydrous magnesium sulfate, and the solvent was removed under reduced pressure. After the compound was obtained by passing it through a silicagel column using the hexane solvent, the solvent was removed under the reduced pressure, and dried under the vacuum to manufacture the white solid compound of Formula 1-E (1.6 g, 25%).

MS: $[M+H]^+=323$

Preparation Example 4
Synthesis of the Compounds of the Following
Formulas 1-F, 1-G, 1-H

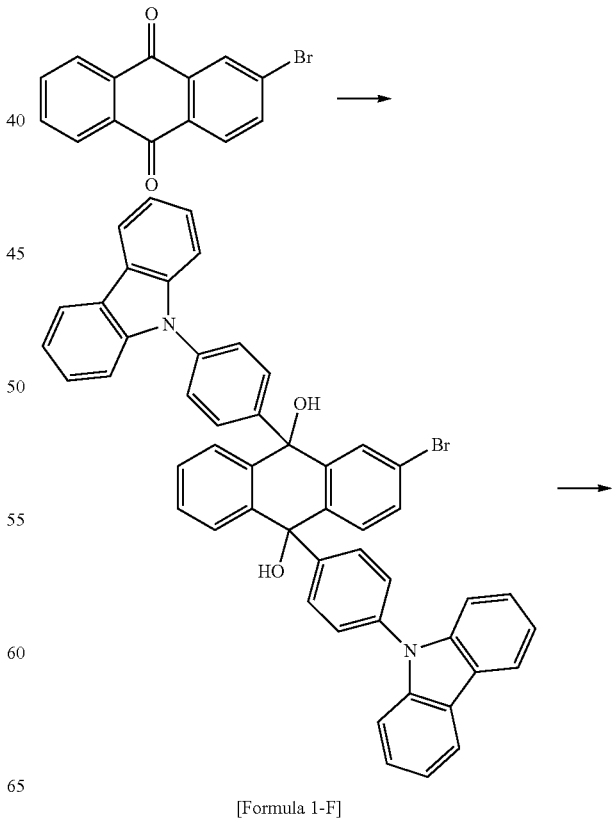

[Formula 1-F]

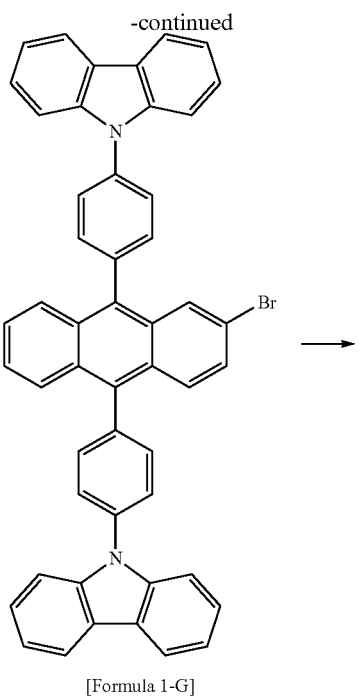

[Formula 1-G]

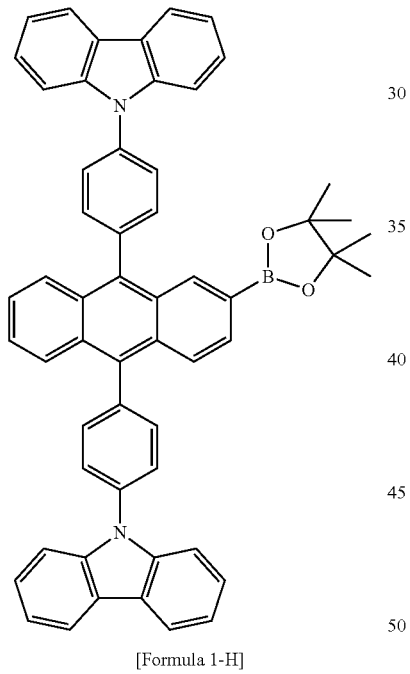

[Formula 1-H]

[Formula 1-F]

The compound of Formula 1-E (4.38 g, 13.2 mmol) was dissolved in dried tetrahydrofurane (80 mL) under the nitrogen atmosphere. The above solution was cooled to −78° C., n-butyl lithium (6.6 mL, 2.5 M hexane solution) was slowly added to the cooled solution for 10 min, and agitated at −78° C. for about 40 min. 2-bromoanthraquinone compound (3.59 g, 5.5 mmol) was added to the reaction mixture, and further agitated at −78° C. for 3 hours. The mixture was agitated at room temperature for about 1 hour. To the above mixture, aqueous ammonium chloride solution (50 mL) was applied. The organic layer was separated, and the aqueous solution layer was extracted with diethyl ether (60 mL). The extracted organic solution layer was dried with magnesium sulfate and concentrated under the reduced pressure. The obtained solid was suspended with diethyl ether, agitated for 1 hour, and filtered. After the drying, the compound of Formula 1-F (3.32 g, 73%) that was the dialcohol compound was manufactured.

MS: $[M+H]^+=774$

[Formula 1-G]

The compound of Formula 1-F (2.82 g, 3.65 mmol) was added to the dispersion solution of the acetic acid (60 mL), potassium iodic acid (3.32 g, 20 mmol) and phosphinate hydrate (3.52 g, 40 mmol). The mixture was continuously agitated, refluxed for about 3 hours, and cooled to room temperature. The mixture was filtered, washed with ethanol, and dried under the vacuum to manufacture the compound of Formula 1-G (2.87 g, 90%).

MS: $[M+H]^+=740$

[Formula 1-H]

In the manufacturing method of the compound of Formula 1-A of Preparation Example 1, the compound of Formula 1-H was synthesized using the same method as the manufacturing method of the compound of Formula 1-A, except that the compound of Formula 1-G was used instead of 2-bromo-9,10-di(2-naphthyl)anthracene.

MS: $[M+H]^+=787$

Preparation Example 5

Synthesis of the Compounds of the Following Formulas 1-I, 1-J, 1-K

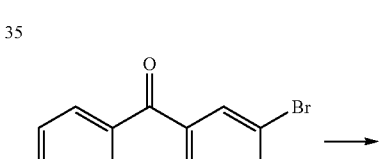

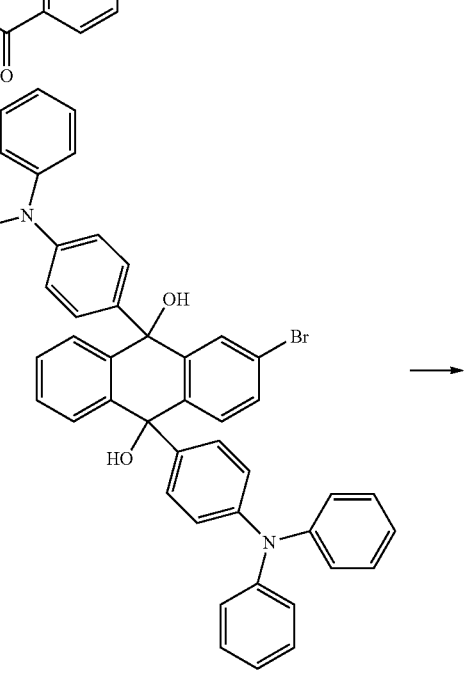

[Formula 1-I]

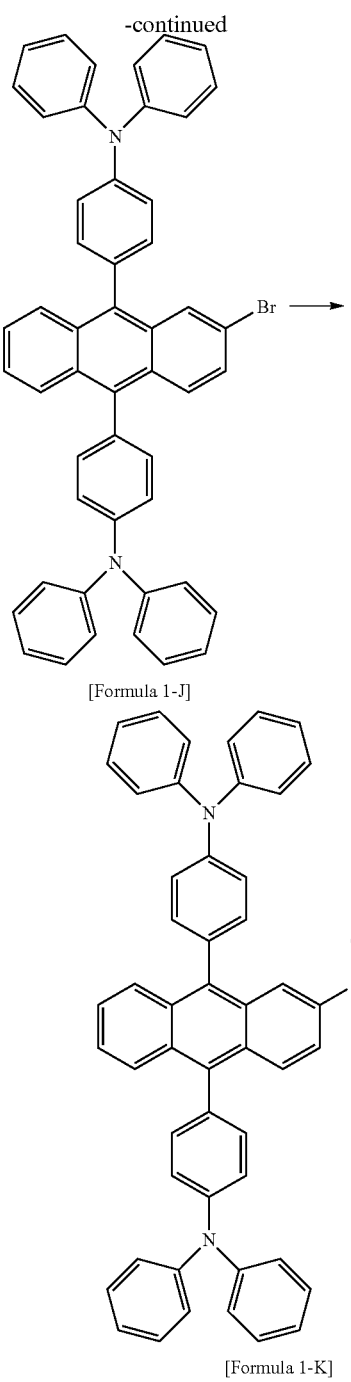

ing method of the compound of Formula 1-C, except that the compound of Formula 1-I was used instead of the compound of Formula 1-B.

MS: [M+H]⁺=744

[Formula 1-K]

In the manufacturing method of the compound of Formula 1-A of Preparation Example 1, the compound of Formula 1-K was manufactured using the same method as the manufacturing method of the compound of Formula 1-A, except that the compound of Formula 1-J was used instead of 2-bromo-9,10-di(2-naphthyl)anthracene.

MS: [M+H]⁺=791

Preparation Example 6

Synthesis of the Compounds of the Following Formulas 1-L, 1-M

[Formula 1-I]

In the manufacturing method of the compound of Formula 1-B of Preparation Example 2, the compound of Formula 1-I was manufactured using the same method as the manufacturing method of the compound of Formula 1-B, except that 4-bromo-triphenylamine was used instead of 1-bromo-naphthalene.

MS: [M+H]⁺=778

[Formula 1-J]

In the manufacturing method of the compound of Formula 1-C of Preparation Example 2, the compound of Formula 1-J was manufactured using the same method as the manufactur-

90

Preparation Example 7

Synthesis of the Compounds of the Following Formulas 1-N, 1-O

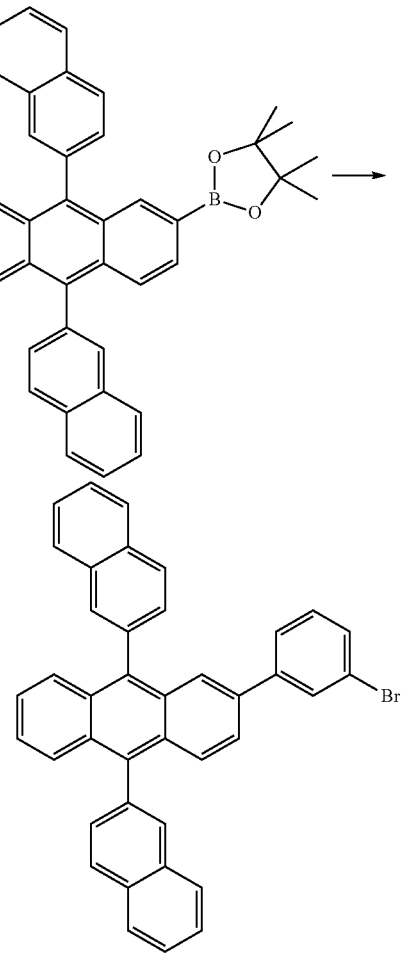

[Formula 1-N]

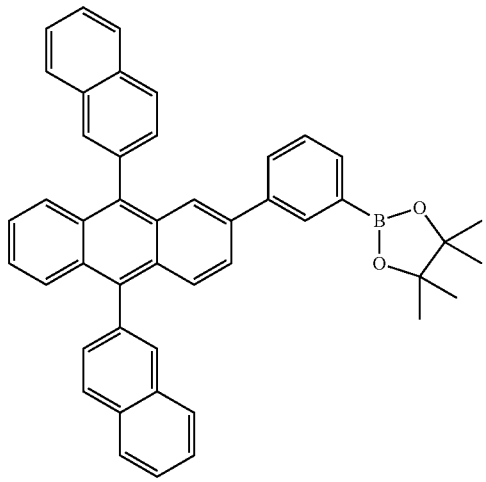

[Formula 1-O]

89

-continued

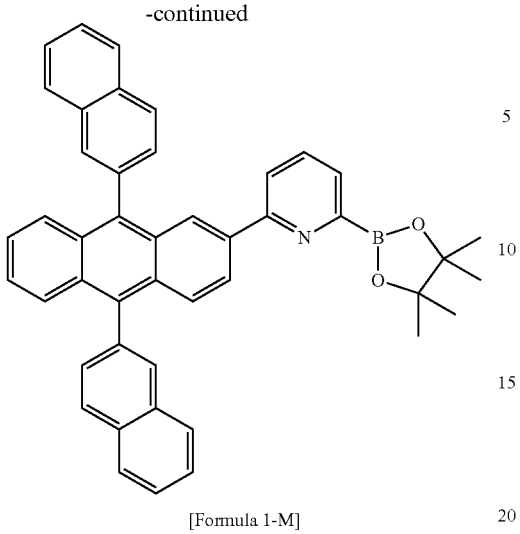

[Formula 1-M]

[Formula 1-L]

After the compound of Formula 1-A (5.56 g, 10.0 mmol) and 2,6-dibromopyridine (2.37 g, 10.0 mmol) were dissolved in tetrahydrofurane (100 mL), 2M potassium carbonate aqueous solution (20 mL) was added thereto, and tetrakistriphenylphosphino palladium $(Pd(PPh_3)_4$ (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-L (3.81 g, 65%).

MS: $[M+H]^+=587$

[Formula 1-M]

To the compound of Formula 1-L (9.84 g, 16.8 mmol), bis(pinacolato)diboron (4.7 g, 18.5 mmol) and potassium acetate (4.96 g, 50.5 mmol) were suspended in dioxane (100 mL). To the suspension solution, $Pd(dba)_2$ (0.29 g, 3 mol %) and $PCy_3$ (0.28 g, 6 mol %) were added. The mixture was agitated and refluxed for about 8 hours, and cooled to normal temperature. The mixture was diluted with water (100 mL), and extracted with dichloromethane (3×50 mL). The organic extract material was dried over magnesium sulfate and filtered. The filtered solution was concentrated under the reduced pressure, recrystallized with ethyl ether and hexane to manufacture the compound of Formula 1-M (7.99 g, 75%).

MS: $[M+H]^+=634$

[Formula 1-N]

In the manufacturing method of the compound of Formula 1-L of Preparation Example 6, the compound of Formula 1-N was manufactured using the same method as the manufacturing method of the compound of Formula 1-L, except that 1-bromo-3-iodobenzene was used instead of 2,6-dibromopyridine.

MS: [M+H]$^+$=586

[Formula 1-O]

In the manufacturing method of the compound of Formula 1-M of Preparation Example 6, the compound of Formula 1-O was manufactured using the same method as the manufacturing method of the compound of Formula 1-M, except that the compound of Formula 1-N was used instead of the compound of Formula 1-L.

MS: [M+H]$^+$=633

Preparation Example 8

Synthesis of the Compounds of the Following Formulas 2-A, 2-B

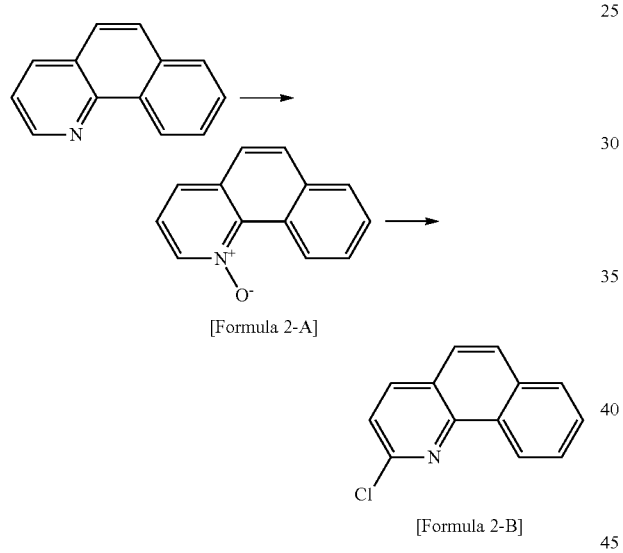

Benzo[h]quinoline (18 g, 100 mmol) was dissolved in 400 mL chloroform (CHCl$_3$), and cooled to 0~5° C. To the mixture, the MCPBA (meta-chloroperoxybenzoic acid) (30.0 g, 150 mmol) solution that was dissolved in 600 mL chloroform was slowly added. The produced mixture was agitated at room temperature for 4 hours, washed with 5% K$_2$CO$_3$ solution (6×600 mL), dried with anhydrous magnesium sulfate, concentrated under the reduced pressure, recrystallized with diethyl ether to manufacture the compound of Formula 2-A (17 g, 87%).

MS: [M+H]$^+$=196

20 mL POCl$_3$ was diluted with 100 mL chloroform, cooled to 0~5° C., and the compound of Formula 2-A (8 g, 4.1 mmol) was slowly added. After it was agitated and refluxed for 2 hours, it was cooled to room temperature and an excessive amount of iced water was poured. The produced mixture was neutralized with the NH$_4$OH solution, and extracted with chloroform (3×200 mL). The collected chloroform organic layer was washed with 200 mL water, dried with anhydrous magnesium sulfate, and distilled under the reduced pressure.

Under the Hexane:CH$_2$Cl$_2$=20:1 condition, through the column chromatography, the compound of Formula 2-B (4.9 g, 56%) was manufactured.

MS: [M+H]$^+$=214

Preparation Example 9

Synthesis of the Compounds of the Following Formulas 2-C, 2-D

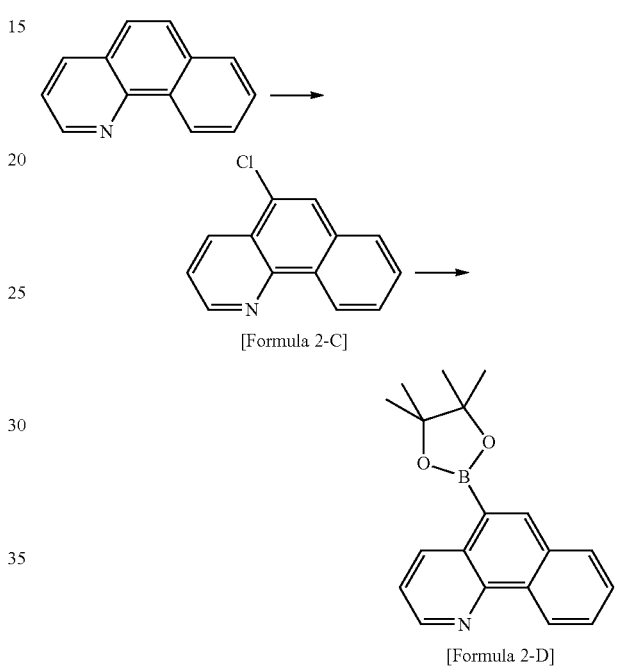

[Formula 2-C]

Benzo[h]quinoline (215.5 mg, 1.2 mmol) was added to the dispersion solution of acetonitrile (MeCN) 10 mL and PhICl$_2$ (404.0 mg, 1.5 mmol, 1.3 equiv.). The mixture was continuously agitated, refluxed for about 12 hours, and cooled to room temperature. It was diluted with chloroform 50 mL, washed with 200 mL water, dried with anhydrous magnesium sulfate, and distilled under the reduced pressure. Under the Hexane:CH$_2$Cl$_2$=20:1 condition, through the column chromatography, the compound of Formula 2-C (77 mg, 30%) was manufactured.

MS: [M]$^+$=214

[Formula 2-D]

In the manufacturing method of the compound of Formula 1-M of Preparation Example 6, the compound of Formula 2-D was manufactured using the same method as the manufacturing method of the compound of Formula 1-M, except that the compound of Formula 2-C was used instead of the compound of Formula 1-L.

MS: [M+H]$^+$=306

Preparation Example 10

Synthesis of the Compound of the Following Formulas 2-E

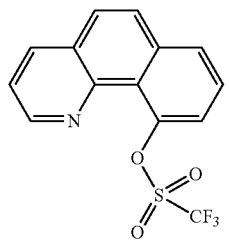

[Formula 2-E]

10-hydroxybenzo[h]quinoline (19.5 g, 100 mmol) was dissolved in tetrahydrofurane (170 ml), cooled to 0° C., and triethylamine (21 ml, 150 mmol) was added thereto and agitated for 10 mins. While the temperature was maintained at 0° C., trifluoromethanesulfonic anhydride (24.6 ml, 150 mmol) was added and agitated for 2 hours. The temperature was increased to normal temperature and it was further agitated for 3 hours. The mixture was washed with 200 mL water, dried with anhydrous magnesium sulfate, and distilled under the reduced pressure. It was recrystallized with ethanol to manufacture the compound of Formula 2-E compound (17.7 g, 65%).

MS: $[M+H]^+$=274

Preparation Example 11

Synthesis of the Compound of the Following Formulas 2-F

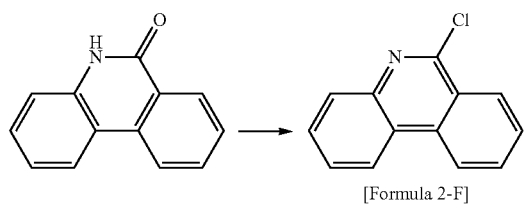

[Formula 2-F]

6-(5H)-phenanthridinone (19.5 g 100 mmol) was added to the dispersion solution of phosphorus oxychloride ($POCl_3$) (150 ml) and dimethylaniline (6 mL). The mixture was continuously agitated, refluxed for about 3 hours, and cooled to room temperature. Phosphorus oxychloride was distilled under the reduced pressure and removed, the remaining material was added to iced water, it was neutralized with the $NH_4OH$ solution and extracted with chloroform (3×200 mL). The collected chloroform organic layer was washed with 200 mL water, dried with anhydrous magnesium sulfate, and distilled under the reduced pressure. Under the Hexane:$CH_2Cl_2$=20:1 condition, through the column chromatography, the compound of Formula 2-F (11.3 g, 53%) was manufactured.

MS: $[M+H]^+$=214

Preparation Example 12

Synthesis of the Compound of the Following Formulas 2-G

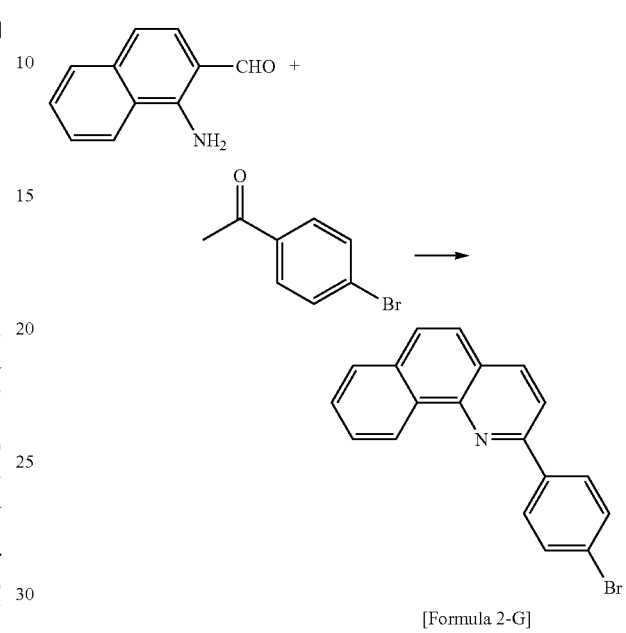

[Formula 2-G]

Under the nitrogen atmosphere, 1-amino-2-naphthalenecarbaldehyde (0.25 g, 1.45 mmol) and 4-bromoacetophenone (2.88 g, 1.45 mmol) were dispersed in EtOH 15 mL, and 0.5 mL of the solution in which KOH was saturated and dissolved in EtOH was slowly added thereto. The obtained mixture was refluxed and agitated for 15 hours. After it was cooled to room temperature, the produced solid was filtered, washed with EtOH, and dried under the vacuum to manufacture the compound of Formula 2-G (0.290 g, 60%).

MS: $[M+H]^+$=335

Preparation Example 13

Synthesis of the Compound of the Following Formulas 2-H

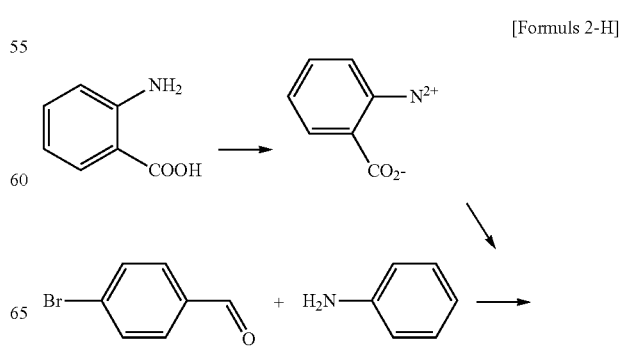

[Formuls 2-H]

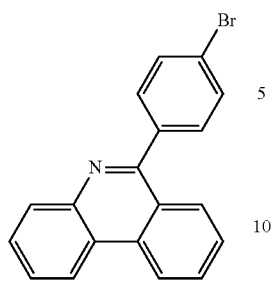

Isoamyl nitride (0.54 mL, 4.1 mmol) was added to dichloroethane 50 mL, agitated, and anthranylnic acid (0.51 g, 3.7 mmol) that was completely dissolved in dichloroethane 25 mL was slowly dropped. Benzene-diazonium-2-carboxylate thusly manufactured was added to the reaction mixture in which 4-bromo-benzaldehyde (0.68 g, 3.7 mmol) and aniline (0.344 g, 3.7 mmol) were dispersed in dichloroethane 50 mL, agitated and refluxed. If the color of the reaction solution was changed from yellow to dark brown, it was cooled to room temperature. Dichloroethane was removed by performing distillation at the reduced pressure, purified through the column chromatography by using the hexane/ethyl acetate mixture solution to obtain the compound of Formula 2-H (0.716 g, 58%).

MS: $[M+H]^+=334$

Preparation Example 14

Synthesis of the Compound of the Following Formulas 2-I

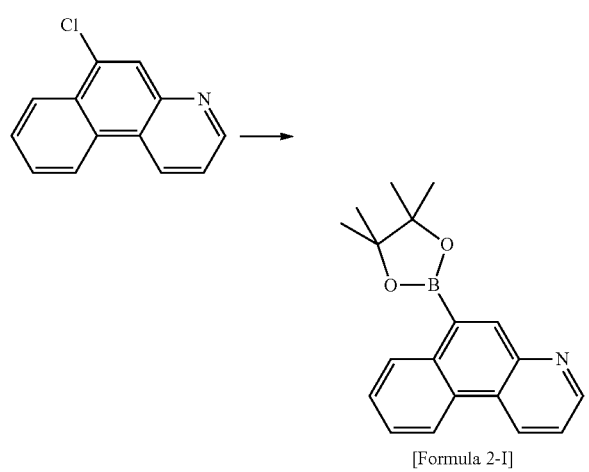

[Formula 2-I]

In the manufacturing method of the compound of Formula 1-M of Preparation Example 6, the compound of Formula 2-I was manufactured using the same method as the manufacturing method of the compound of Formula 1-M, except that 6-chlorobenzo[f]quinoline was used instead of the compound of Formula 1-L.

MS: $[M+H]^+=306$

Example 1

Synthesis of the Compound of the Following Formula 1-2

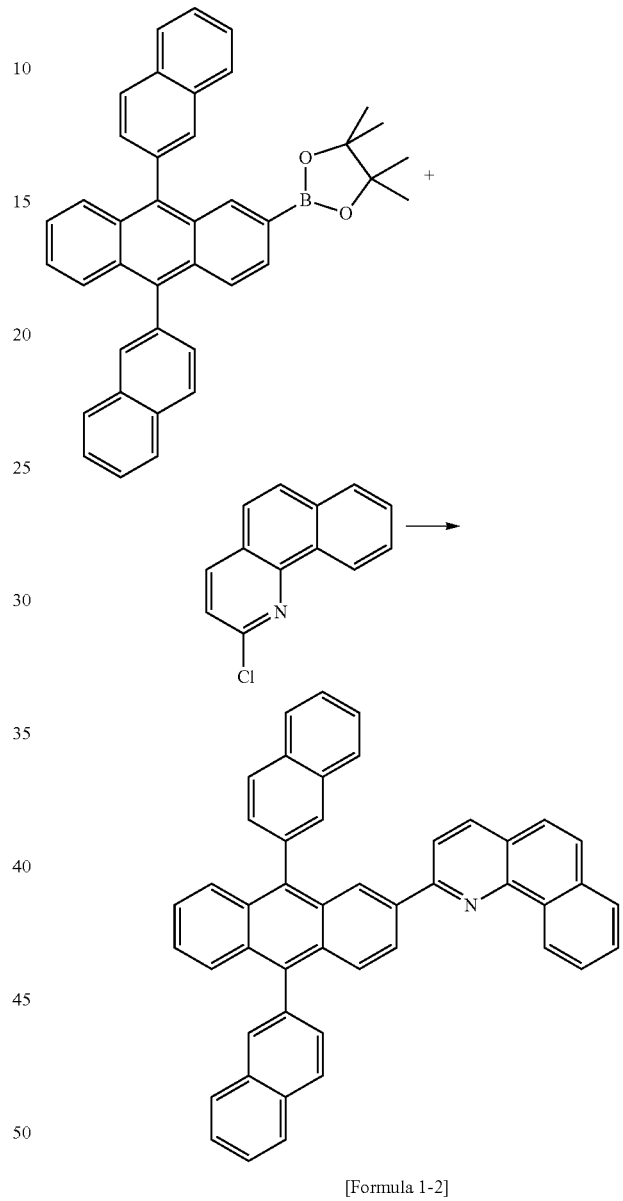

[Formula 1-2]

After the compound of Formula 1-A (5.56 g, 10.0 mmol) and the compound of Formula 2-B (2.13 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-2 (3.76 g, 62%).

MS: $[M+H]^+=608$

Example 2

Synthesis of the Compound of the Following Formula 1-3

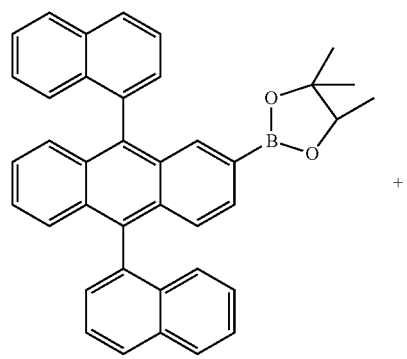

+

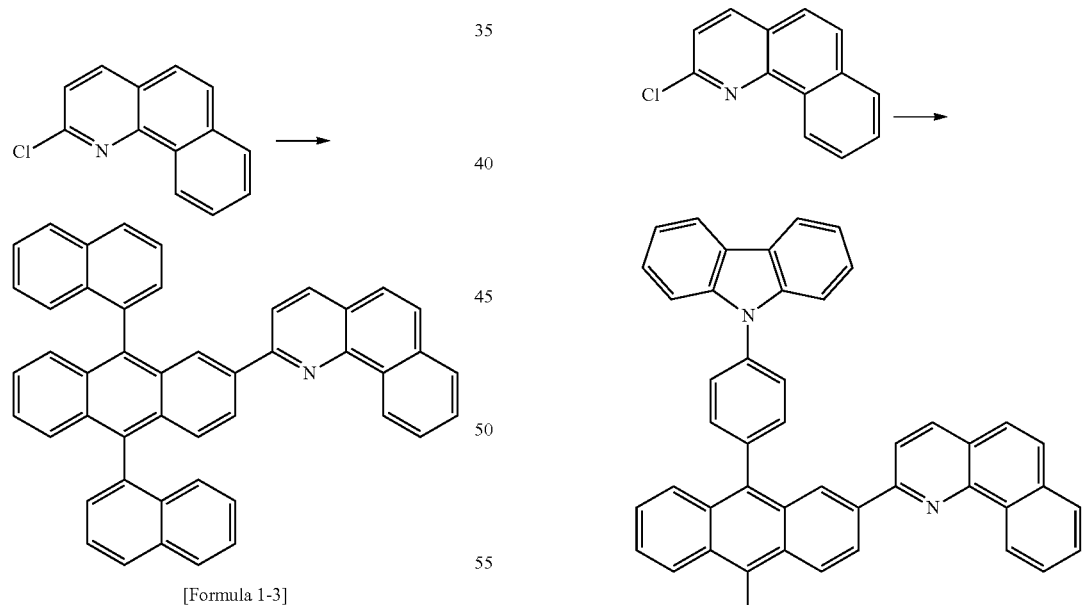

[Formula 1-3]

In the manufacturing method of the compound of Formula 1-2 of Example 1, the compound of Formula 1-3 was manufactured using the same method as the manufacturing method of the compound of Formula 1-2, except that the compound of Formula 1-D was used instead of the compound of Formula 1-A.

MS: [M+H]$^+$=608

Example 3

Synthesis of the Compound of the Following Formula 1-5

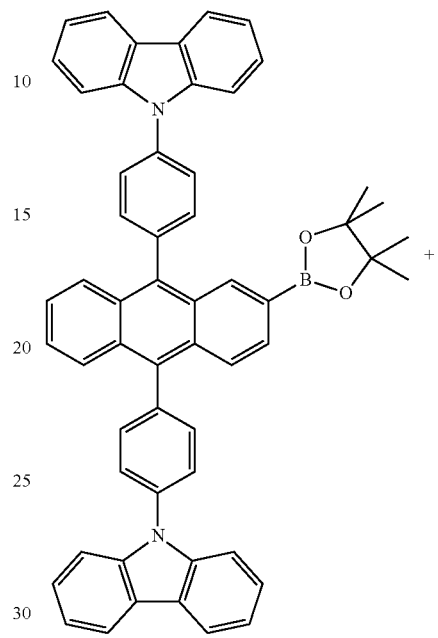

+

[Formula 1-5]

In the manufacturing method of the compound of Formula 1-2 of Example 1, the compound of Formula 1-5 was manufactured using the same method as the manufacturing method of the compound of Formula 1-2, except that the compound of Formula 1-H was used instead of the compound of Formula 1-A.

MS: [M+H]$^+$=838

Example 4

Synthesis of the Compound of the Following Formula 1-17

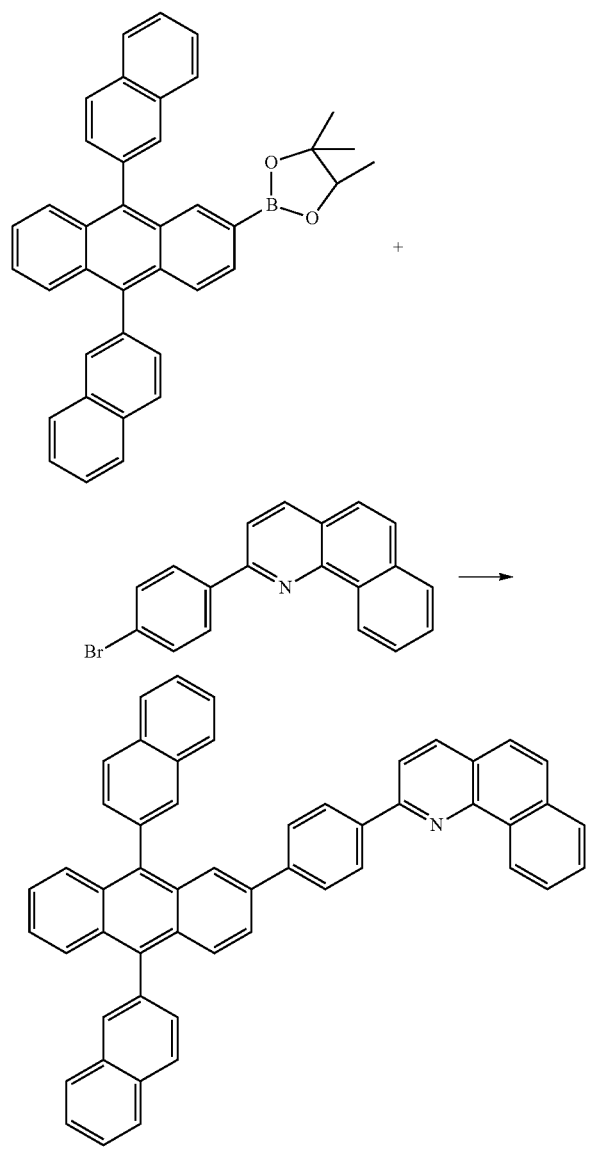

[Formula 1-17]

In the manufacturing method of the compound of Formula 1-2 of Example 1, the compound of Formula 1-17 was manufactured using the same method as the manufacturing method of the compound of Formula 1-2, except that the compound of Formula 2-G was used instead of the compound of Formula 2-B.

MS: [M+H]$^+$=684

Example 5

Synthesis of the Compound of the Following Formula 1-21

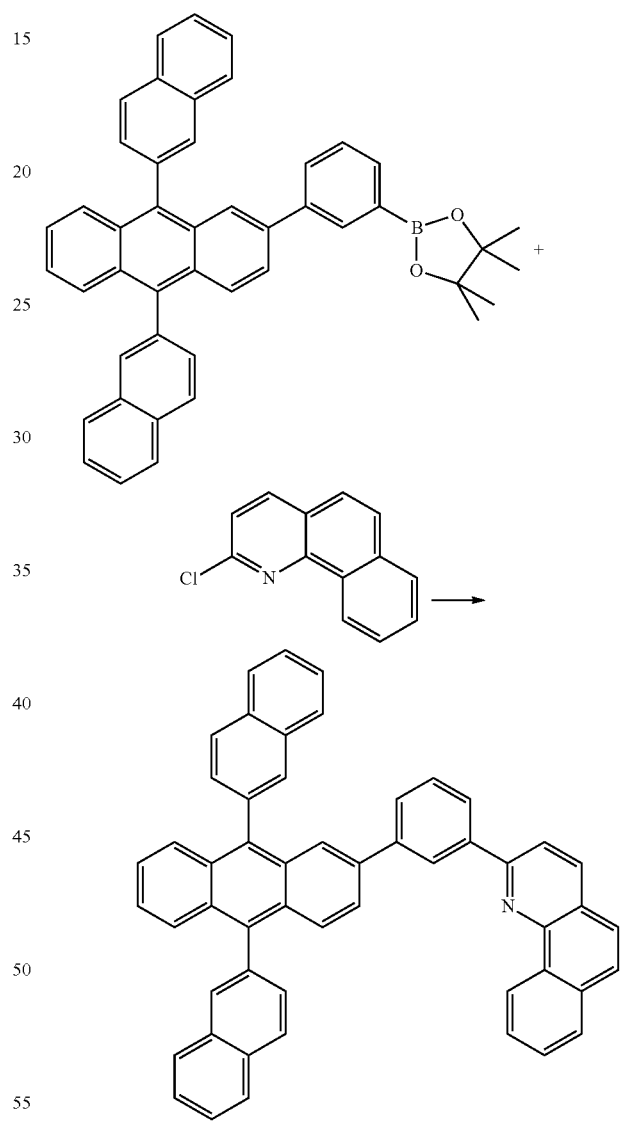

[Formula 1-21]

In the manufacturing method of the compound of Formula 1-2 of Example 1, the compound of Formula 1-21 was manufactured using the same method as the manufacturing method of the compound of Formula 1-2, except that the compound of Formula 1-O was used instead of the compound of Formula 1-A.

MS: [M+H]$^+$=684

Example 6

Synthesis of the Compound of the Following Formula 1-42

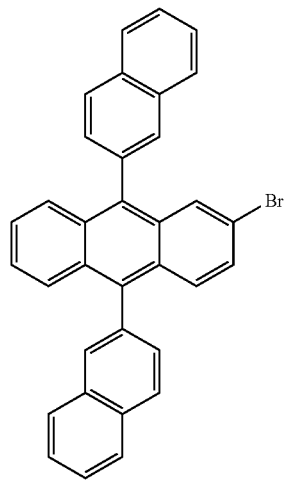

+

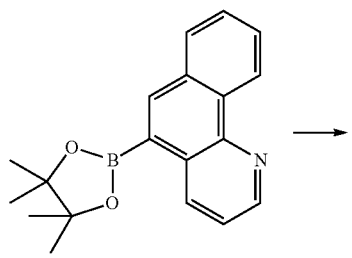

→

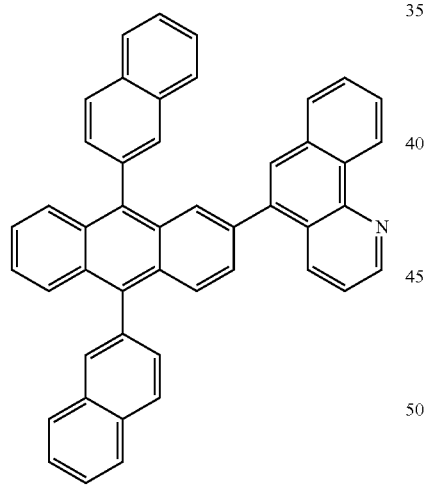

[Formula 1-42]

After 2-bromo-9,10-di(2-naphthyl)anthracene (5.09 g, 10.0 mmol) and the compound of Formula 2-D (3.05 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-42 (4.25 g, 70%).

MS: $[M+H]^+=608$

Example 7

Synthesis of the Compound of the Following Formula 1-65

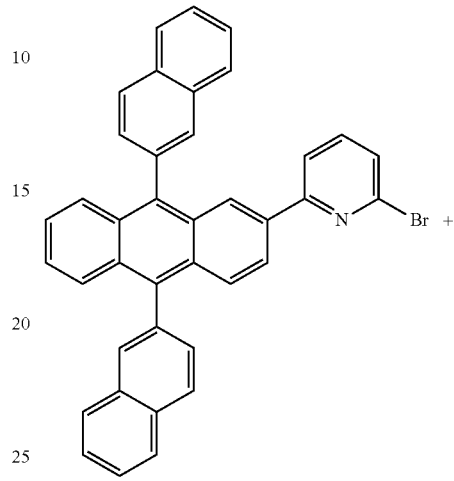

+

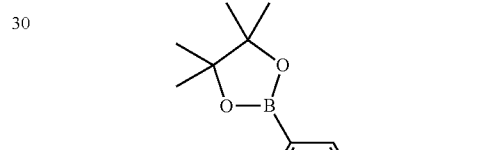

→

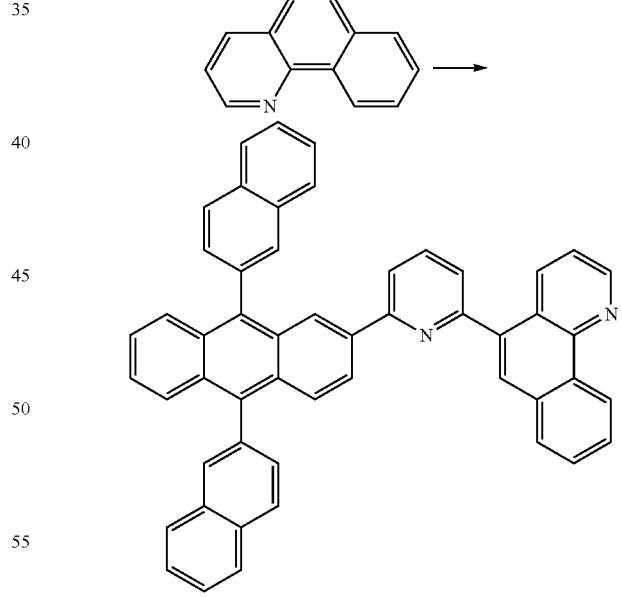

[Formula 1-65]

In the manufacturing method of the compound of Formula 1-42 of Example 6, the compound of Formula 1-65 was manufactured using the same method as the manufacturing method of the compound of Formula 1-42, except that the compound of Formula 1-L was used instead of 2-bromo-9,10-di(2-naphthyl)anthracene.

MS: $[M+H]^+=685$

Example 8

Synthesis of the Compound of the Following Formula 1-82

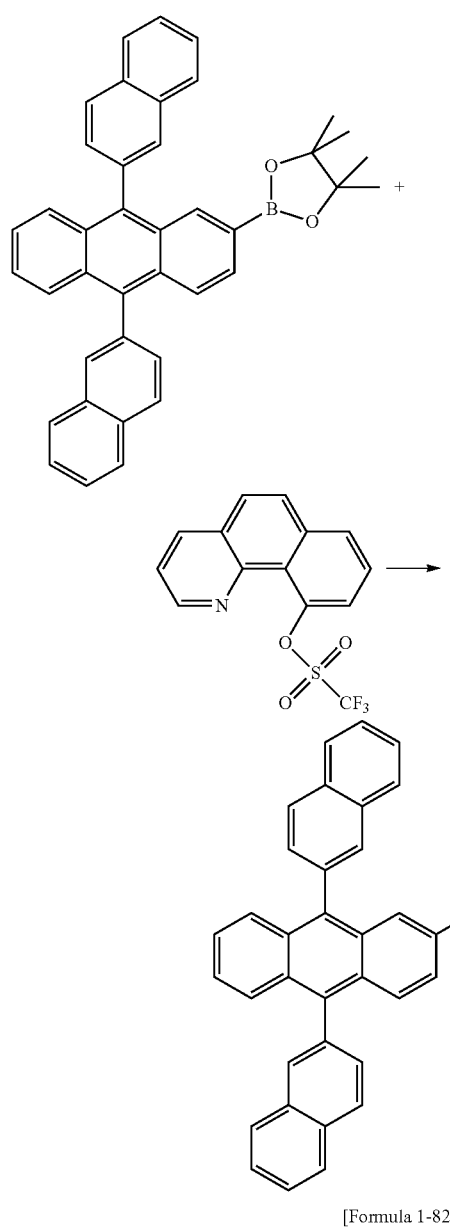

[Formula 1-82]

After the compound of Formula 1-A (5.56 g, 10.0 mmol) and the compound of Formula 2-E (2.73 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 1-82 (4.37 g, 72%).

MS: [M+H]$^+$=608

Example 9

Synthesis of the Compound of the Following Formula 1-92

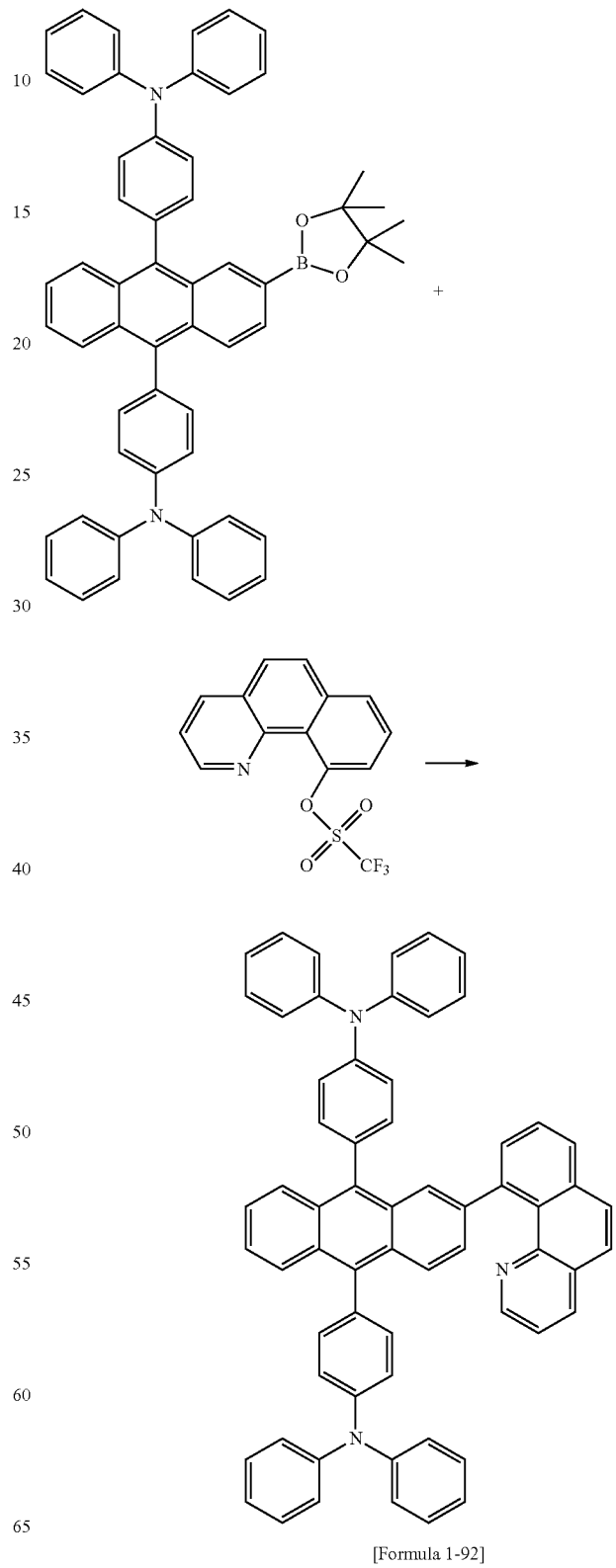

[Formula 1-92]

In the manufacturing method of the compound of Formula 1-82 of Example 8, the compound of Formula 1-92 was manufactured using the same method as the manufacturing method of the compound of Formula 1-82, except that the compound of Formula 1-K was used instead of the compound of Formula 1-A.

MS: [M+H]⁺=842

Example 10

Synthesis of the Compound of the Following Formula 1-105

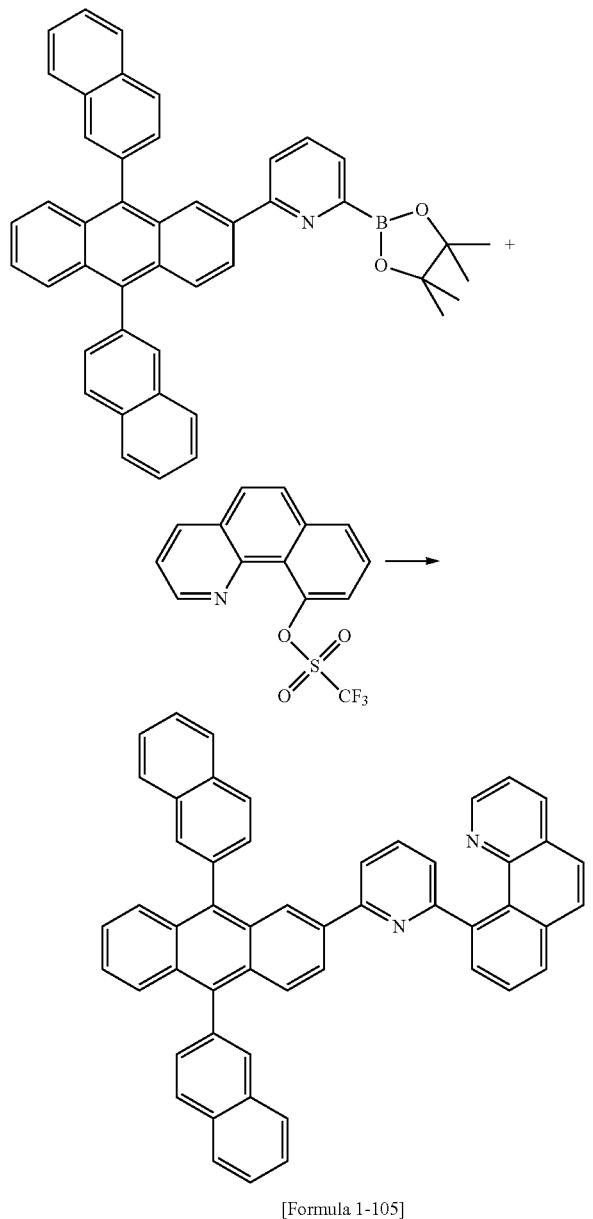

[Formula 1-105]

In the manufacturing method of the compound of Formula 1-82 of Example 8, the compound of Formula 1-105 was manufactured using the same method as the manufacturing method of the compound of Formula 1-82, except that the compound of Formula 1-M was used instead of the compound of Formula 1-A.

MS: [M+H]⁺=685

Example 11

Synthesis of the Compound of the Following Formula 2-2

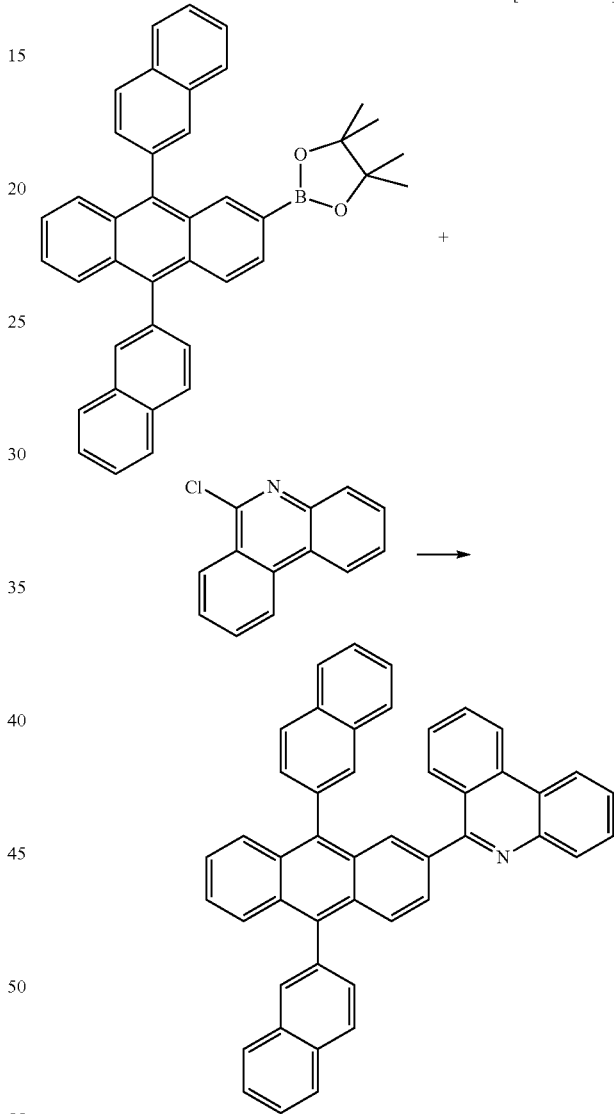

[Formula 2-2]

After the compound of Formula 1-A (5.56 g, 10.0 mmol) and the compound of Formula 2-F (2.13 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 2-2 (4.13 g, 68%).

MS: [M+H]⁺=608

Example 12

Synthesis of the Compound of the Following Formula 2-3

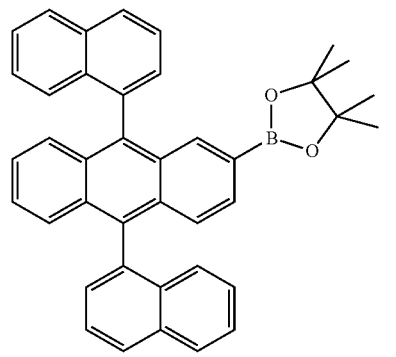

[Formula 2-3]

+

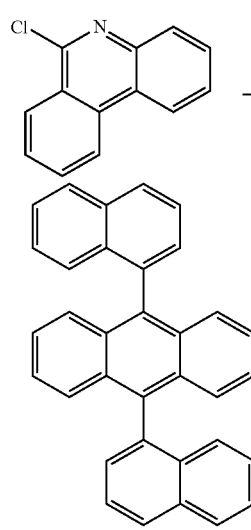

→

In the manufacturing method of the compound of Formula 2-2 of Example 11, the compound of Formula 2-3 was manufactured using the same method as the manufacturing method of the compound of Formula 2-2, except that the compound of Formula 1-D was used instead of the compound of Formula 1-A.

MS: [M+H]$^+$=608

Example 13

Synthesis of the Compound of the Following Formula 2-5

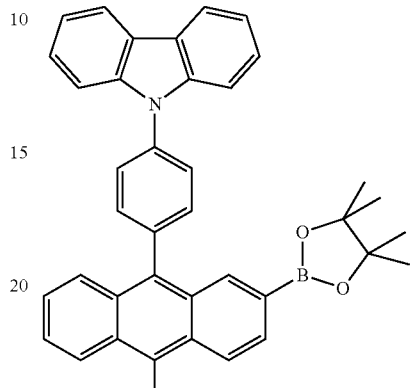

[Formula 2-5]

+

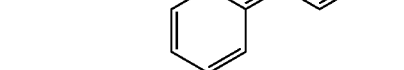
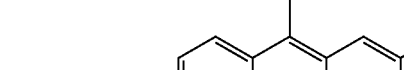
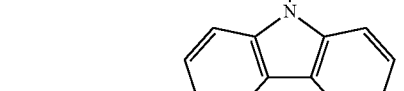

→

In the manufacturing method of the compound of Formula 2-2 of Example 11, the compound of Formula 2-5 was manufactured using the same method as the manufacturing method of the compound of Formula 2-2, except that the compound of Formula 1-H was used instead of the compound of Formula 1-A.

MS: [M+H]$^+$=838

Example 14

Synthesis of the Compound of the Following Formula 2-17

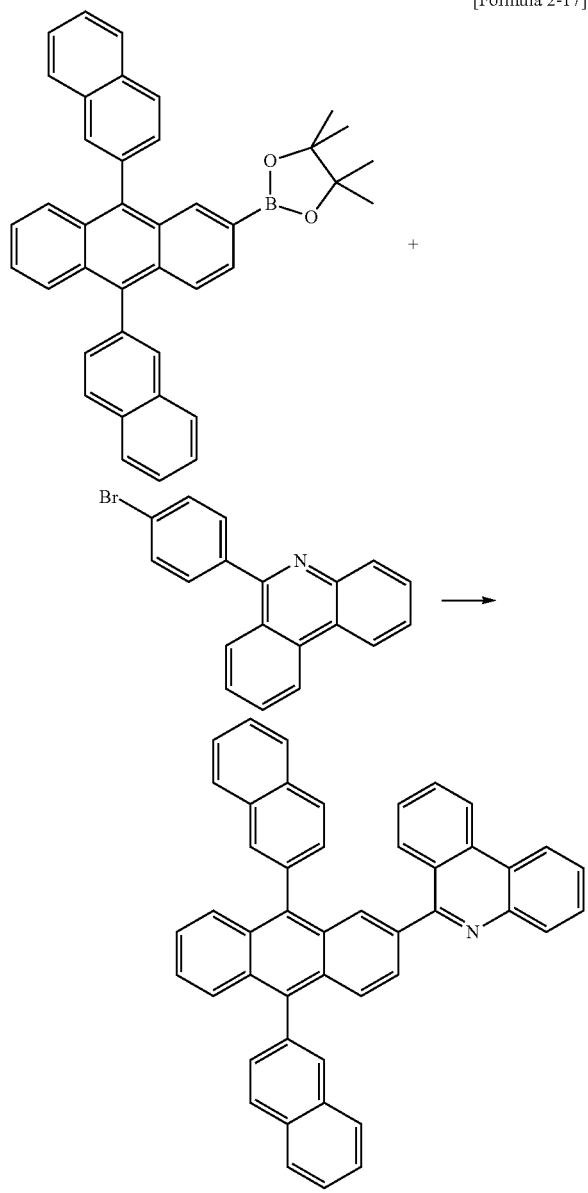

[Formula 2-17]

In the manufacturing method of the compound of Formula 2-2 of Example 11, the compound of Formula 2-17 was manufactured using the same method as the manufacturing method of the compound of Formula 2-2, except that the compound of Formula 2-H was used instead of the compound of Formula 2-F.

MS: [M+H]$^+$=684

Example 15

Synthesis of the Compound of the Following Formula 2-25

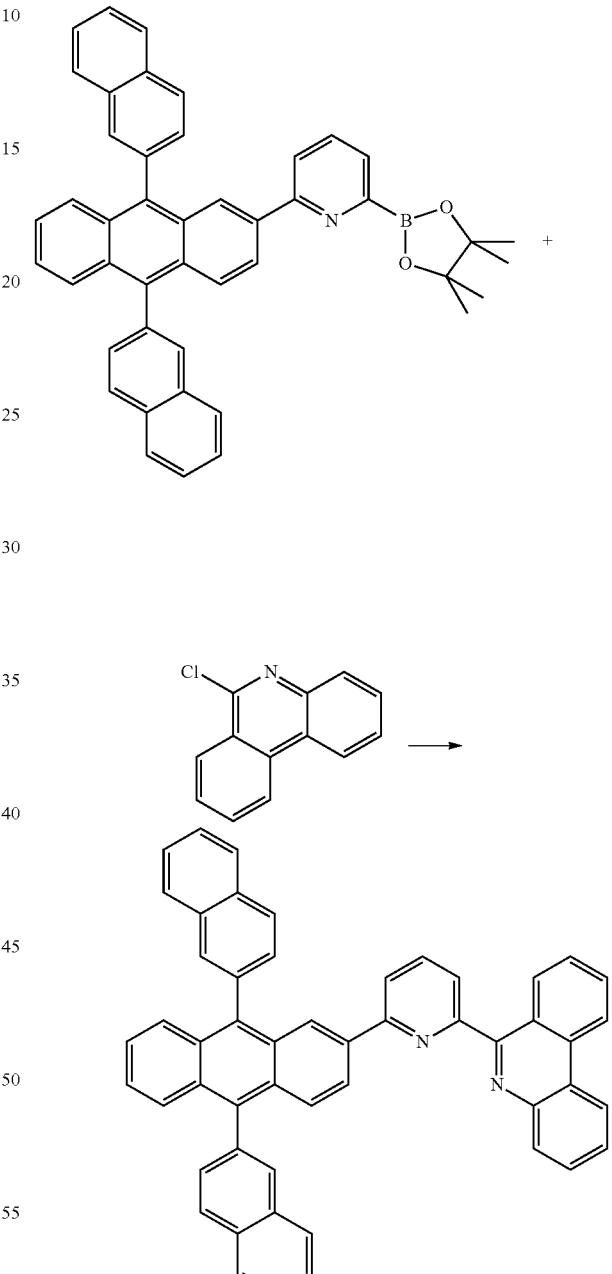

[Formula 2-25]

In the manufacturing method of the compound of Formula 2-2 of Example 11, the compound of Formula 2-25 was manufactured using the same method as the manufacturing method of the compound of Formula 2-2, except that the compound of Formula 1-M was used instead of the compound of Formula 1-A.

MS: [M+H]$^+$=608

Example 16

Synthesis of the Compound of the Following Formula 3-2

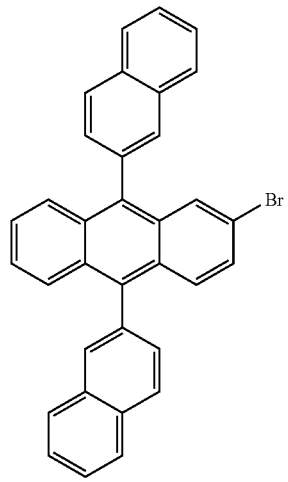

[Formula 3-2]

After 2-bromo-9,10-di(2-naphthyl)anthracene (5.09 g, 10.0 mmol) and the compound of Formula 2-I (3.05 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was cooled to normal temperature, and the produced solid was filtered. The filtered solid was recrystallized with chloroform and ethanol, filtered, and dried to manufacture the compound of Formula 3-2 (4.43 g, 73%).

MS: [M+H]$^+$=608

Example 17

Synthesis of the Compound of the Following Formula 3-25

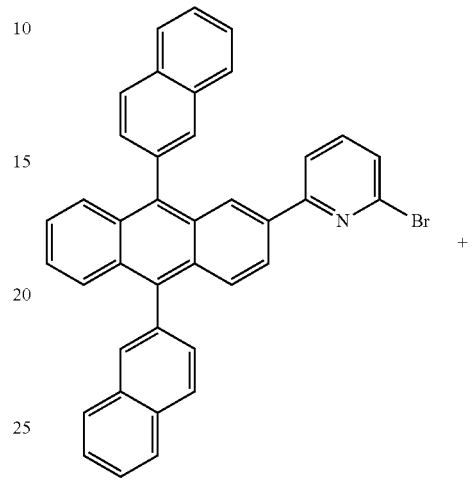

[Formula 3-25]

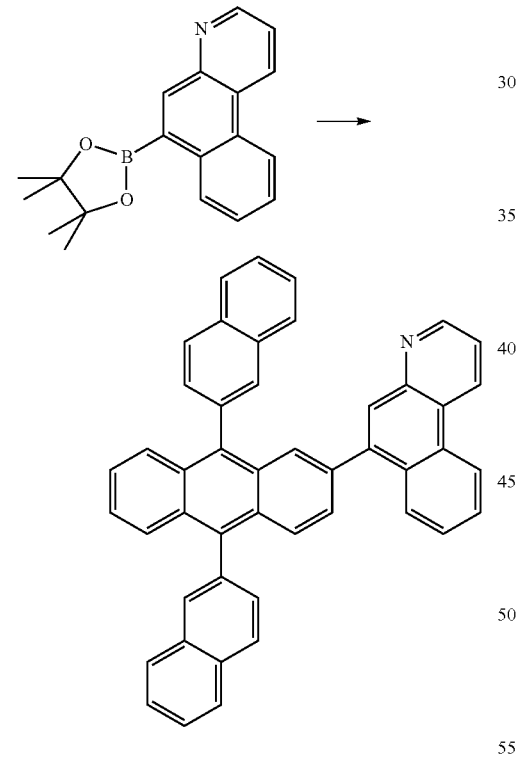

In the manufacturing method of the compound of Formula 3-2 of Example 16, the compound of Formula 3-25 was manufactured using the same method as the manufacturing method of the compound of Formula 3-2, except that the compound of Formula 1-L was used instead of 2-bromo-9,10-di(2-naphthyl)anthracene.

MS: [M+H]$^+$=685

Experimental Example 1

Experimental Example 1-1

A glass substrate on which a thin film of ITO (indium tin oxide) was coated to a thickness of 500 Å was immersed in distilled water having a detergent dissolved therein to wash the substrate with ultrasonic waves. At this time, the detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone and methanol, the resultant product was dried, and transported to the plasma washing machine. In addition, the substrate was washed by using the oxygen plasma for 5 min, and the substrate was transported to the vacuum deposition machine.

On the ITO transparent electrode thus prepared, hexanitrile hexaazatriphenylene (HAT) of the following Formula was coated to thicknesses of 100 Å by vacuum deposition to form a hole injecting layer.

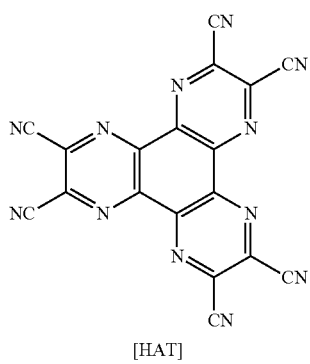

[HAT]

On the hole injection layer, 4,4'-bis[N-(1-naphthyl)-N-phenylamino]biphenyl (NPB) (1000 Å) of the following Formula that was the material that transported the holes was deposited under the vacuum state, thereby forming the hole transport layer.

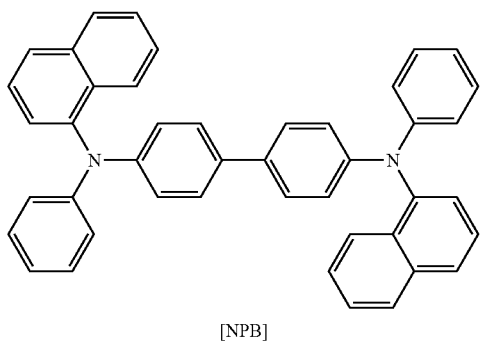

[NPB]

Subsequently, GH and GD as shown below were deposited under the vacuum state at the weight ratio of 20:1 in the film thickness of 300 Å on the hole transport layer, thereby forming the light emitting layer.

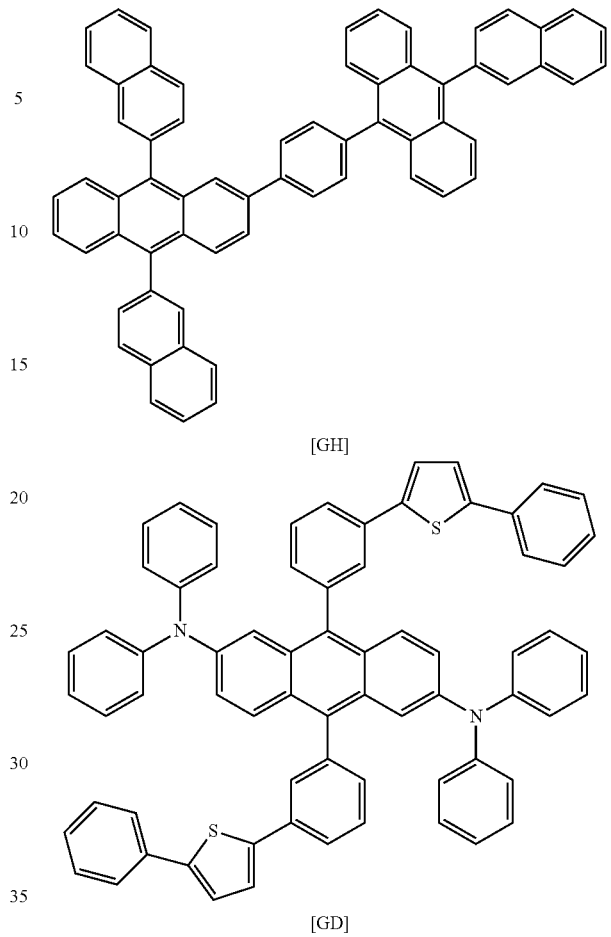

[GH]

[GD]

On the light emitting layer, the compound of Formula 1-2 that was manufactured in Example 1 was deposited under the vacuum state in the thickness of 200 Å, thereby forming the electron transport layer.

On the electron injection and transport layer, lithium fluoride (LiF) in the thickness of 12 Å and aluminium in the thickness of 2000 Å were sequentially deposited, thereby forming the electron injection layer and the cathode.

In the above process, the deposition speed of the organic material was maintained at 0.4 to 0.7 Å/sec, the deposition speed of the lithium fluoride of the cathode was maintained at 0.3 Å/sec, the deposition speed of aluminium was maintained at 2 Å/sec, and the degree of vacuum in the deposition was maintained at $2 \times 10^{-7}$ to $5 \times 10^{-8}$ torr, thereby manufacturing the organic light emitting device.

Experimental Example 1-2

The organic light emitting device was manufactured by using the same method as Experimental Example 1-1, except that the compound of Formula 1-3 was used instead of the compound of Formula 1-2.

Experimental Example 1-3

The organic light emitting device was manufactured by using the same method as Experimental Example 1-1, except that the compound of Formula 1-5 was used instead of the compound of Formula 1-2.

Experimental Example 1-4

The organic light emitting device was manufactured by using the same method as Experimental Example 1-1, except that the compound of Formula 1-17 was used instead of the compound of Formula 1-2.

Experimental Example 1-5

The organic light emitting device was manufactured by using the same method as Experimental Example 1-1, except that the compound of Formula 1-42 was used instead of the compound of Formula 1-2.

Experimental Example 1-6

The organic light emitting device was manufactured by using the same method as Experimental Example 1-1, except that the compound of Formula 1-65 was used instead of the compound of Formula 1-2.

Experimental Example 1-7

The organic light emitting device was manufactured by using the same method as Experimental Example 1-1, except that the compound of Formula 1-82 was used instead of the compound of Formula 1-2.

Experimental Example 1-8

The organic light emitting device was manufactured by using the same method as Experimental Example 1-1, except that the compound of Formula 1-92 was used instead of the compound of Formula 1-2.

Experimental Example 1-9

The organic light emitting device was manufactured by using the same method as Experimental Example 1-1, except that the compound of Formula 1-105 was used instead of the compound of Formula 1-2.

Experimental Example 1-10

The organic light emitting device was manufactured by using the same method as Experimental Example 1-1, except that the compound of Formula 2-2 was used instead of the compound of Formula 1-2.

Experimental Example 1-11

The organic light emitting device was manufactured by using the same method as Experimental Example 1-1, except that the compound of Formula 2-17 was used instead of the compound of Formula 1-2.

Experimental Example 1-12

The organic light emitting device was manufactured by using the same method as Experimental Example 1-1, except that the compound of Formula 2-25 was used instead of the compound of Formula 1-2.

Experimental Example 1-13

The organic light emitting device was manufactured by using the same method as Experimental Example 1-1, except that the compound of Formula 3-2 was used instead of the compound of Formula 1-2.

Experimental Example 1-14

The organic light emitting device was manufactured by using the same method as Experimental Example 1-1, except that the compound of Formula 3-25 was used instead of the compound of Formula 1-2.

Comparative Example 1

The organic light emitting device was manufactured by using the same method as Experimental Example 1-1, except that the E1 compound that was represented by the following Formula was used instead of the compound of Formula 1-2.

Comparative Example 2

The organic light emitting device was manufactured by using the same method as Experimental Example 1-1, except that the E2 compound that was represented by the following Formula was used instead of the compound of Formula 1-2.

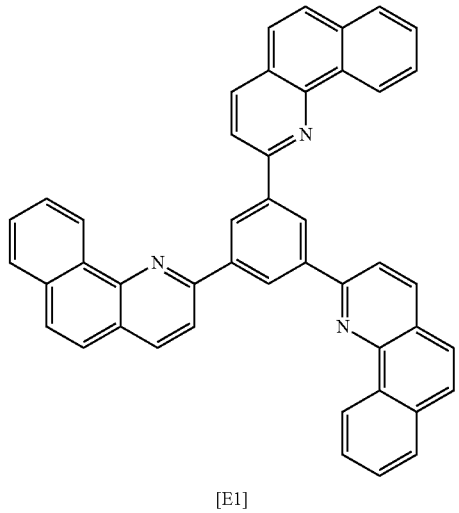

[E1]

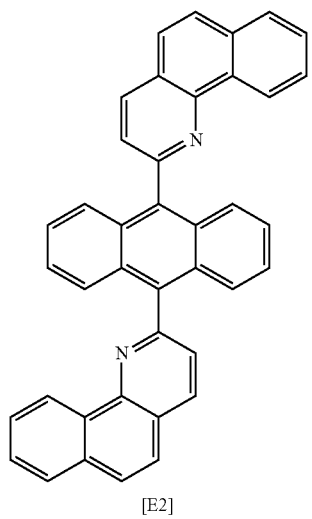

[E2]

As described above, when a current was applied to the manufactured device, the results shown in the following Table 1 were obtained. The values that are described in Table 1 are values that are measured at the current density of 10 mA/cm².

TABLE 1

| | Compound | Voltage (V) | Current efficiency (cd/A) | Color coordinate (x, y) |
|---|---|---|---|---|
| Experimental Example 1-1 | 1-2 | 4.92 | 26.37 | (0.315, 0.651) |
| Experimental Example 1-2 | 1-3 | 5.11 | 22.33 | (0.313, 0.652) |
| Experimental Example 1-3 | 1-5 | 5.24 | 19.52 | (0.314, 0.652) |
| Experimental Example 1-4 | 1-17 | 5.09 | 27.02 | (0.316, 0.653) |
| Experimental Example 1-5 | 1-42 | 5.33 | 20.25 | (0.318, 0.649) |
| Experimental Example 1-6 | 1-65 | 5.10 | 23.55 | (0.319, 0.650) |
| Experimental Example 1-7 | 1-82 | 5.22 | 22.36 | (0.314, 0.649) |
| Experimental Example 1-8 | 1-92 | 5.35 | 19.14 | (0.317, 0.654) |
| Experimental Example 1-9 | 1-105 | 5.15 | 24.52 | (0.321, 0.653) |
| Experimental Example 1-10 | 2-2 | 5.03 | 22.09 | (0.316, 0.655) |
| Experimental Example 1-11 | 2-17 | 5.11 | 25.28 | (0.316, 0.654) |
| Experimental Example 1-12 | 2-25 | 5.21 | 23.01 | (0.317, 0.650) |
| Experimental Example 1-13 | 3-2 | 5.22 | 19.02 | (0.316, 0.648) |
| Experimental Example 1-14 | 3-25 | 5.32 | 22.58 | (0.317, 0.653) |
| Comparative Example 1 | E1 | 5.48 | 19.24 | (0.313, 0.650) |
| Comparative Example 2 | E2 | 5.37 | 21.63 | (0.314, 0.651) |

From the results of Table 1, it can be seen that in the case of when the organic material layer of the organic light emitting device is formed by using the compound of Formula 1 according to the present invention, an increase in efficiency and a reduction in driving voltage are ensured.

Experimental Example 2

Experimental Example 2-1

On the ITO electrode that was manufactured by using the same method as Experimental Example 1-1, hexanitrile hexaazatriphenylene (100 Å), 4,4'-bis[N-(1-naphthyl)-N-phenylamino]biphenyl (NPB) (1000 Å), and GH:GD (weight ratio 20:1) (300 Å) were sequentially deposited under the vacuum, thereby sequentially forming the hole injection layer, hole transport layer, and light emitting layer. The compound of Formula 1-2 and lithium fluoride (LiF) were deposited under the vacuum at the weight ratio of 1:1 thereon, thereby forming the electron transport layer having the thickness of 200 Å. Lithium fluoride (LiF) in the thickness of 12 Å and aluminium in the thickness of 2000 Å were deposited, thereby forming the electron injection layer and the cathode and manufacturing the organic light emitting device.

Experimental Example 2-2

The organic light emitting device was manufactured by using the same method as Experimental Example 21, except that the compound of Formula 1-17 was used instead of the compound of Formula 1-2.

Experimental Example 2-3

The organic light emitting device was manufactured by using the same method as Experimental Example 2-1, except that the compound of Formula 2-2 was used instead of the compound of Formula 1-2.

Experimental Example 2-4

The organic light emitting device was manufactured by using the same method as Experimental Example 2-1, except that the compound of Formula 2-17 was used instead of the compound of Formula 1-2.

Comparative Example 3

The organic light emitting device was manufactured by using the same method as Experimental Example 2-1, except that the E1 compound that was represented by the above Formula was used instead of the compound of Formula 1-2.

Comparative Example 4

The organic light emitting device was manufactured by using the same method as Experimental Example 2-1, except that the E2 compound that was represented by the above Formula was used instead of the compound of Formula 1-2.

As described above, when a current was applied to the manufactured device, the results shown in the following Table 2 were obtained. The voltage, current efficiency and color coordinate values that were described in Table 2 were values that were measured at the current density of 10 mA/cm². The life span was the value that was obtained by measuring a half-life at the current density of 50 mA/cm².

TABLE 2

| | Compound | Voltage (V) | Current efficiency (cd/A) | Color coordinate (x, y) | Lifetime ($T_{50}$) @50 mA/cm² |
|---|---|---|---|---|---|
| Experimental Example 2-1 | 1-2 | 4.42 | 29.37 | (0.317, 0.651) | 1660 hr |
| Experimental Example 2-2 | 1-17 | 4.62 | 31.28 | (0.315, 0.650) | 1520 hr |
| Experimental Example 2-3 | 2-2 | 4.92 | 23.85 | (0.315, 0.653) | 1750 hr |
| Experimental Example 2-4 | 2-17 | 4.85 | 27.57 | (0.317, 0.656) | 1430 hr |
| Comparative Example 4 | E1 | 5.02 | 21.42 | (0.314, 0.653) | 1050 hr |
| Comparative Example 5 | E2 | 4.86 | 24.82 | (0.317, 0.654) | 1370 hr |

From the results of Table 2, it can be seen that in the case of when the organic material layer of the organic light emitting device is formed by using the compound of Formula 1 according to the present invention, an increase in efficiency and a reduction in driving voltage, and stability of the device are ensured.

The invention claimed is:
1. A compound that is represented by Formula 1:

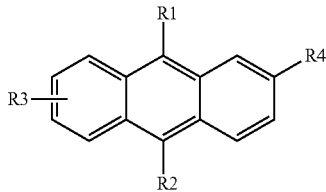

[Formula 1]

wherein R1 and R2 are the same as or different from each other, and are each independently selected from the group consisting of a $C_6$~$C_{40}$ aryl group that is unsubstituted or substituted by at least one group that is selected from the group consisting of halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;
a $C_2$~$C_{40}$ heteroaryl group that is unsubstituted or substituted by at least one group that is selected from the group consisting of halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group; and
an arylamino group that is unsubstituted or substituted by at least one group that is selected from the group consisting of halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group,
R3 is selected from the group consisting of hydrogen; a $C_1$~$C_{40}$ alkyl group that is unsubstituted or substituted by at least one group that is selected from the group consisting of a halogen, an amino group, a nitrile group, nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;
a $C_3$~$C_{40}$ cycloalkyl group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;
a $C_6$~$C_{40}$ aryl group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;
a $C_2$~$C_{40}$ heteroaryl group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group; and
a $C_6$~$C_{40}$ arylamino group that is unsubstituted or substituted by at least one group that is selected from the group consisting of a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group,
R4 is represented by the group selected from the following Formulas 2 to 4,

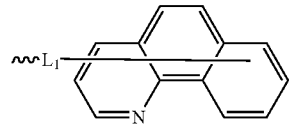

[Formula 2]

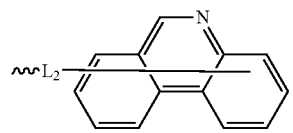

[Formula 3]

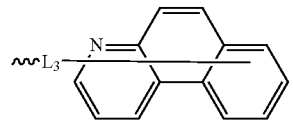

[Formula 4]

wherein $L_1$ to $L_3$ are each independently a direct bond; or are selected from the group consisting of a $C_2$~$C_{40}$ alkenylene group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;
a $C_6$~$C_{40}$ arylene group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group;
a $C_2$~$C_{40}$ heteroarylene group that is unsubstituted or substituted by at least one group that is selected from the group consisting of a halogen, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group; and
a $C_6$~$C_{40}$ arylamino group that is unsubstituted or substituted by at least one group that is selected from the group consisting of a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_2$~$C_{40}$ heteroaryl group.

2. The compound according to claim 1, wherein Formula 1 is selected from the groups that are represented by the following Formulas 5 to 9:

[Formula 5]

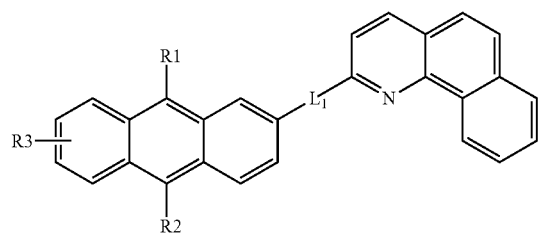

[Formula 6]

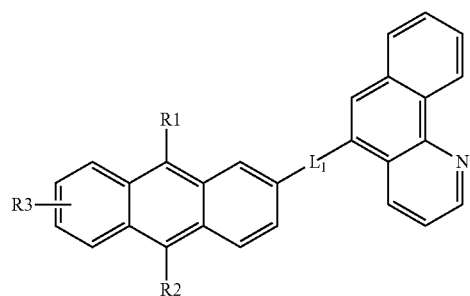

[Formula 7]

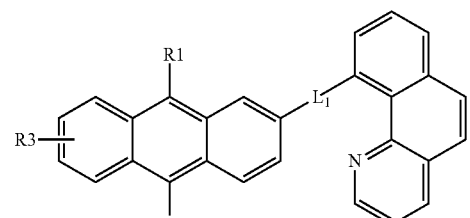

[Formula 8]

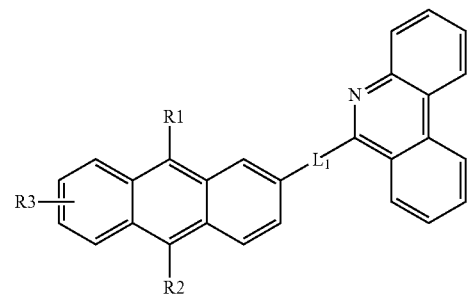

[Formula 9]

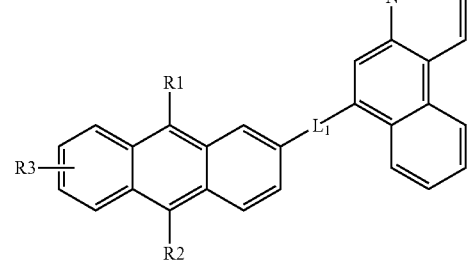

wherein R1 to R3 and $L_1$ to $L_3$ are the same as those defined in Formula 1.

3. The compound according to claim 1, wherein R1 and R2 of Formula 1 are the same as each other and an aryl group.

4. The compound according to claim 1, wherein R1 and R2 of Formula 1 are the same as each other and a heteroaryl group.

5. The compound according to claim 1, wherein R1 and R2 of Formula 1 are the same as each other and an arylamino group that is substituted by an aryl group or a heteroaryl group.

6. The compound according to claim 1, wherein R1 and R2 of Formula 1 are selected from the group consisting of the following Structural Formulas:

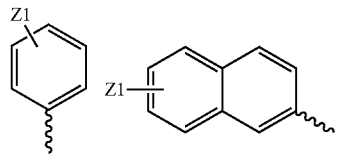

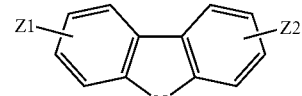

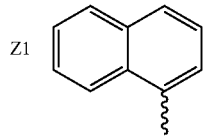

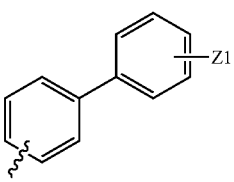
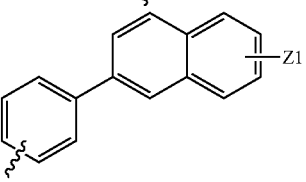

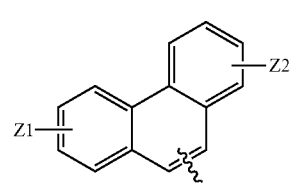

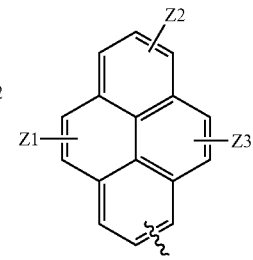

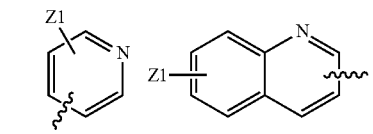

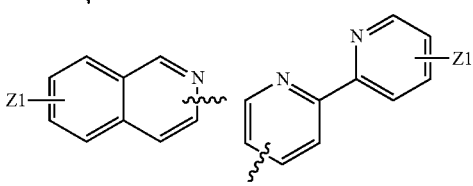

123
-continued

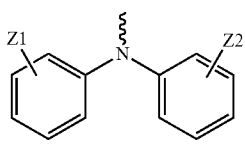

wherein Z1 to Z3 are the same as each other or different from each other, and may be selected from the group consisting of hydrogen; a halogen; an amino group; a nitrile group; a nitro group; a $C_1$~$C_{40}$ alkyl group; a $C_2$~$C_{40}$ alkenyl group; a $C_1$~$C_{40}$ alkoxy group; a $C_3$~$C_{40}$ cycloalkyl group; a $C_2$~$C_{40}$ heterocycloalkyl group; a $C_6$~$C_{40}$ arylamino group; a $C_6$~$C_{40}$ aryl group and a $C_2$~$C_{40}$ heteroaryl group.

7. The compound according to claim 1, wherein $L_1$ to $L_3$ are a direct bond or selected from the group consisting of the following Structural Formulas:

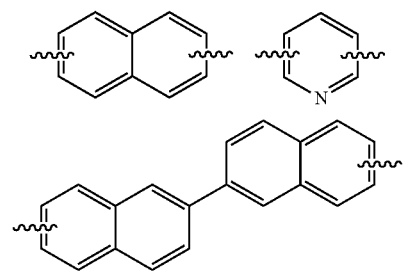

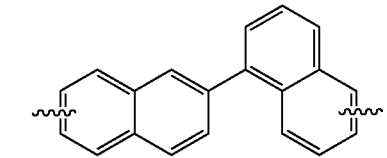

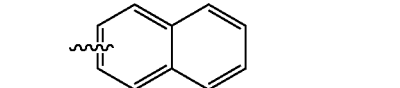

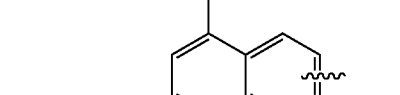

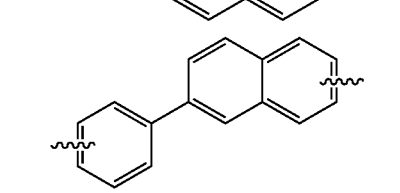

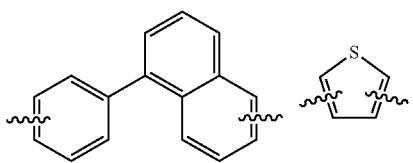

124
-continued

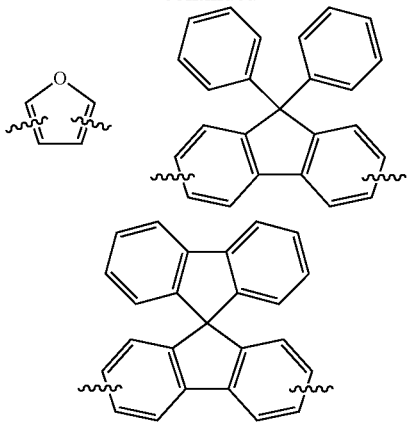

8. The compound according to claim 1, wherein the compound of Formula 1 is selected from the group consisting of the compounds that are represented by the following Formulas 1-1 to 1-120:

[Formula 1-1]

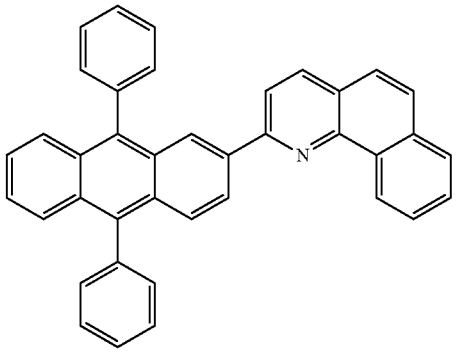

[Formula 1-2]

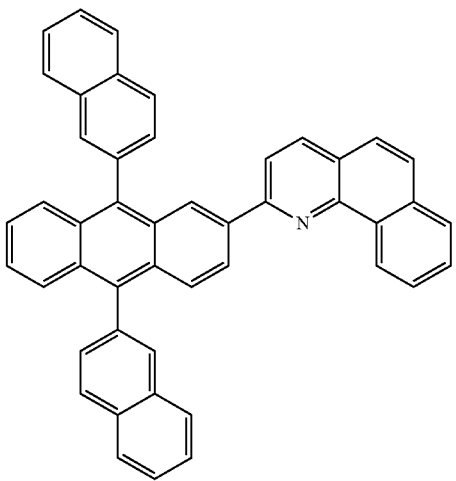

125
-continued
[Formula 1-3]
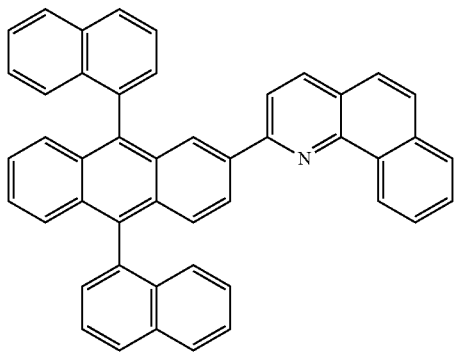
[Formula 1-4]
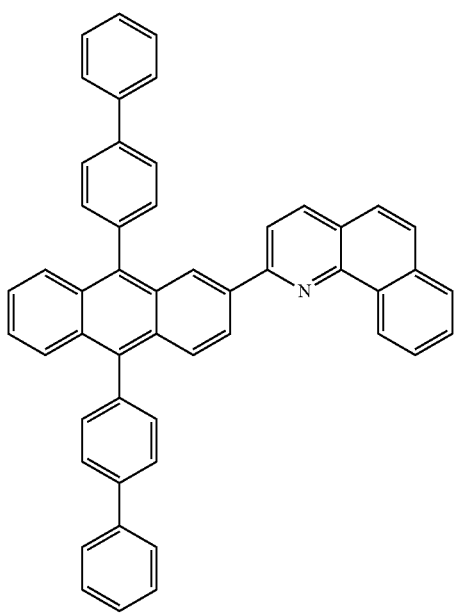
[Formula 1-5]
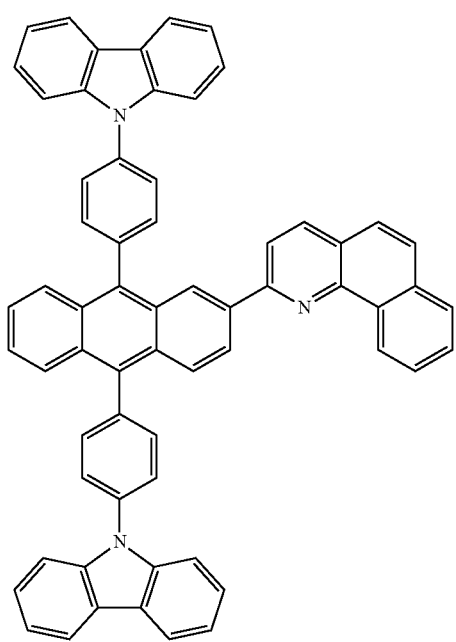
126
-continued
[Formula 1-6]
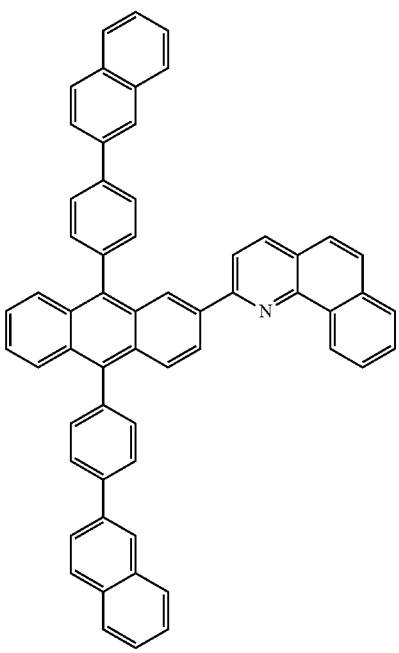
[Formula 1-7]
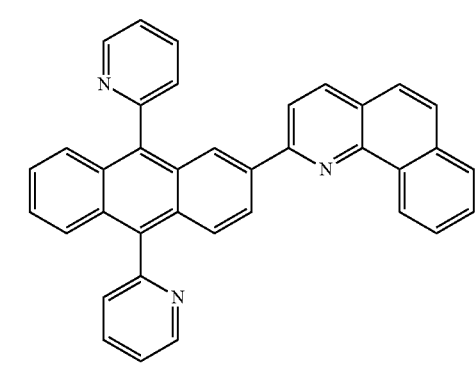
[Formula 1-8]

[Formula 1-9]
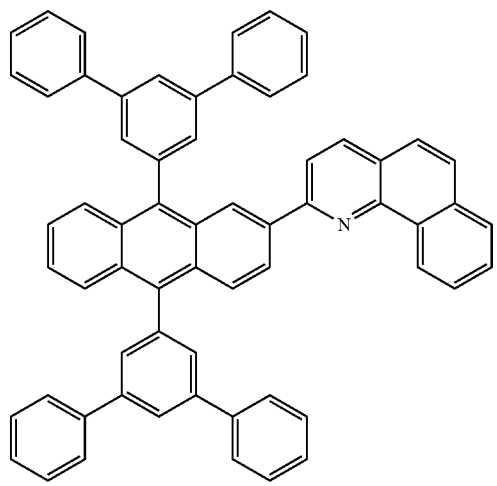
[Formula 1-10]
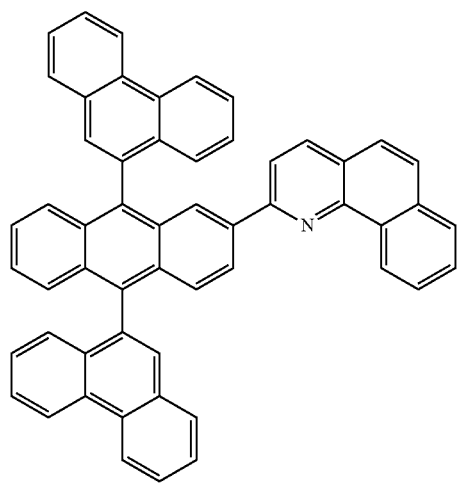
[Formula 1-11]
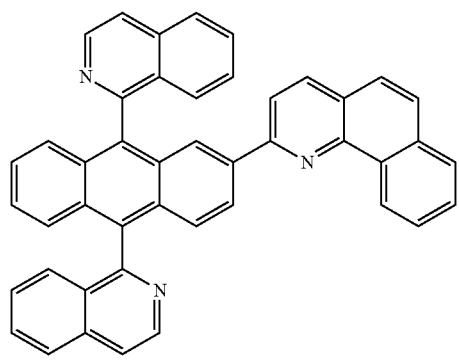
[Formula 1-12]
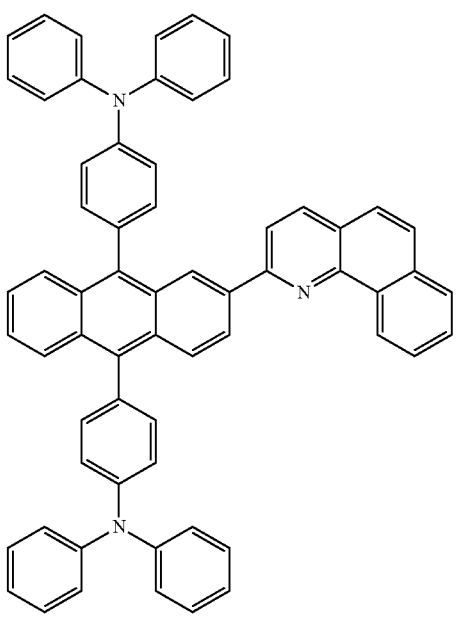
[Formula 1-13]
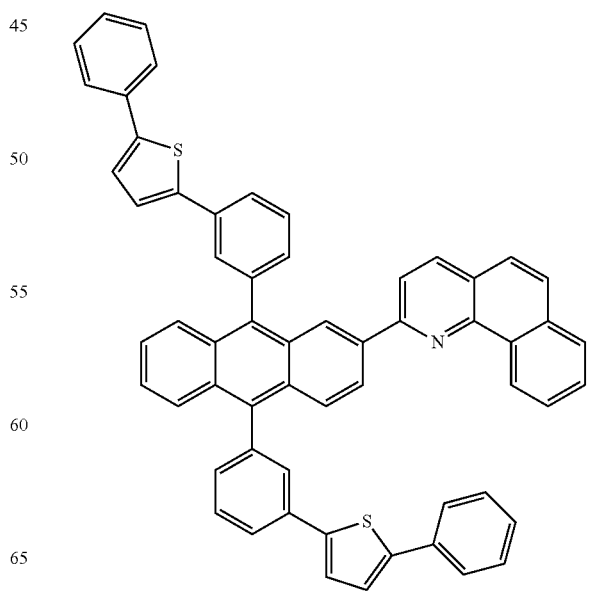

[Formula 1-14]
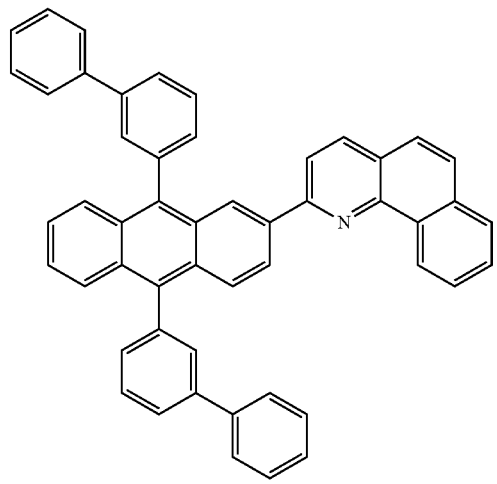
[Formula 1-17]
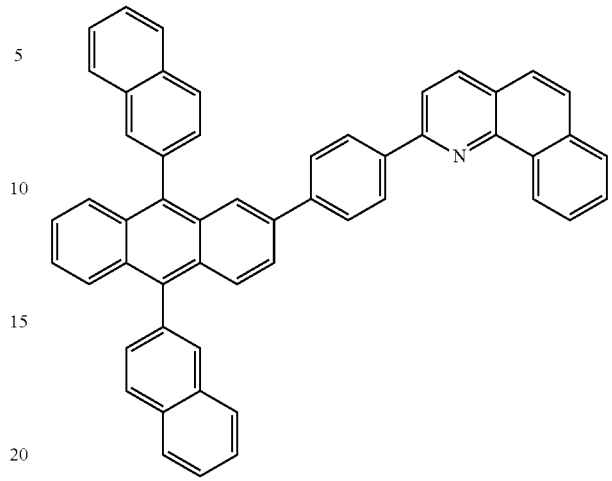
[Formula 1-15]
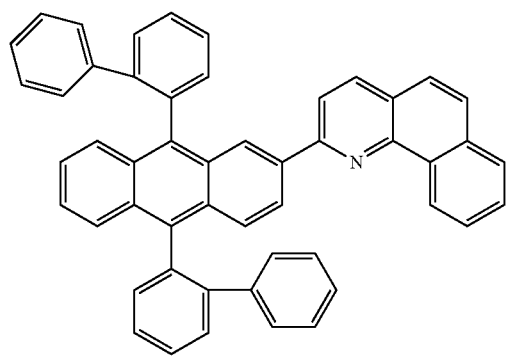
[Formula 1-18]
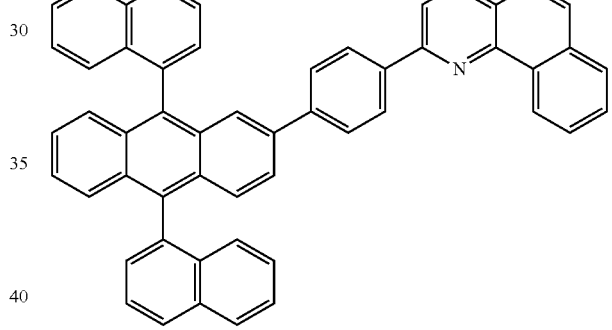
[Formula 1-16]
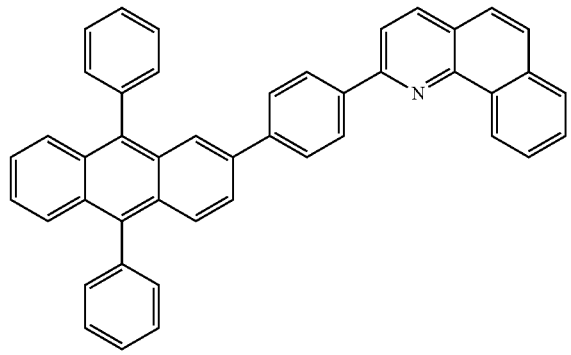
[Formula 1-19]
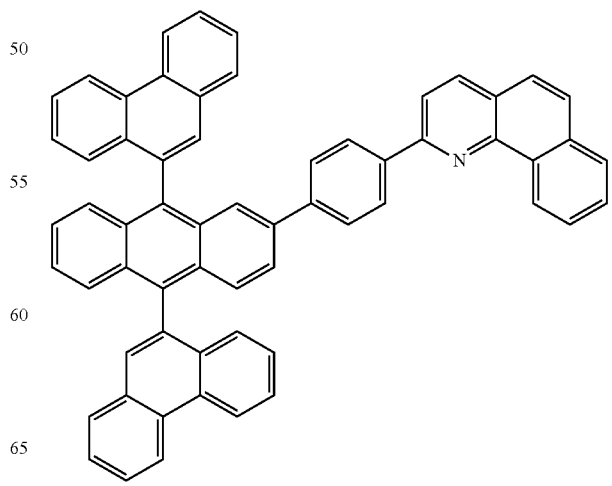

[Formula 1-20]
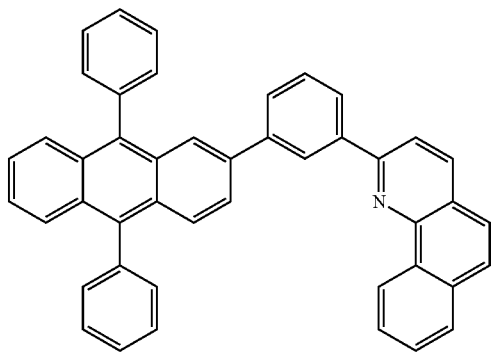
[Formula 1-21]
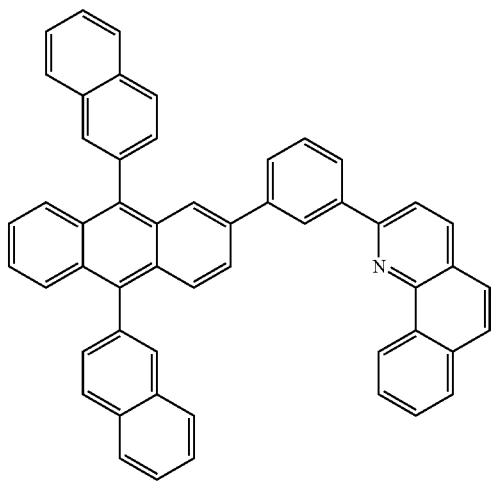
[Formula 1-22]
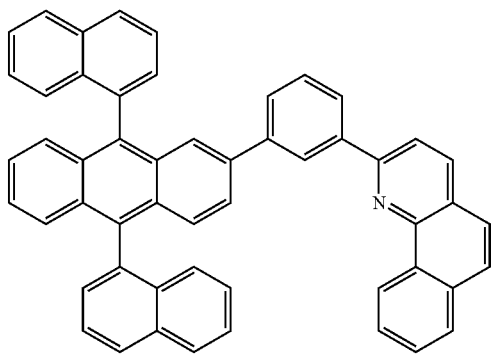
[Formula 1-23]
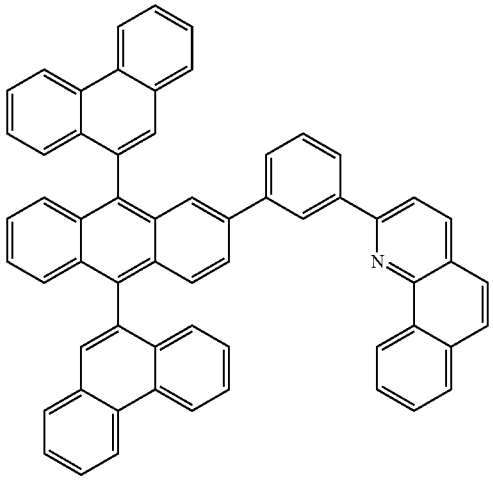
[Formula 1-24]
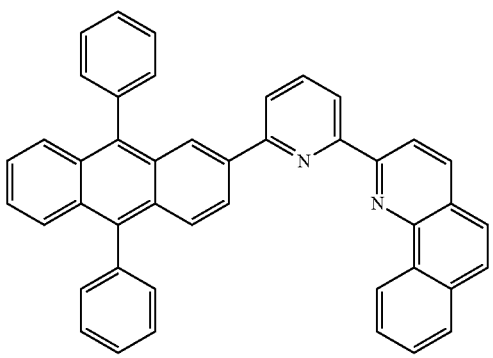
[Formula 1-25]
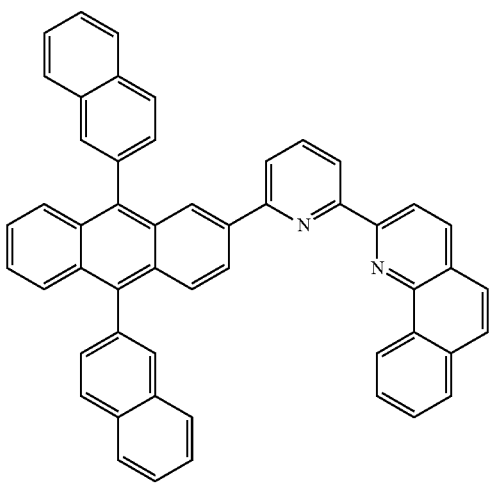

[Formula 1-26]
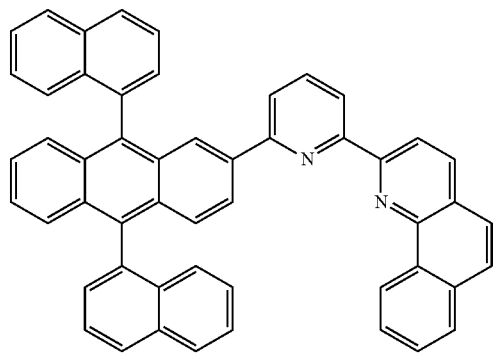
[Formula 1-27]
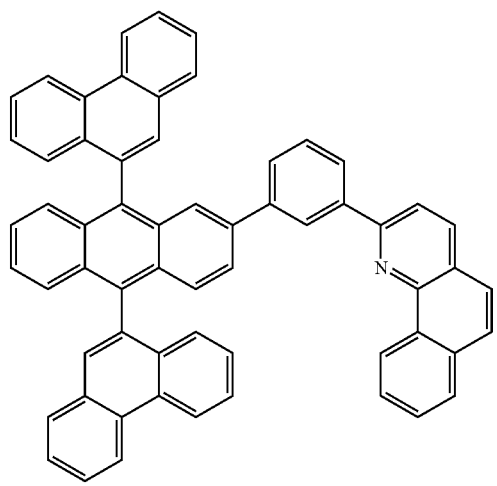
[Formula 1-28]
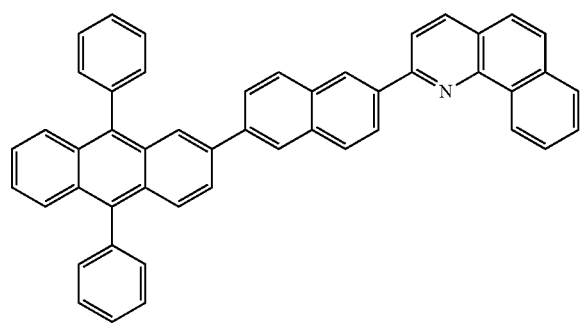
[Formula 1-29]
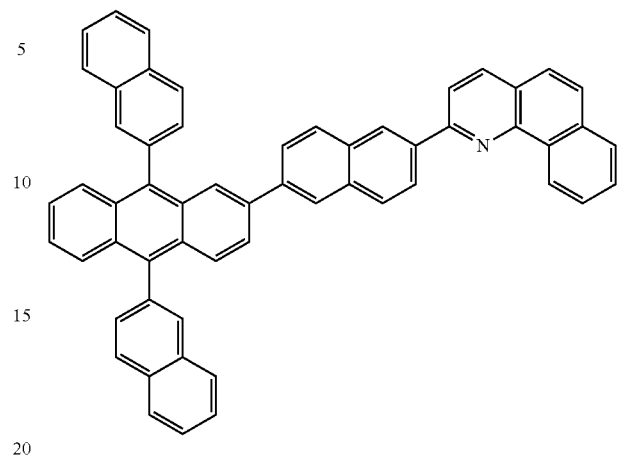
[Formula 1-30]
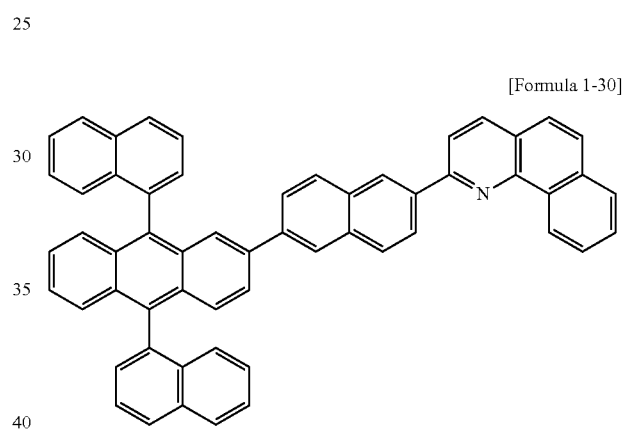
[Formula 1-31]
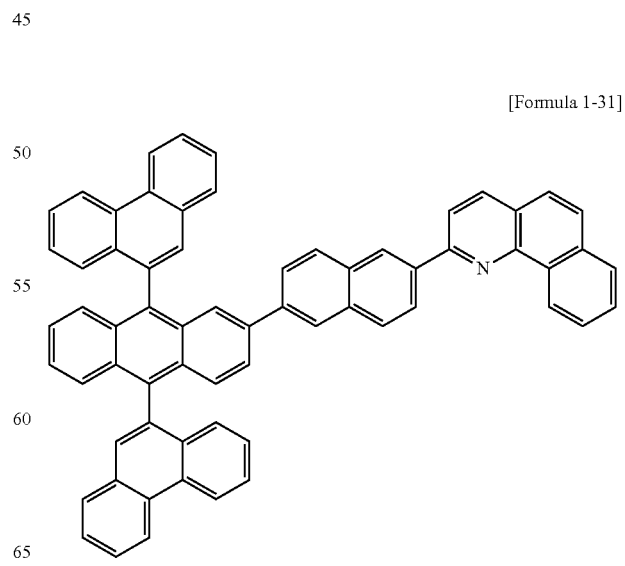

[Formula 1-32]
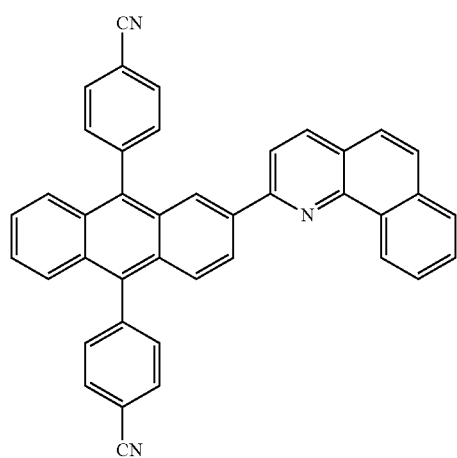
[Formula 1-33]
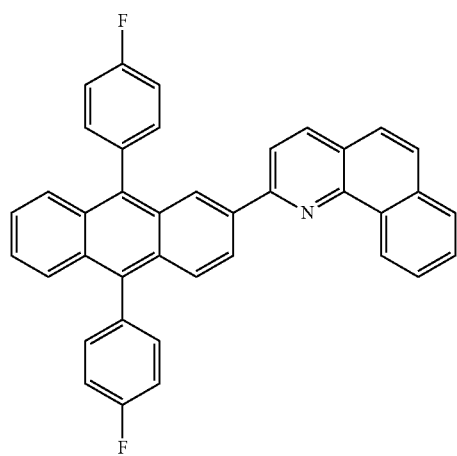
[Formula 1-34]
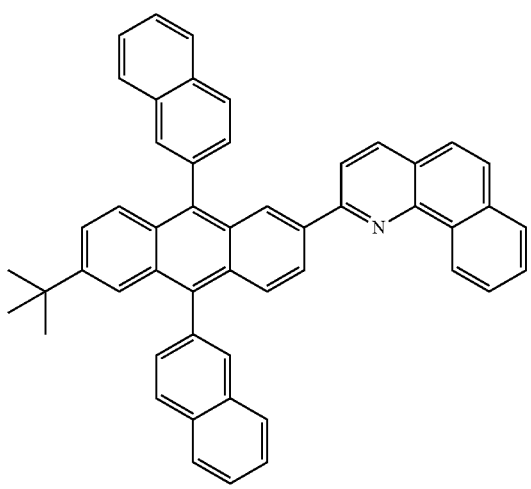
[Formula 1-35]
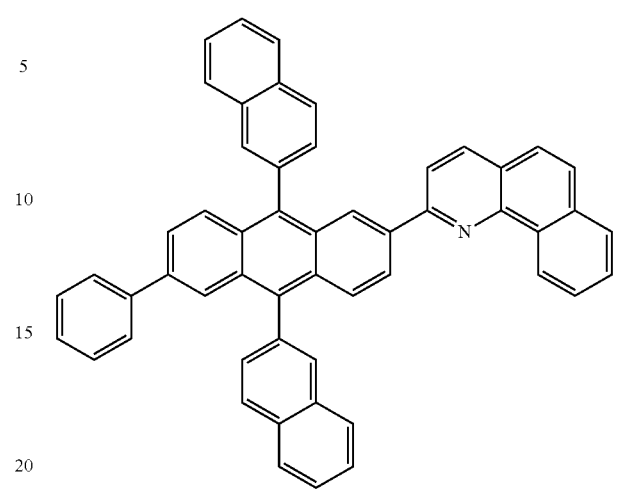
[Formula 1-36]
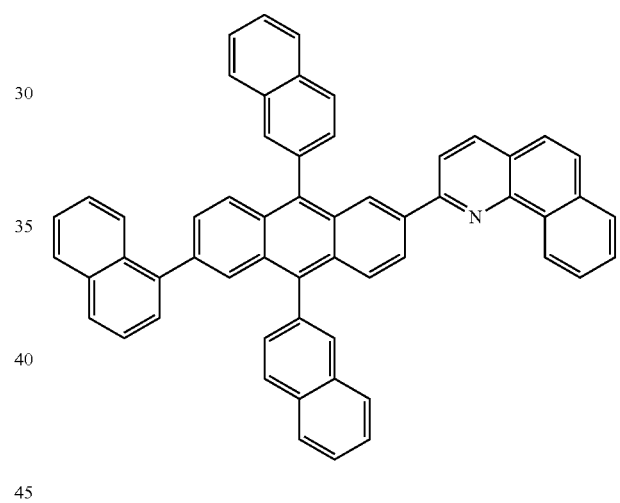
[Formula 1-37]
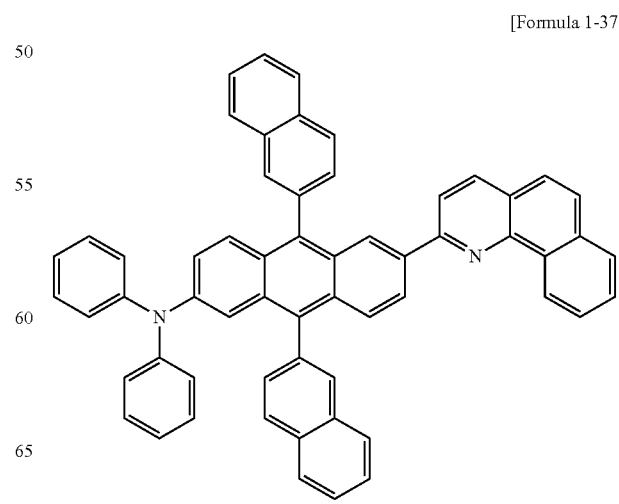

[Formula 1-38]
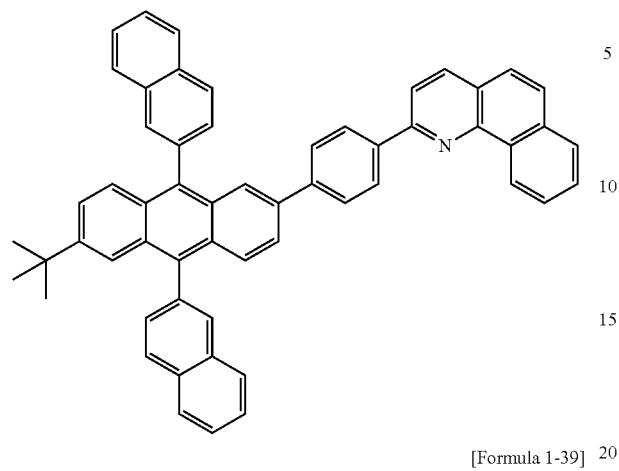
[Formula 1-39]
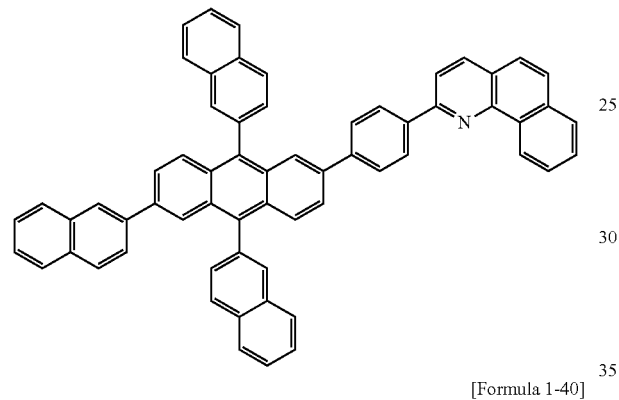
[Formula 1-40]
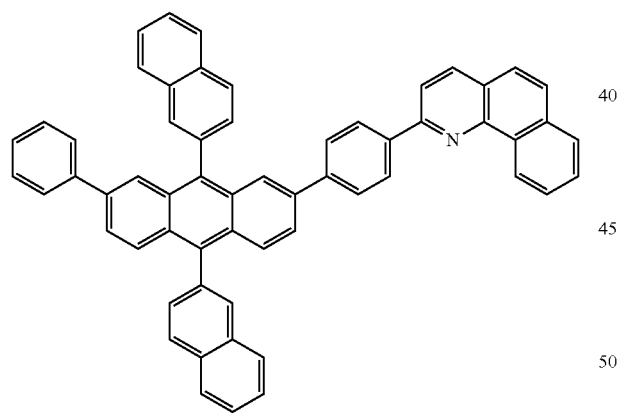
[Formula 1-41]
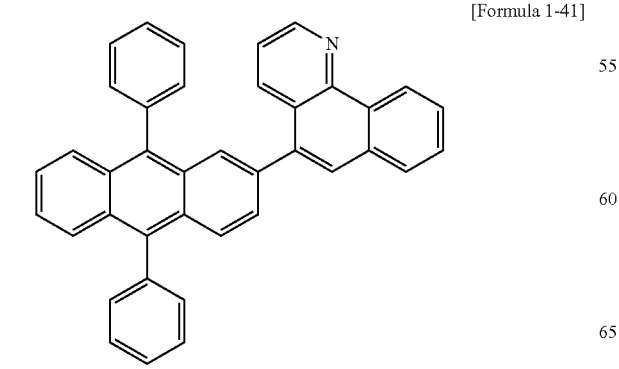
[Formula 1-42]
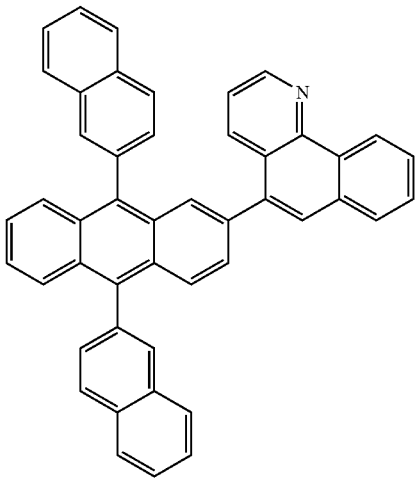
[Formula 1-43]
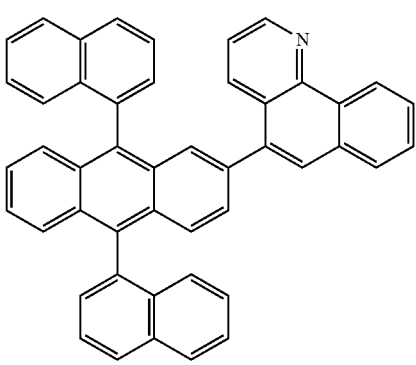
[Formula 1-44]
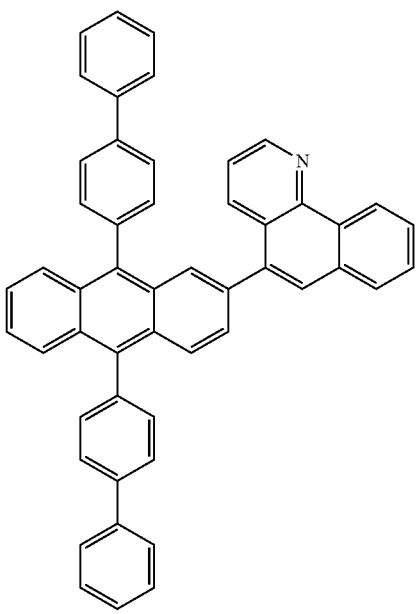

[Formula 1-45]
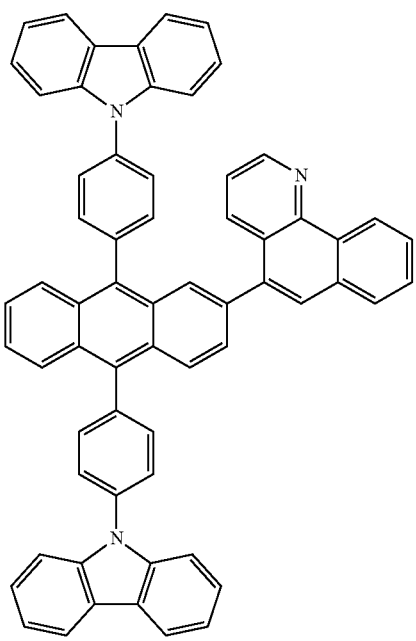
[Formula 1-46]
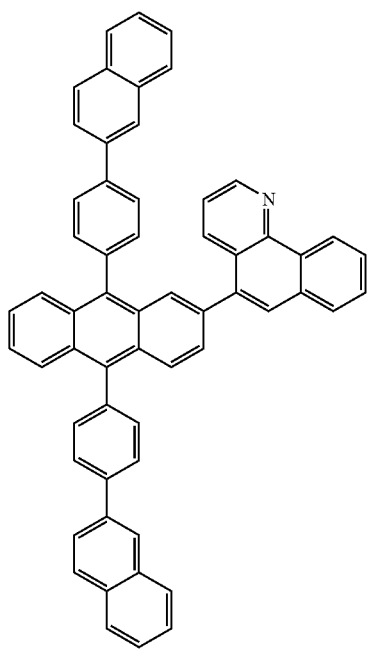
[Formula 1-47]
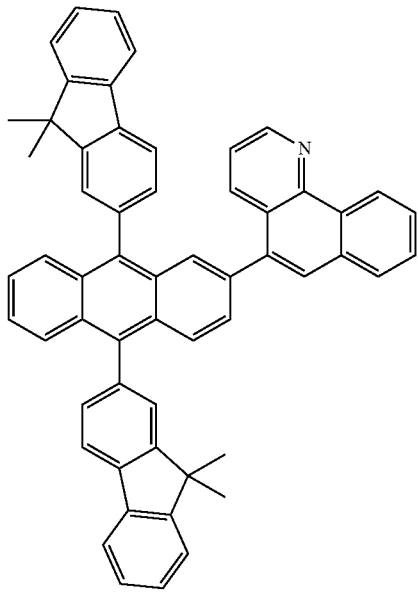
[Formula 1-48]
[Formula 1-49]

[Formula 1-50]
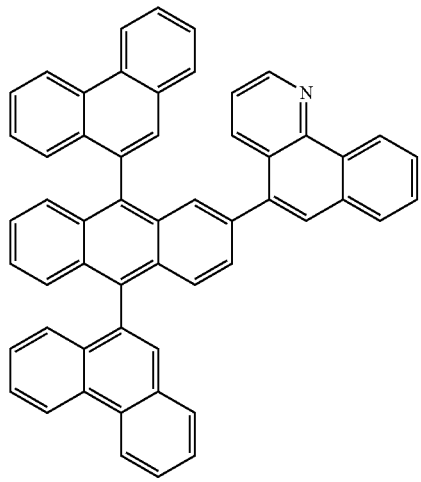
[Formula 1-51]
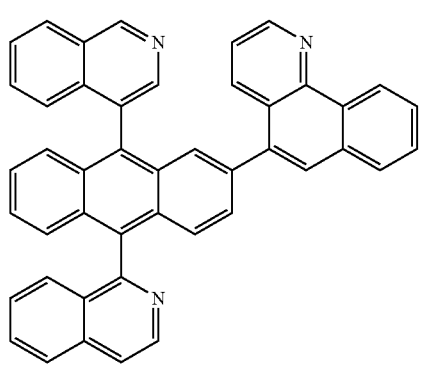
[Formula 1-52]
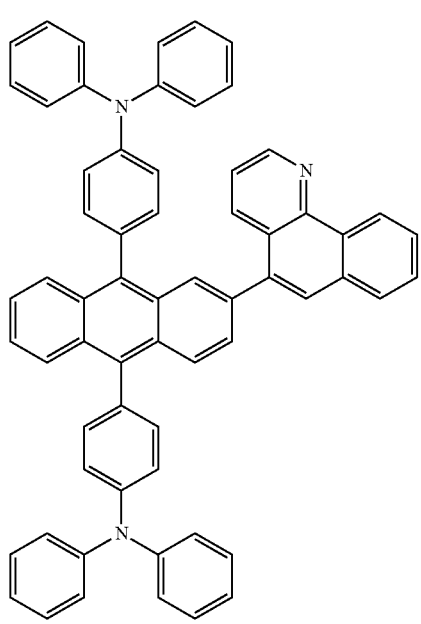
[Formula 1-53]
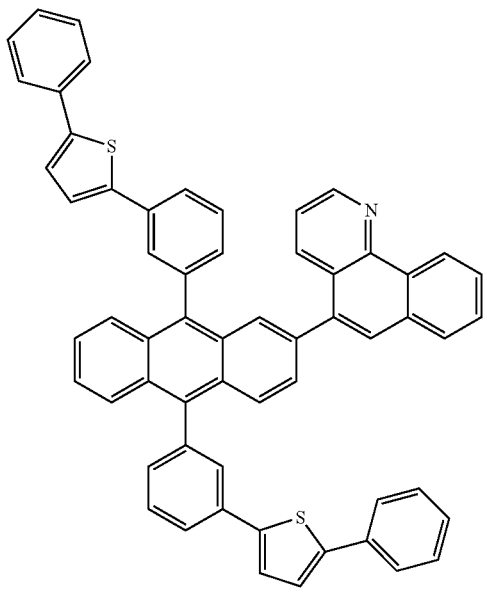
[Formula 1-54]
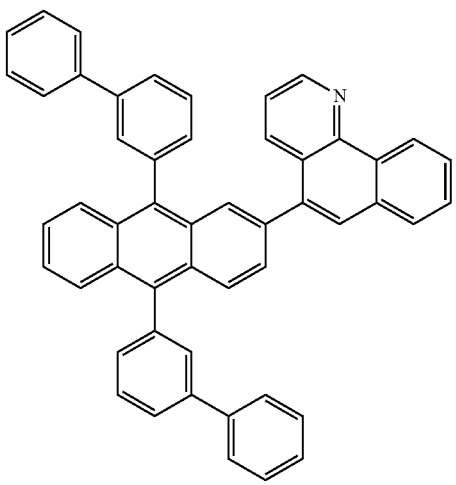
[Formula 1-55]
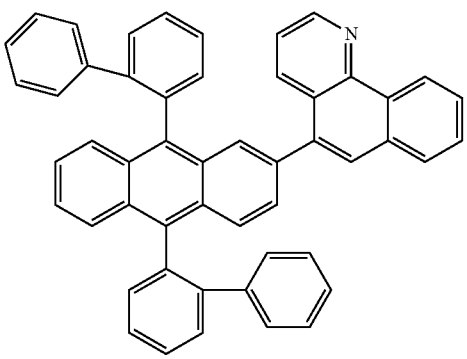

[Formula 1-56]
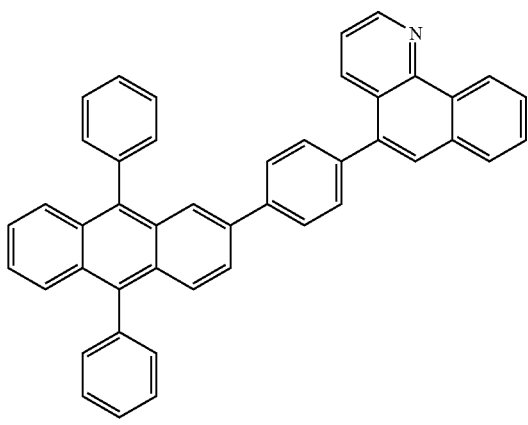
[Formula 1-57]
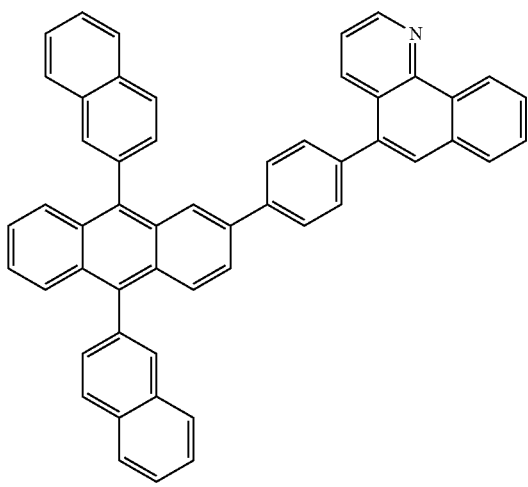
[Formula 1-58]
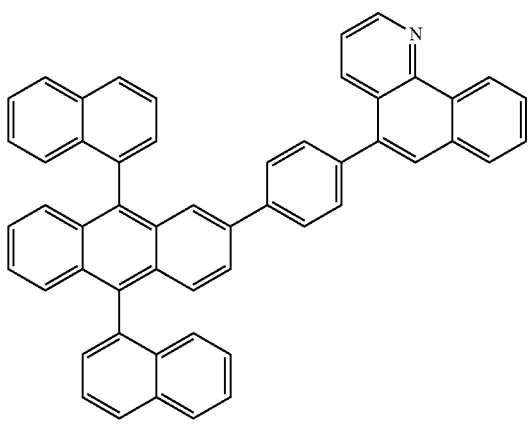
[Formula 1-59]
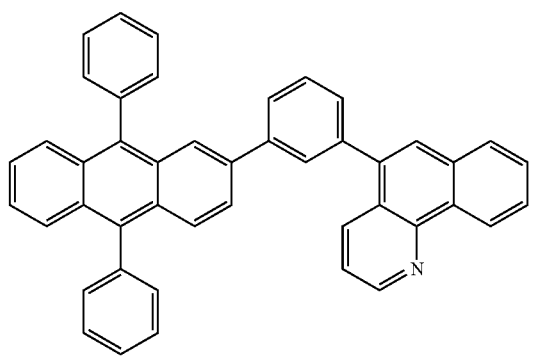
[Formula 1-60]
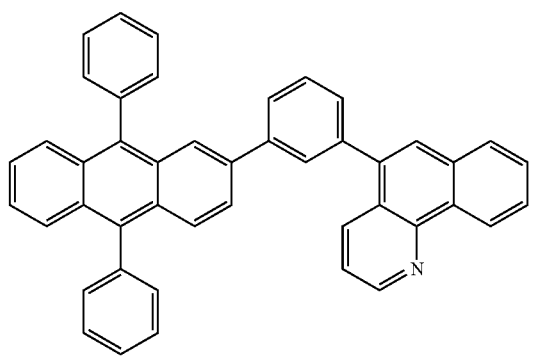
[Formula 1-61]
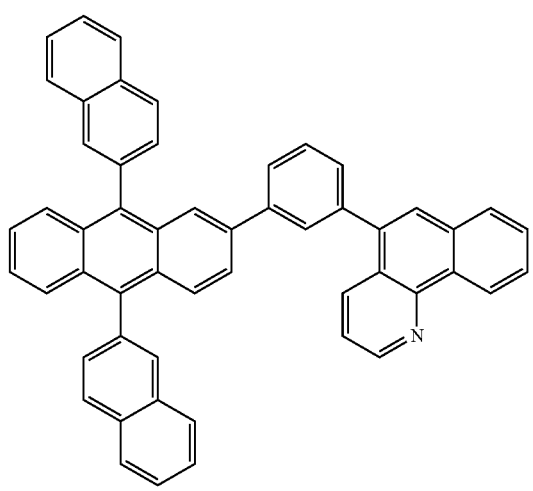

[Formula 1-62]
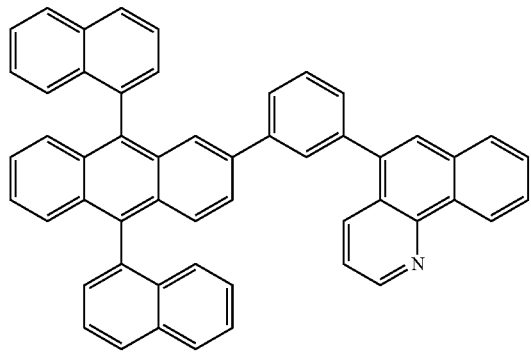
[Formula 1-65]
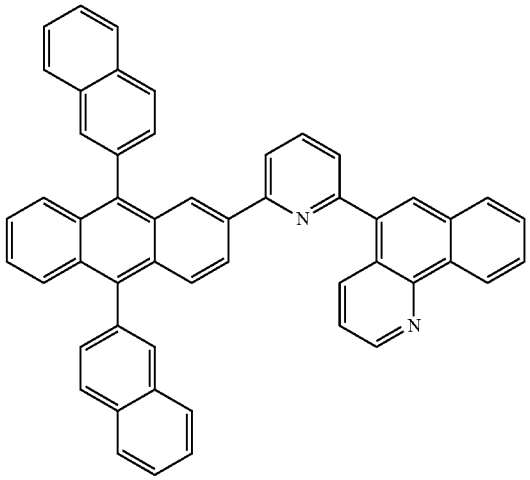
[Formula 1-63]
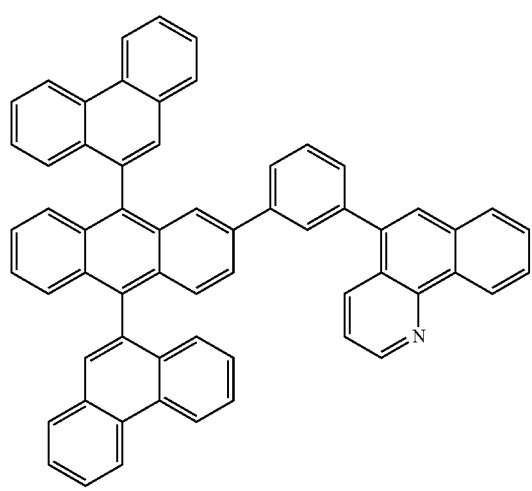
[Formula 1-66]
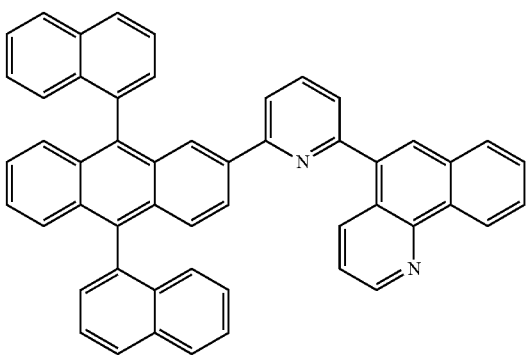
[Formula 1-64]
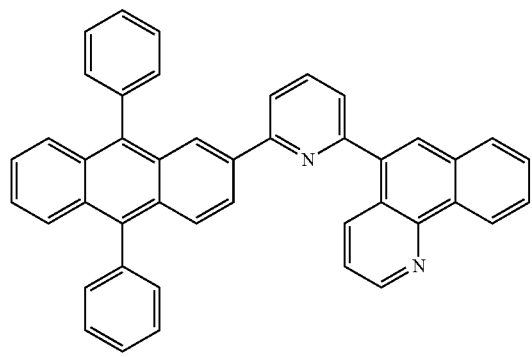
[Formula 1-67]
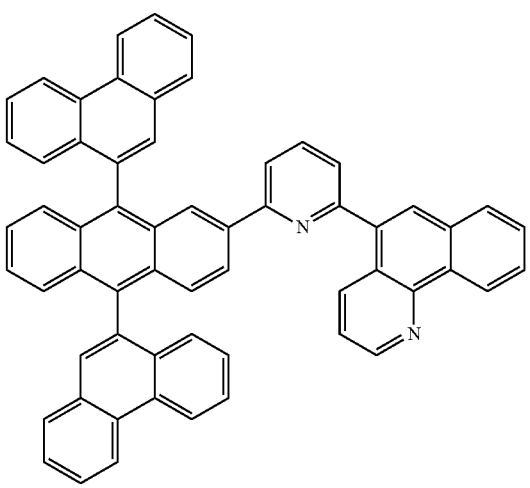

[Formula 1-68]
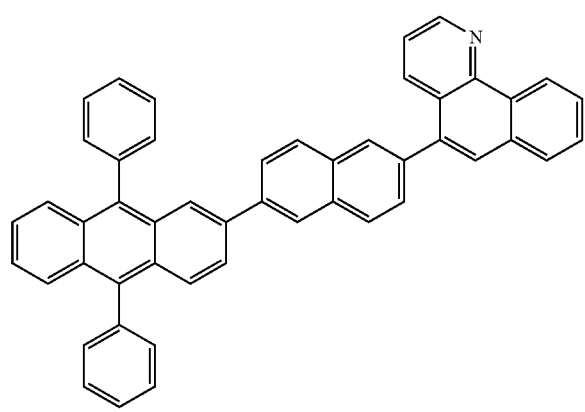
[Formula 1-69]
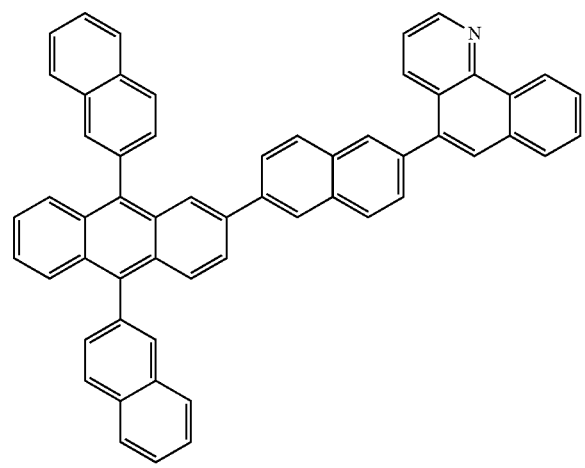
[Formula 1-70]
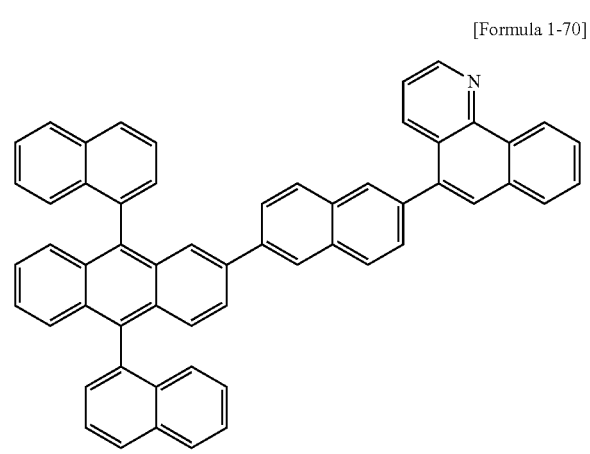
[Formula 1-71]
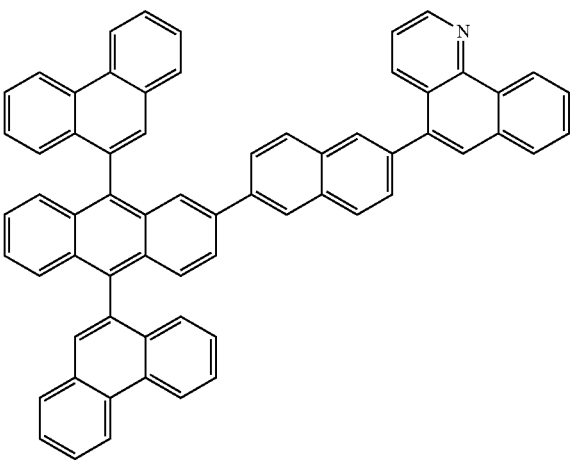
[Formula 1-72]
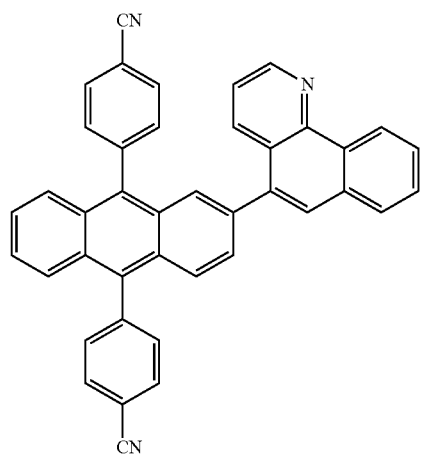
[Formula 1-73]
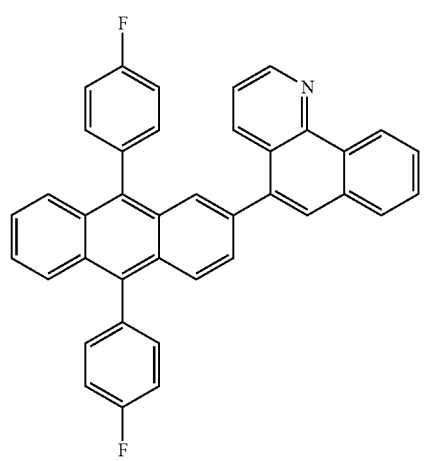

[Formula 1-74]
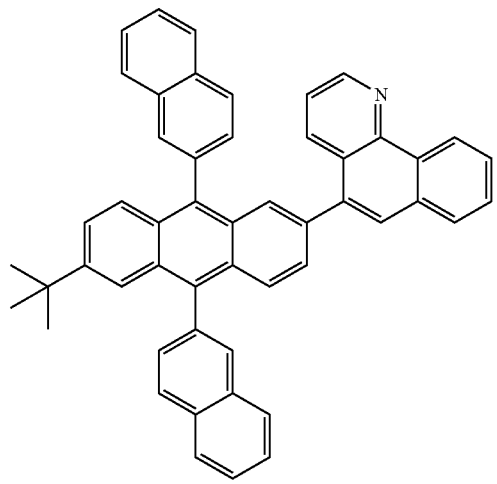
[Formula 1-77]
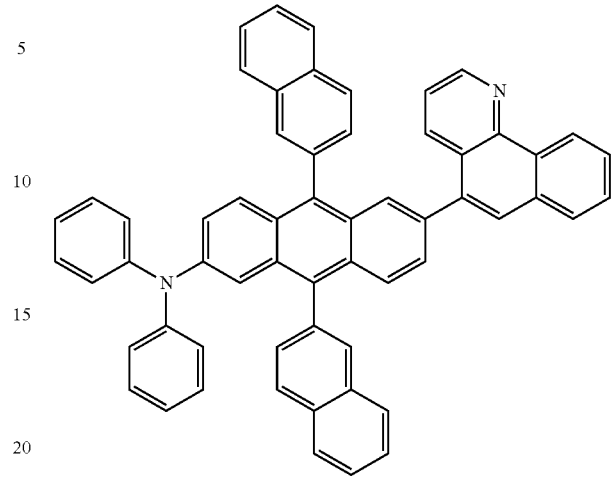
[Formula 1-75]
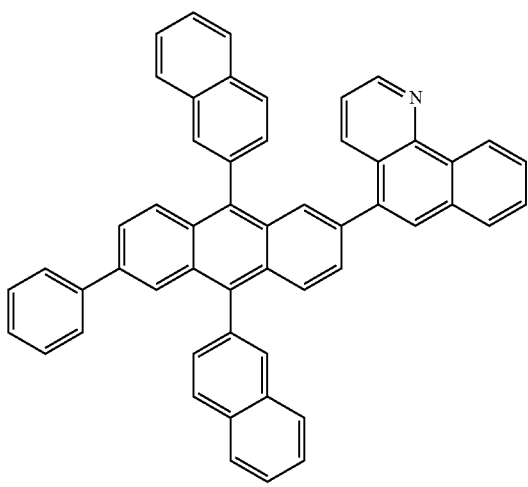
[Formula 1-78]
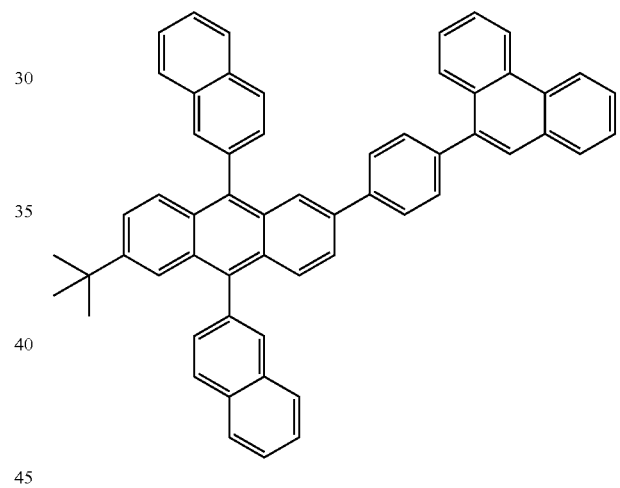
[Formula 1-76]
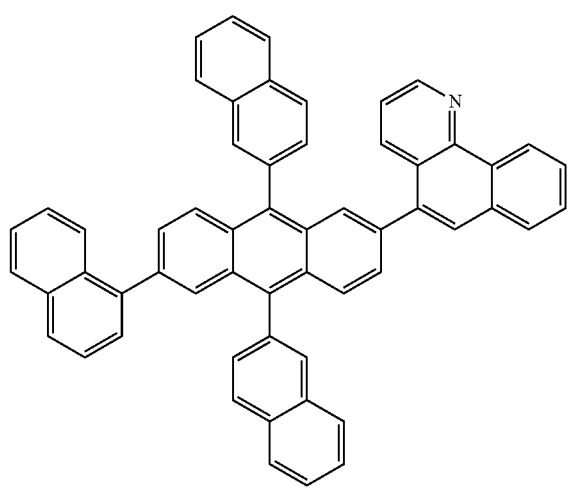
[Formula 1-79]
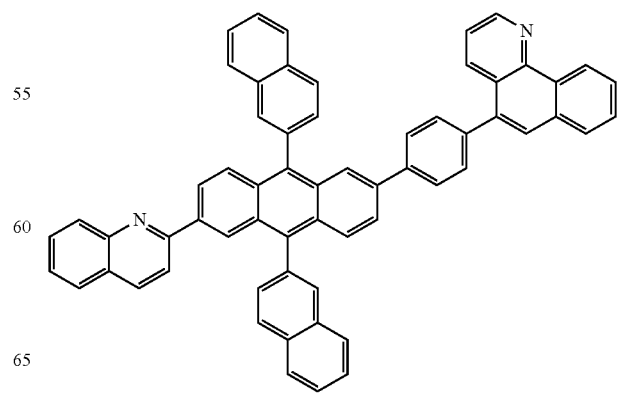

[Formula 1-80]
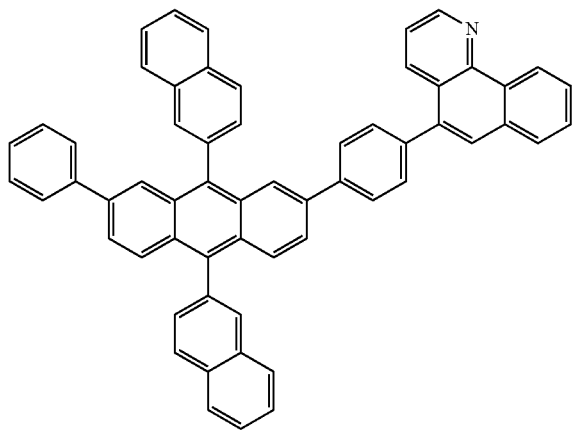
[Formula 1-81]
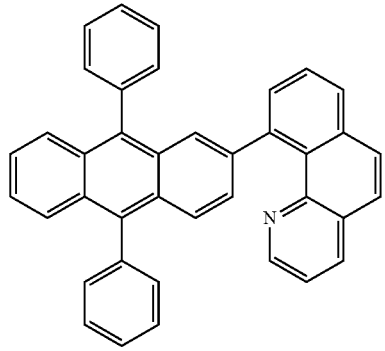
[Formula 1-82]
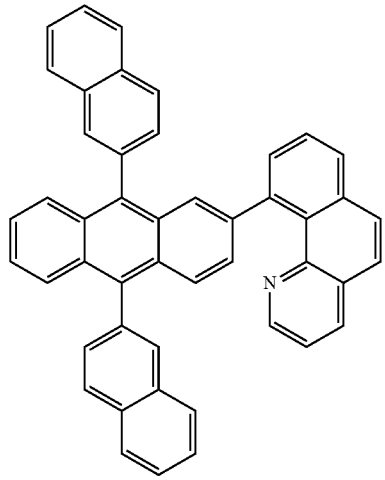
[Formula 1-83]
[Formula 1-84]
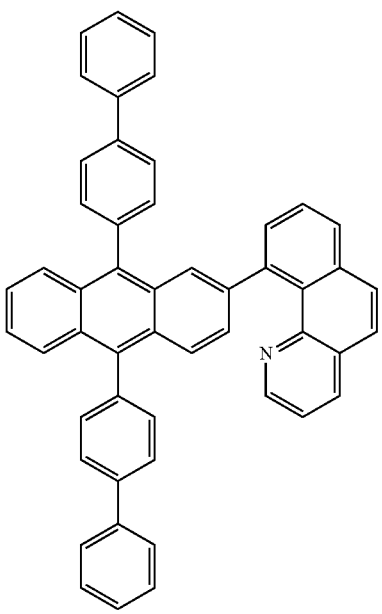
[Formula 1-85]
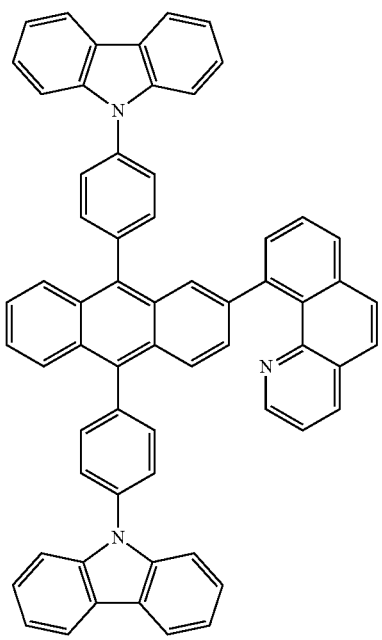

[Formula 1-86]
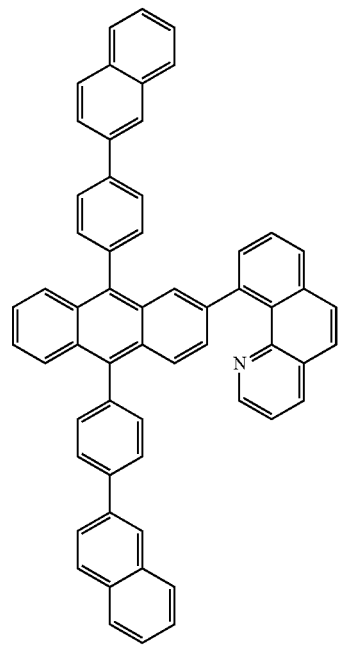
[Formula 1-87]
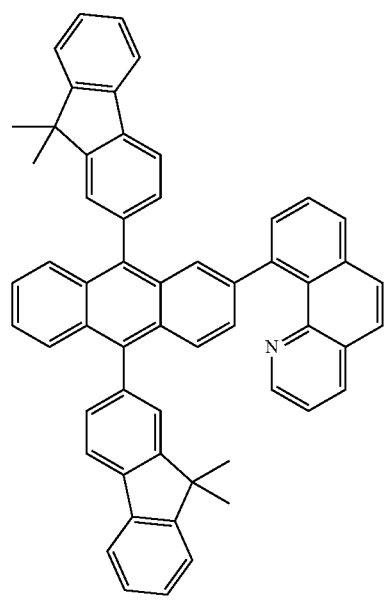
[Formula 1-88]
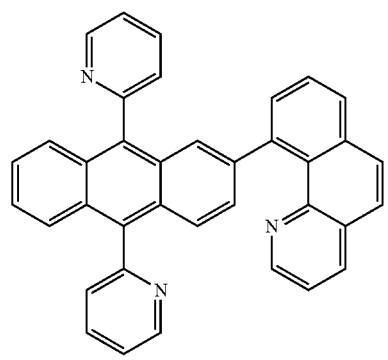
[Formula 1-89]
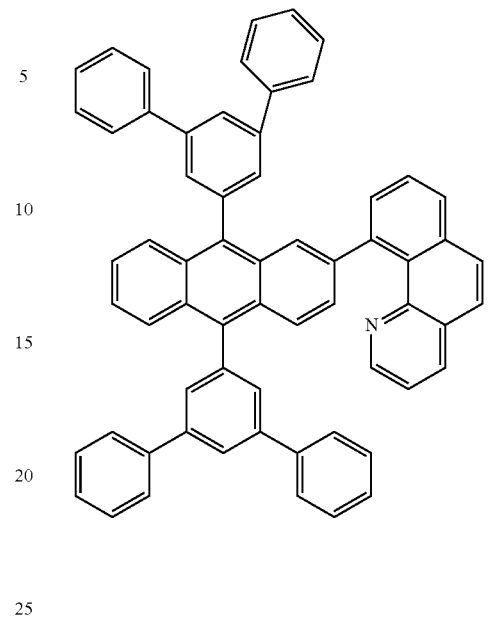
[Formula 1-90]
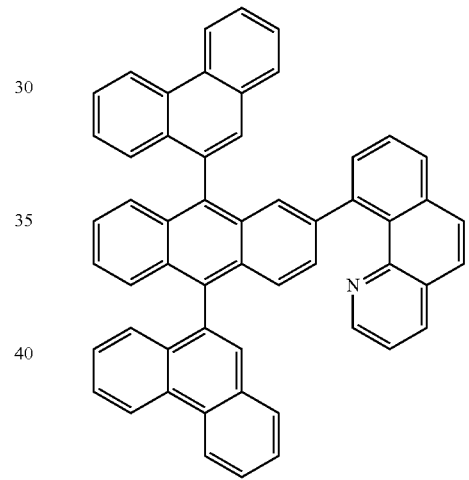
[Formula 1-91]
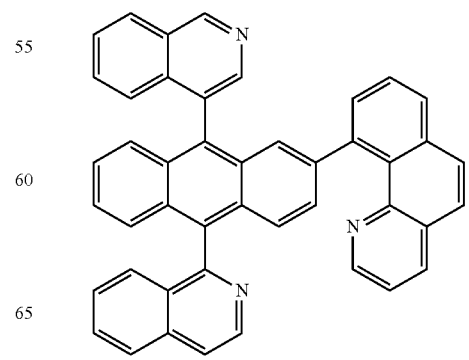

[Formula 1-92]
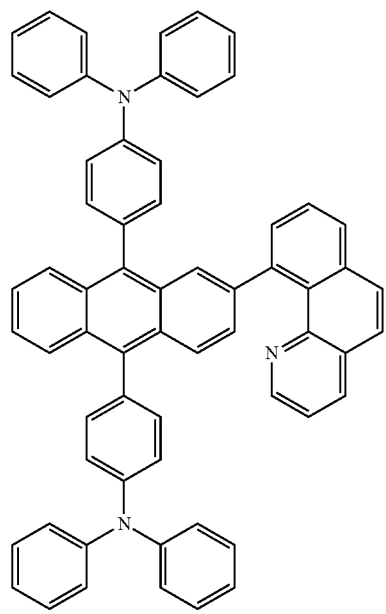
[Formula 1-93]
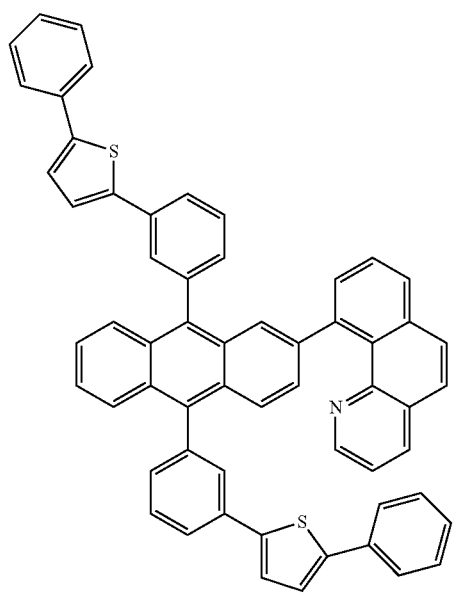
[Formula 1-94]
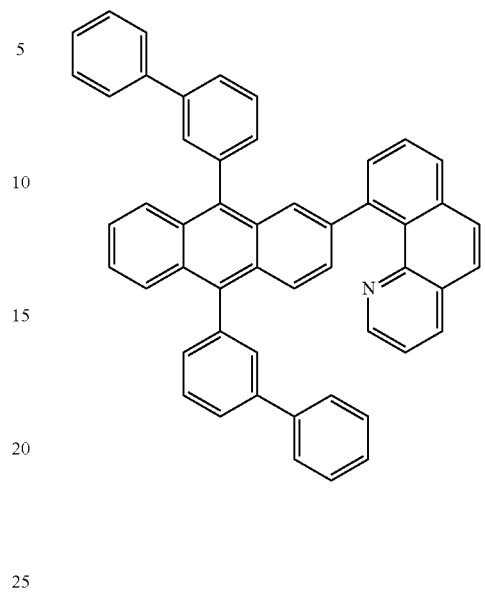
[Formula 1-95]
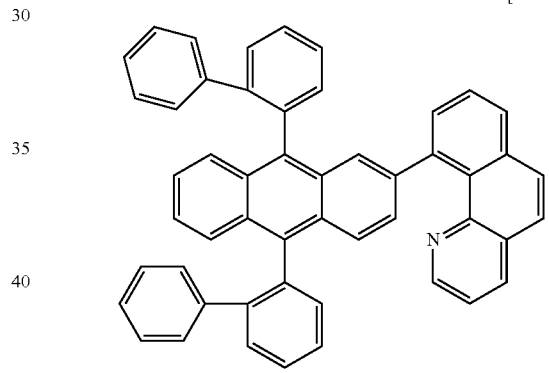
[Formula 1-96]
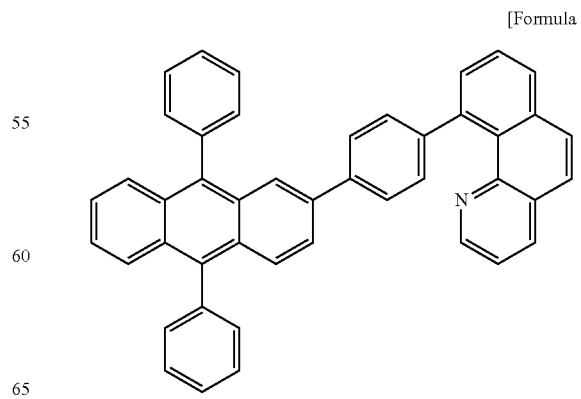

[Formula 1-97]
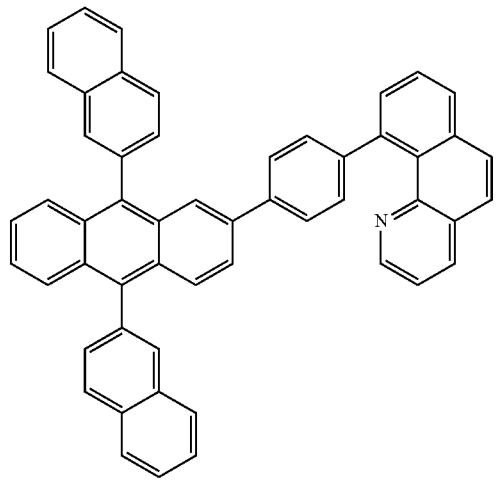
[Formula 1-98]
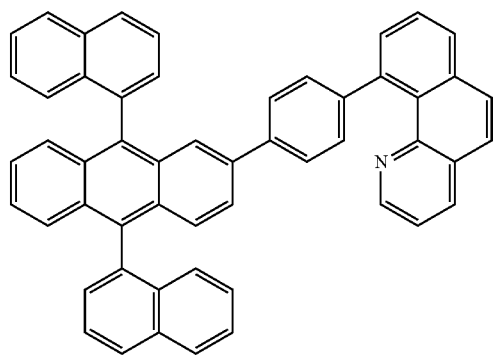
[Formula 1-99]
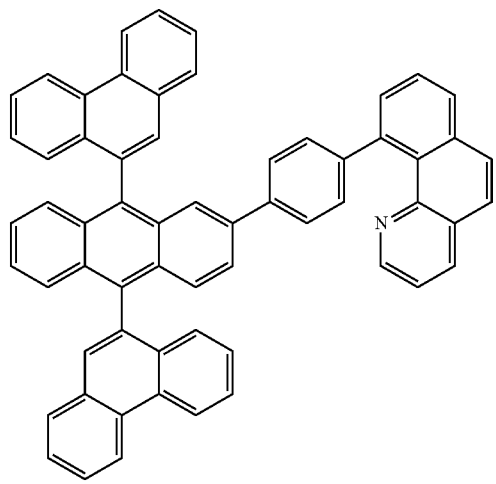
[Formula 1-100]
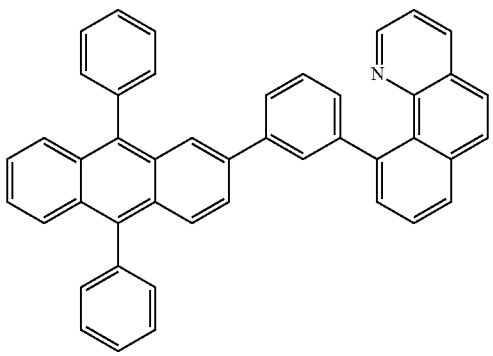
[Formula 1-101]
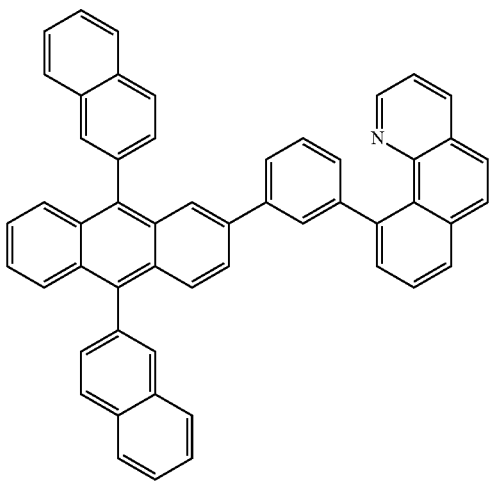
[Formula 1-102]
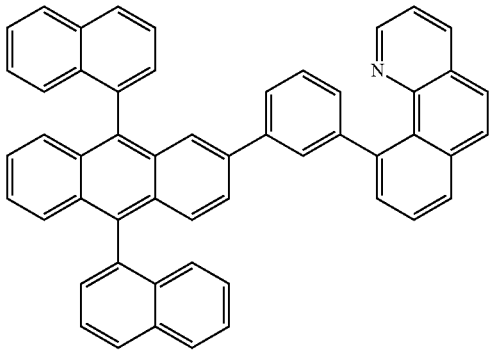

[Formula 1-103]
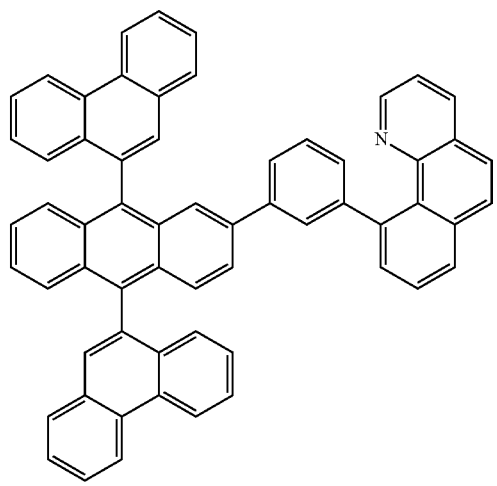
[Formula 1-104]
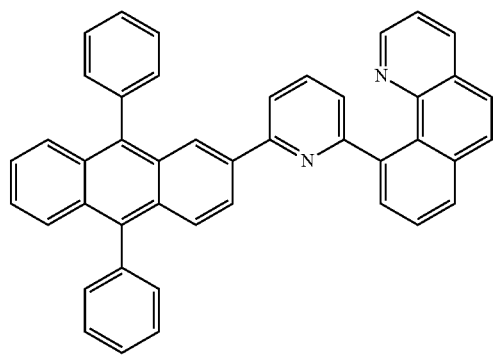
[Formula 1-105]
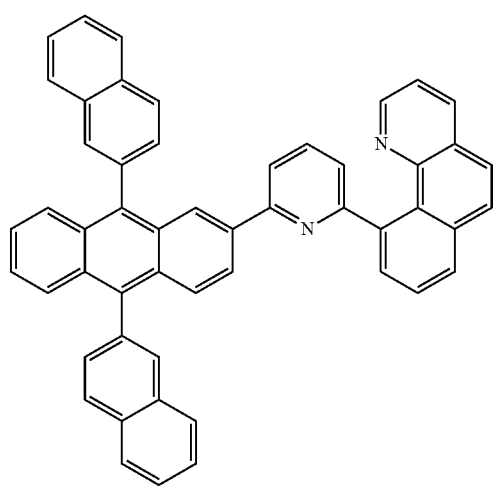
[Formula 1-106]
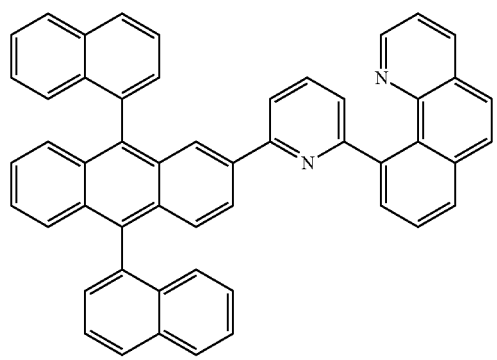
[Formula 1-107]
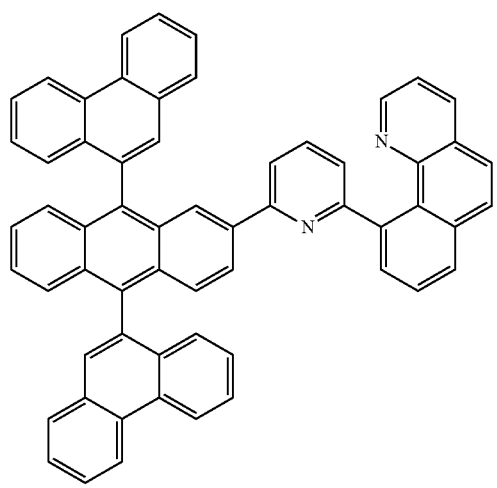
[Formula 1-108]
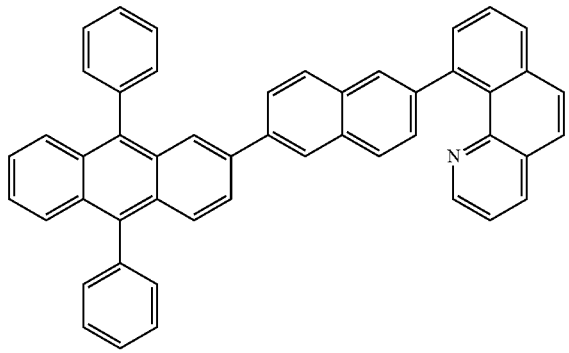

[Formula 1-109]
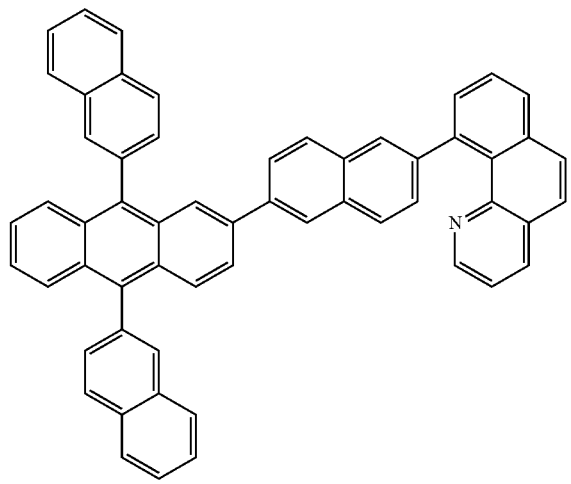
[Formula 1-110]
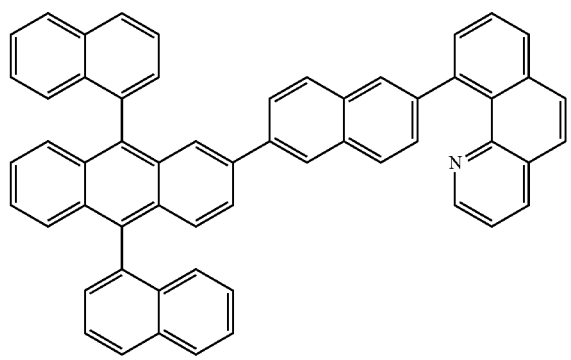
[Formula 1-111]
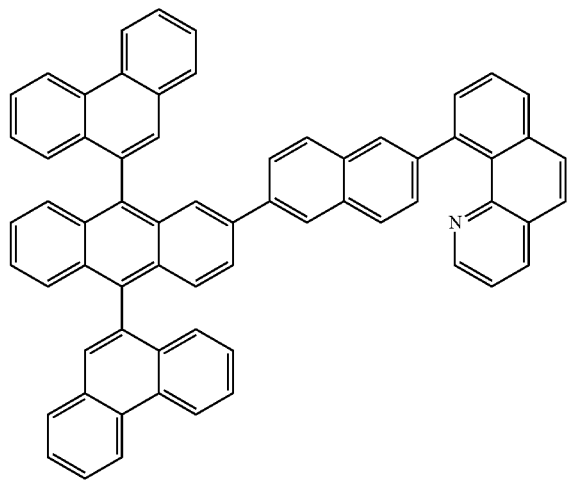
[Formula 1-112]
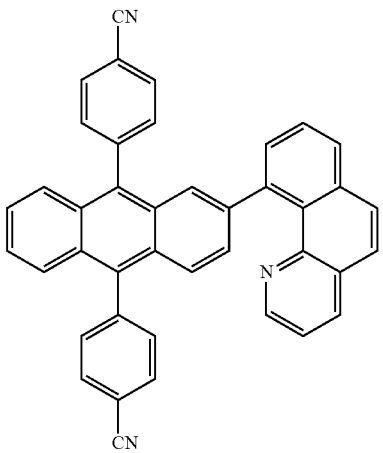
[Formula 1-113]
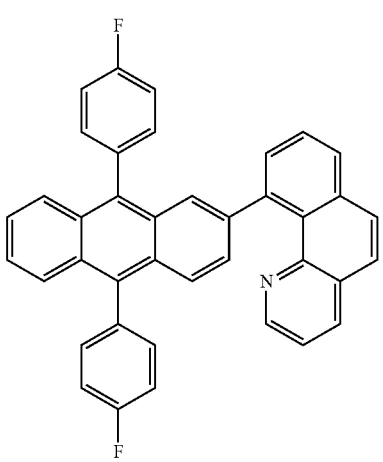
[Formula 1-114]
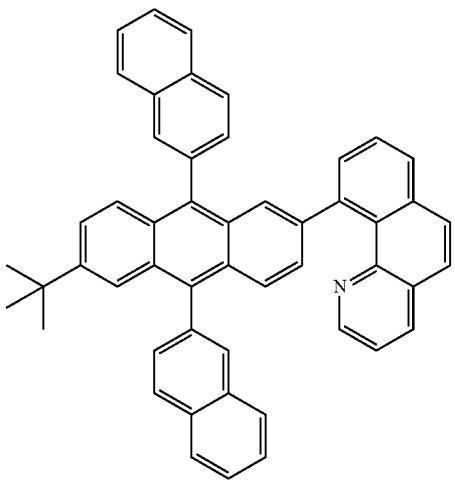

163
-continued
[Formula 1-115]
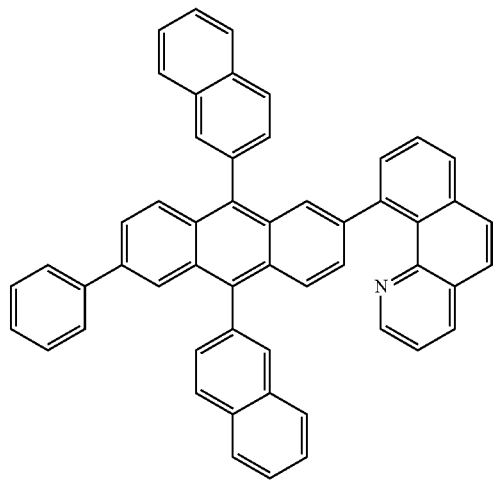
[Formula 1-116]
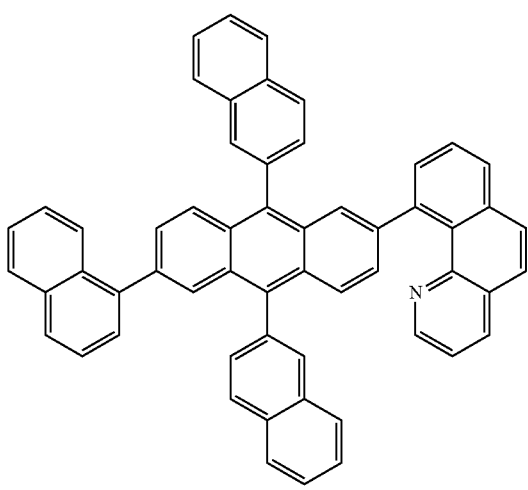
[Formula 1-117]
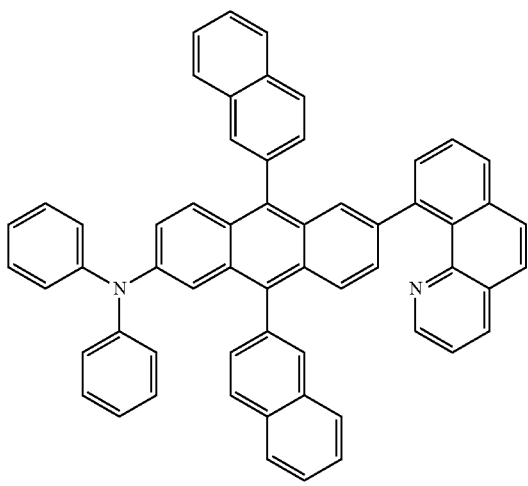
164
-continued
[Formula 1-118]
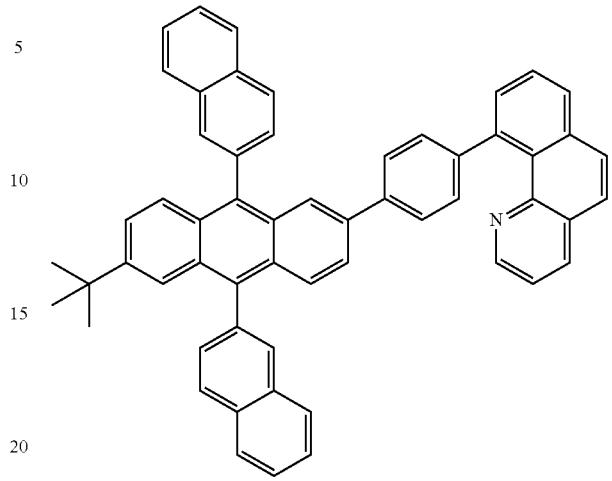
[Formula 1-119]
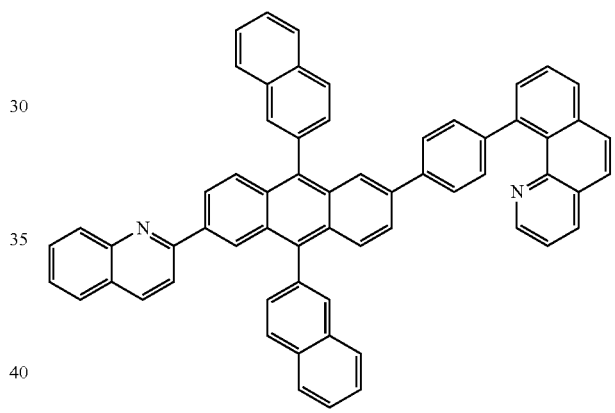
[Formula 1-120]
9. The compound according to claim 1, wherein the compound of Formula 1 is selected from the group consisting of the compounds that are represented by the following Formulas 2-1 to 2-40:

[Formula 2-1]
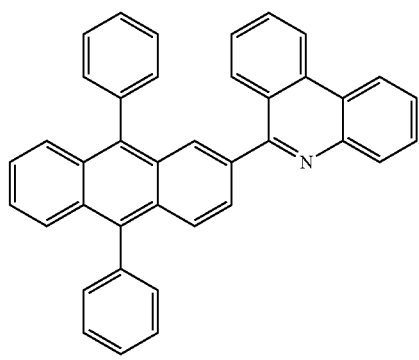
[Formula 2-2]
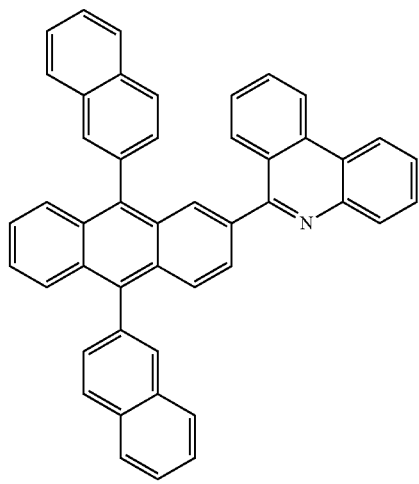
[Formula 2-3]
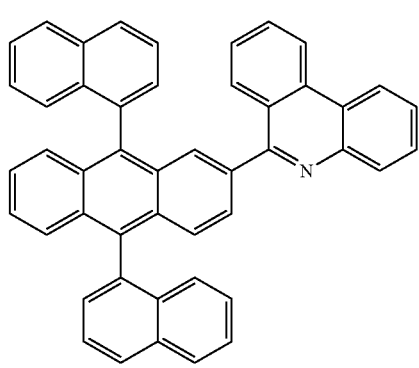
[Formula 2-4]
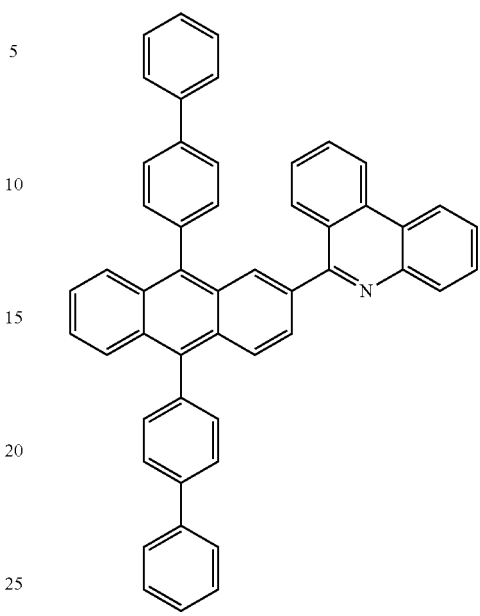
[Formula 2-5]

[Formula 2-6]
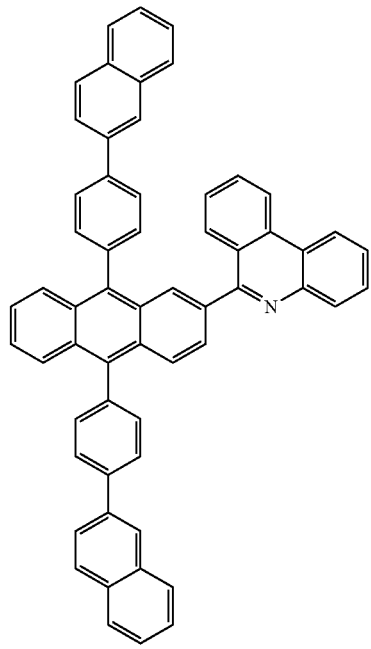
[Formula 2-9]
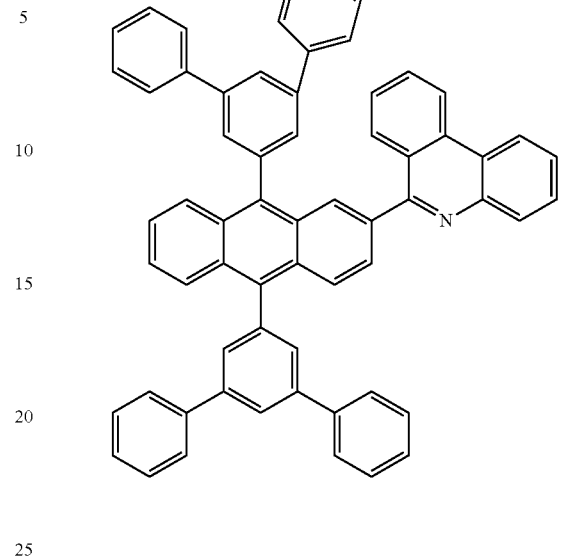
[Formula 2-7]
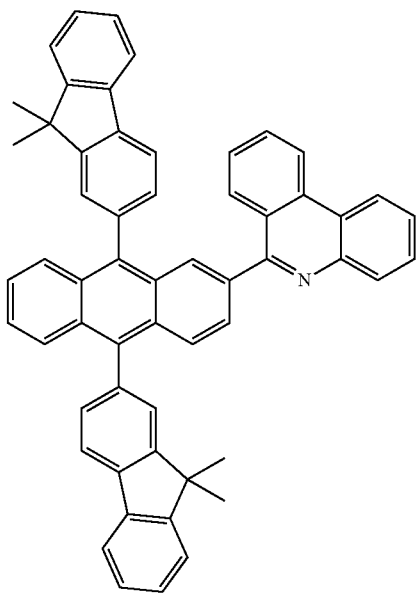
[Formula 2-10]
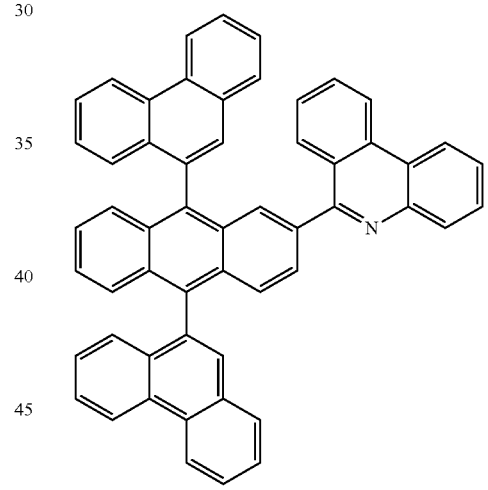
[Formula 2-8]
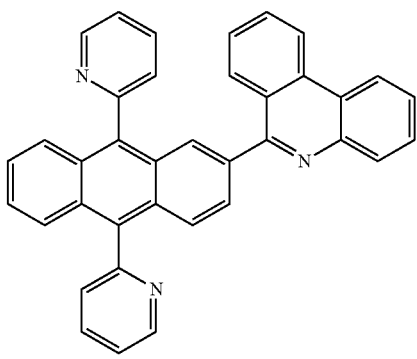
[Formula 2-11]
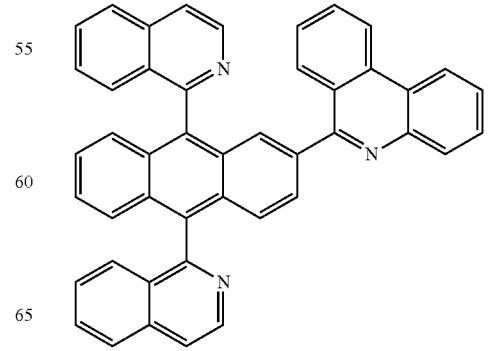

[Formula 2-12]
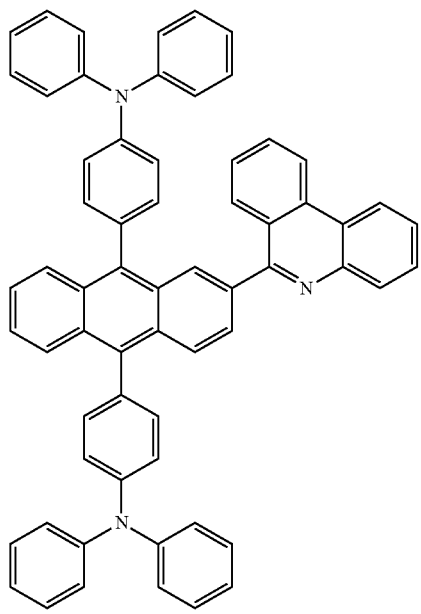
[Formula 2-14]
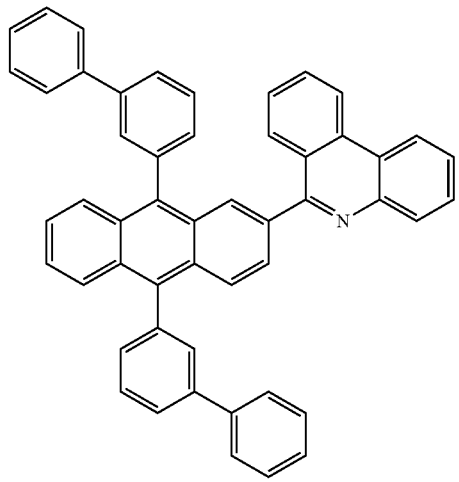
[Formula 2-15]
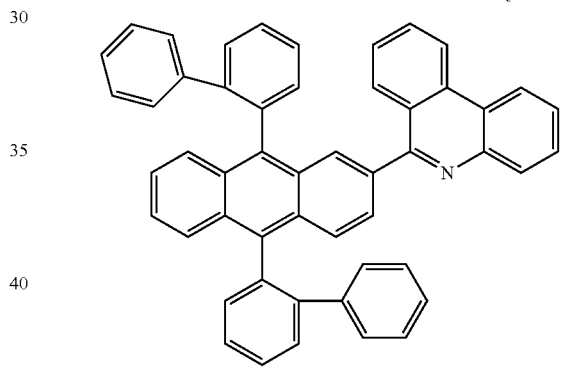
[Formula 2-13]
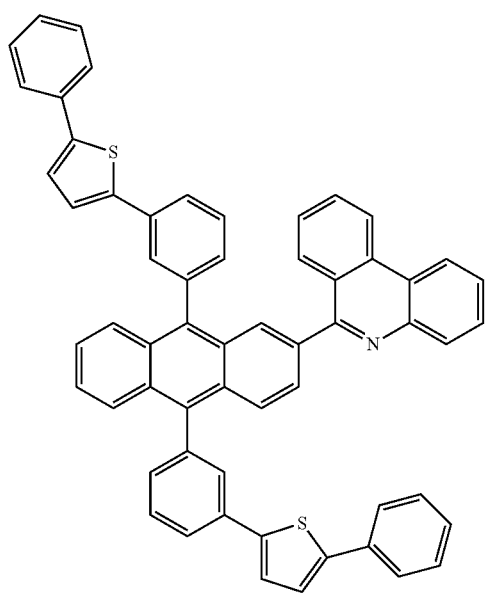
[Formula 2-16]
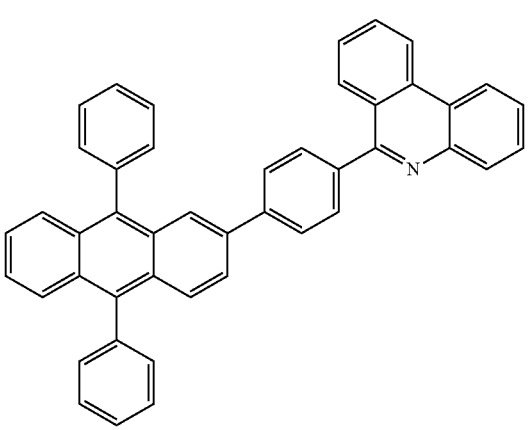

[Formula 2-17]
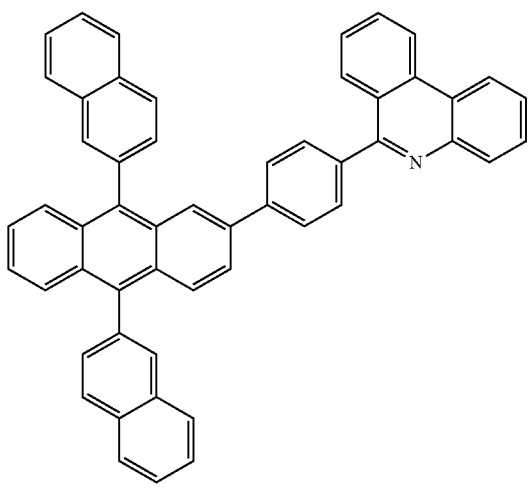
[Formula 2-18]
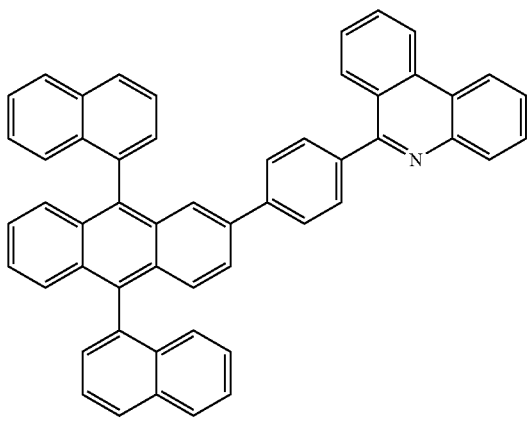
[Formula 2-19]
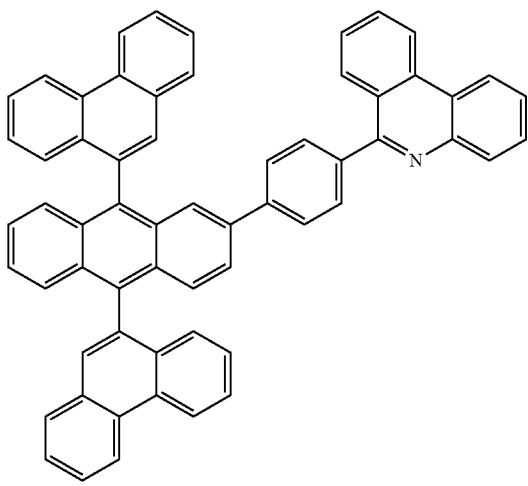
[Formula 2-20]
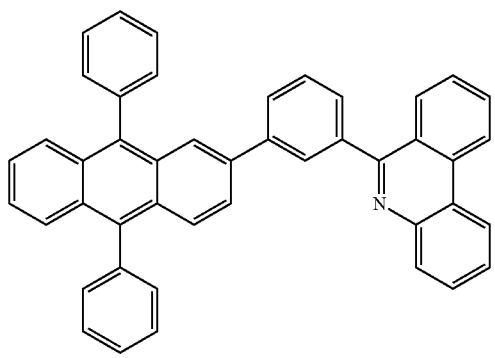
[Formula 2-21]
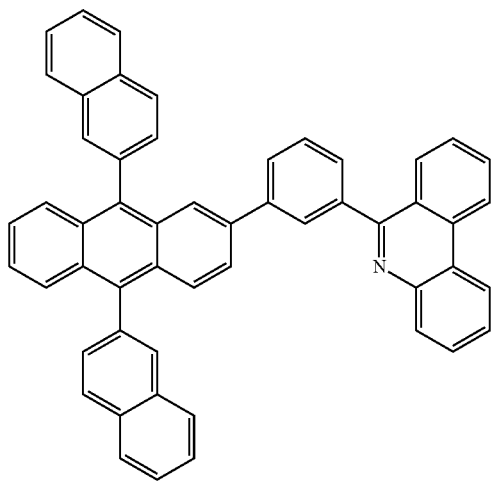
[Formula 2-22]
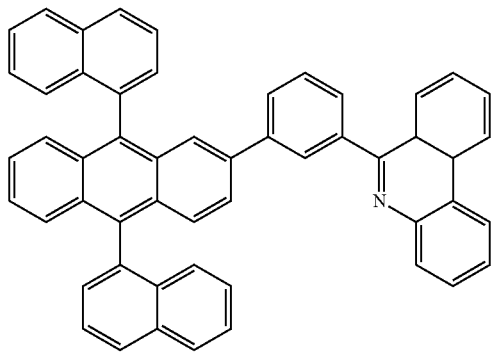

[Formula 2-23]
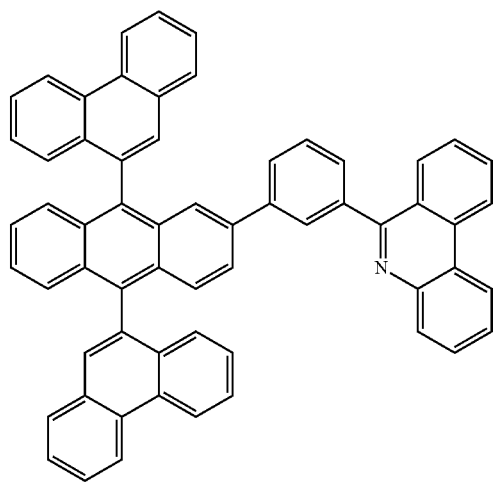
[Formula 2-24]
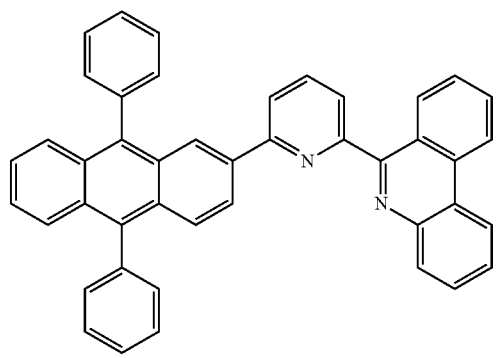
[Formula 2-25]
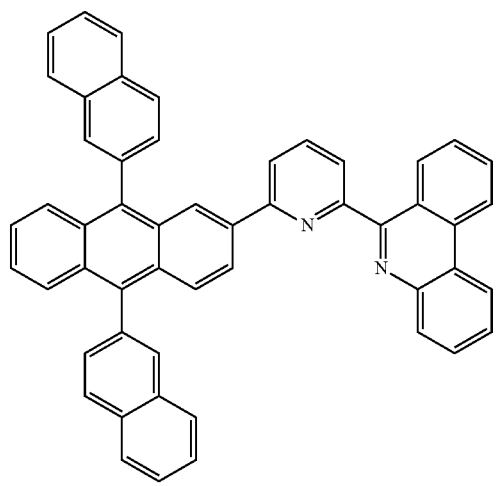
[Formula 2-26]
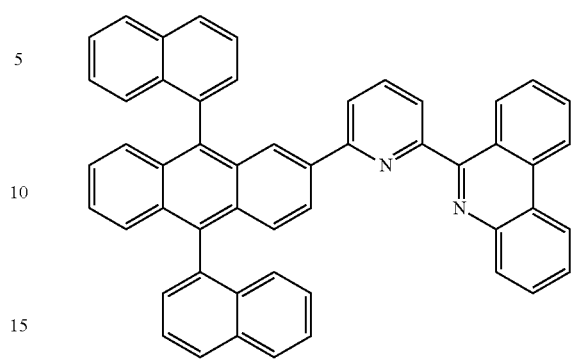
[Formula 2-27]
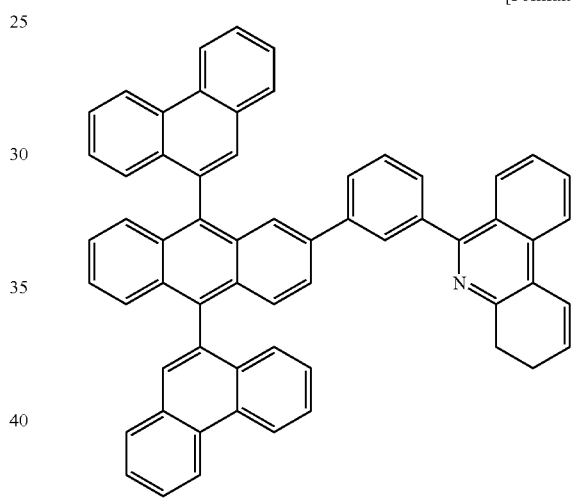
[Formula 2-28]
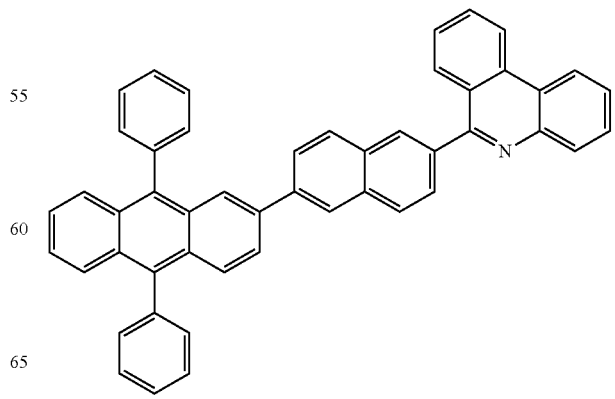

[Formula 2-29]
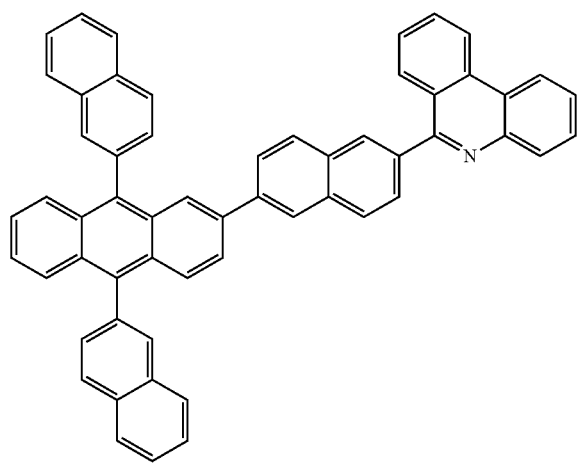
[Formula 2-30]
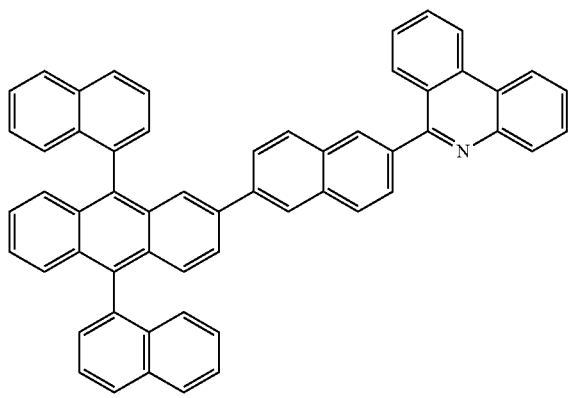
[Formula 2-31]
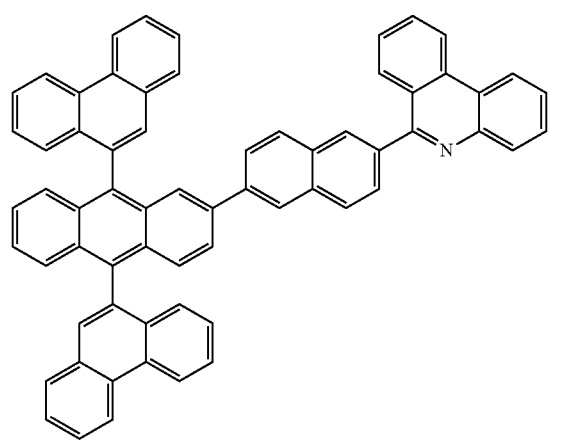
[Formula 2-32]
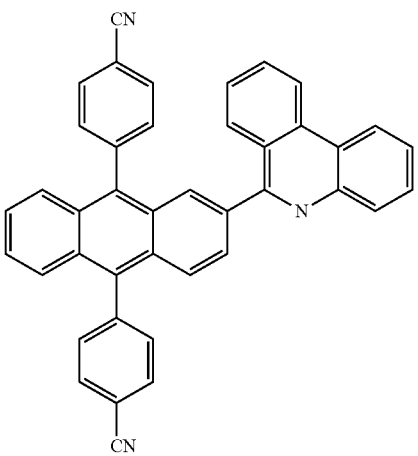
[Formula 2-33]
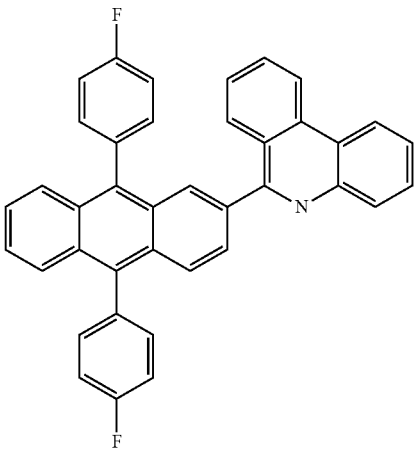
[Formula 2-34]
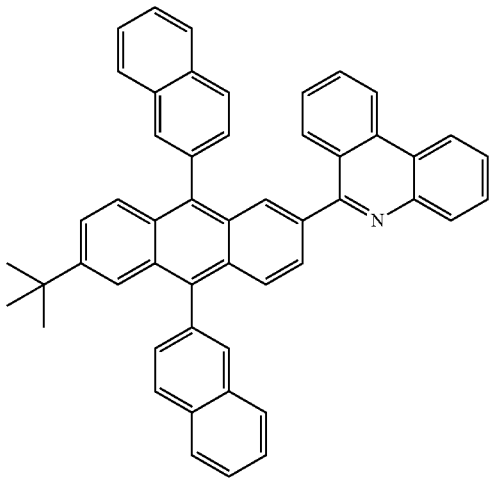

[Formula 2-35]
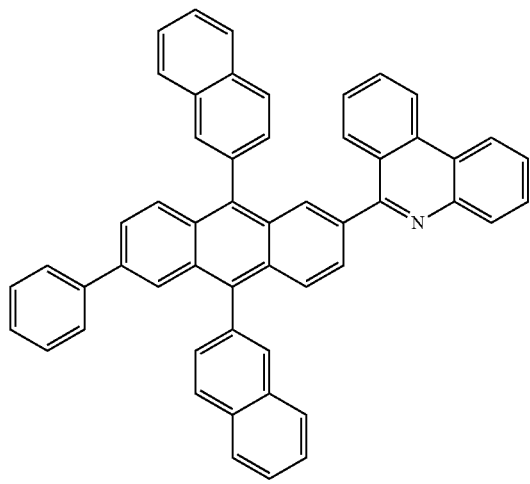
[Formula 2-36]
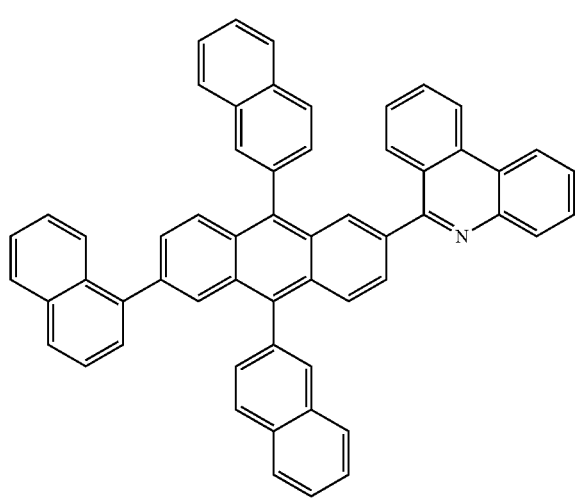
[Formula 2-37]
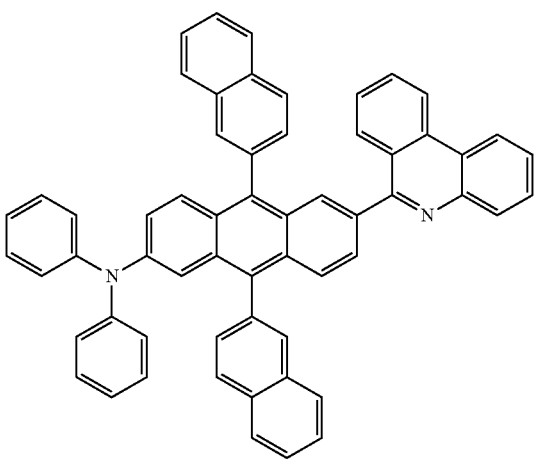
[Formula 2-38]
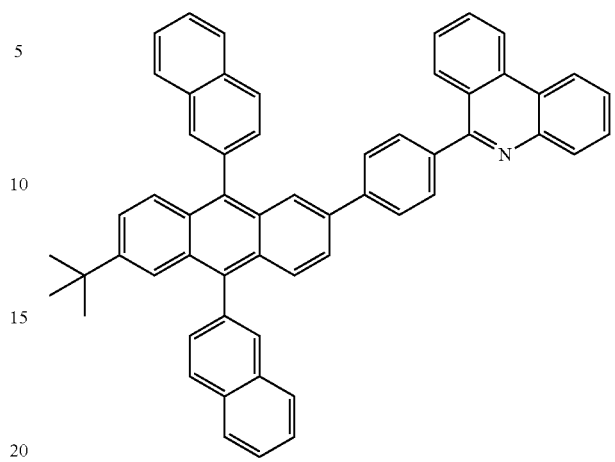
[Formula 2-39]
[Formula 2-40]
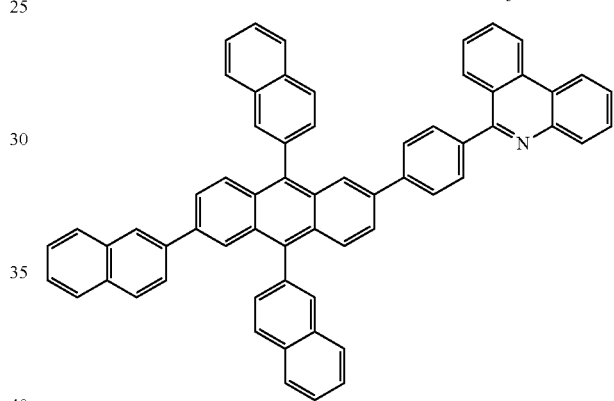
10. The compound according to claim 1, wherein the compound of Formula 1 is selected from the group consisting of the compounds that are represented by the following Formulas 3-1 to 3-40:

[Formula 3-1]
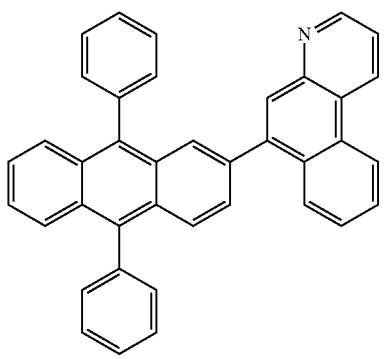
[Formula 3-2]
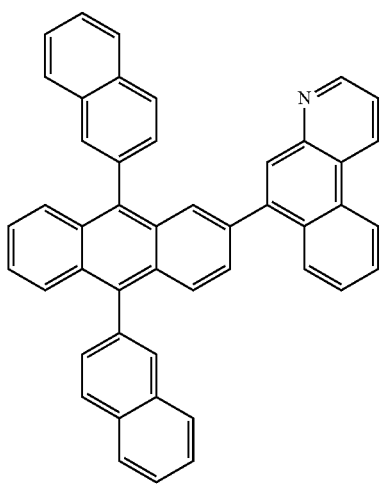
[Formula 3-3]
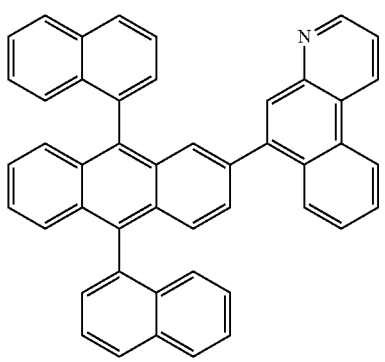
[Formula 3-4]
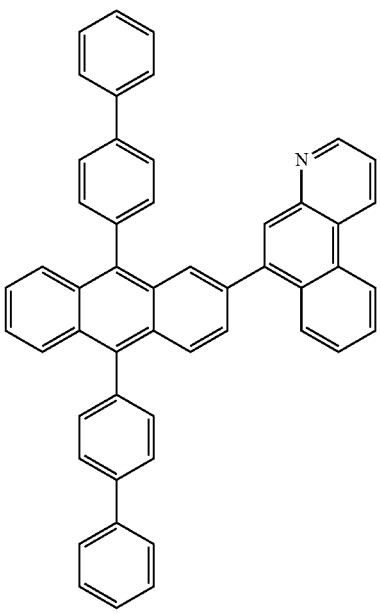
[Formula 3-5]
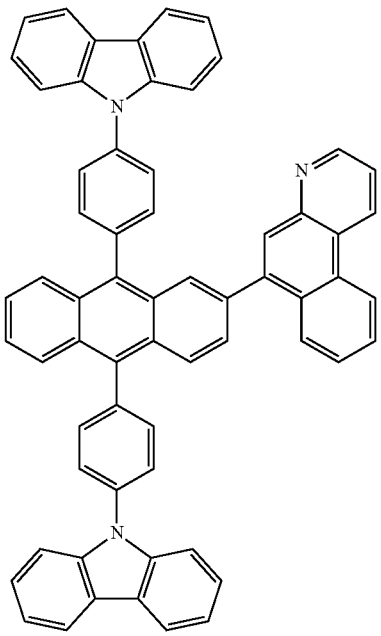

-continued
[Formula 3-6]
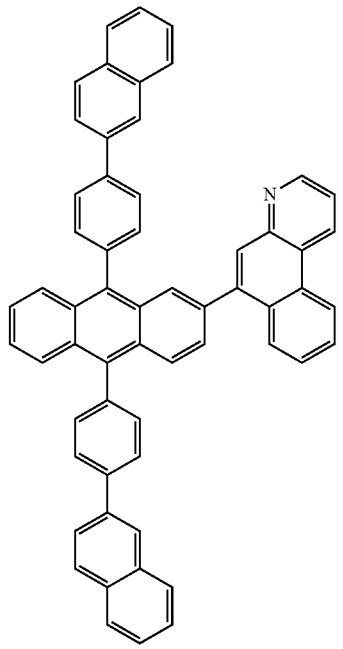
[Formula 3-7]
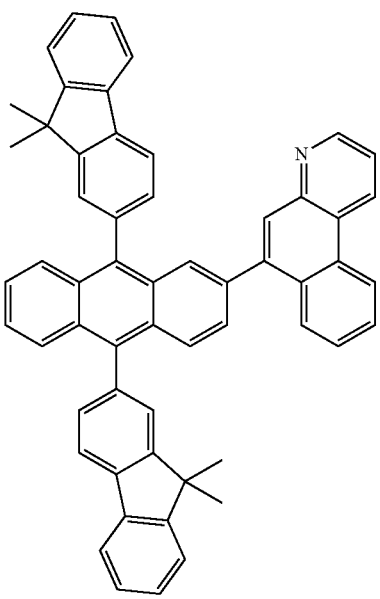
[Formula 3-8]
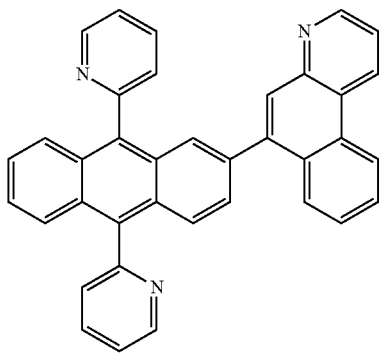
-continued
[Formula 3-9]
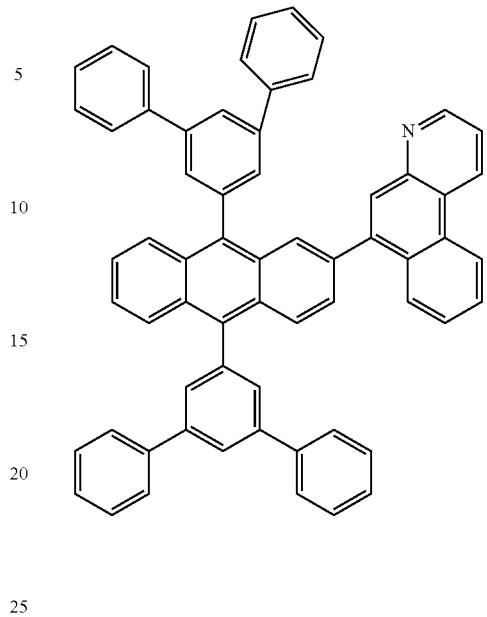
[Formula 3-10]
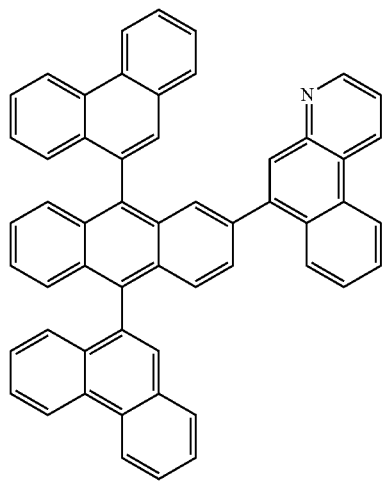
[Formula 3-11]
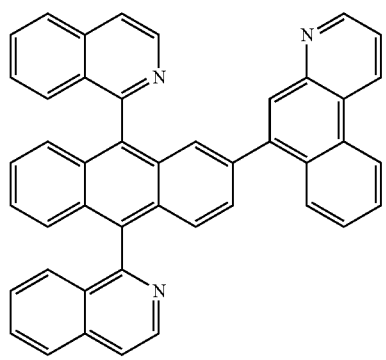

[Formula 3-12]
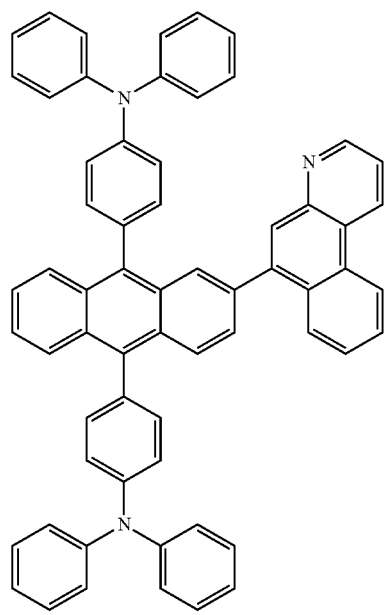
[Formula 3-13]
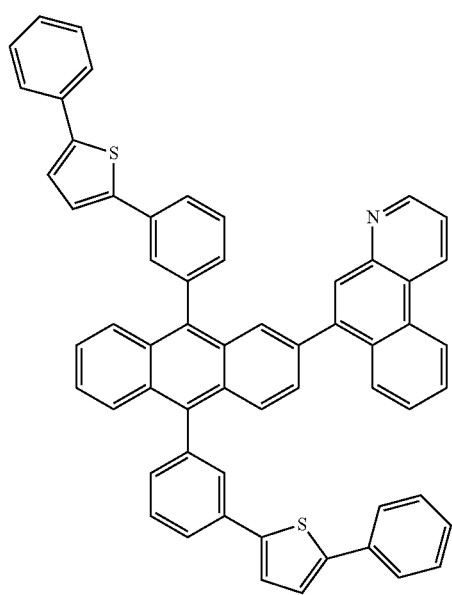
[Formula 3-14]
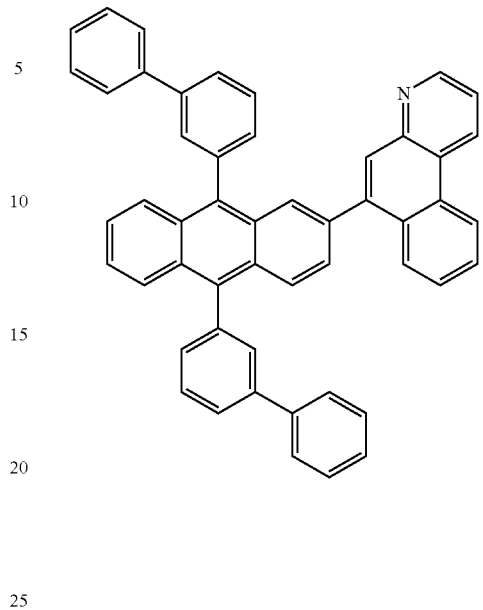
[Formula 3-15]
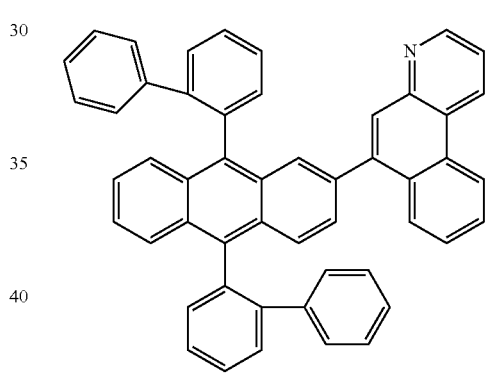
[Formula 3-16]

[Formula 3-17]

[Formula 3-18]

[Formula 3-19]

[Formula 3-20]

[Formula 3-21]

[Formula 3-22]

[Formula 3-23]
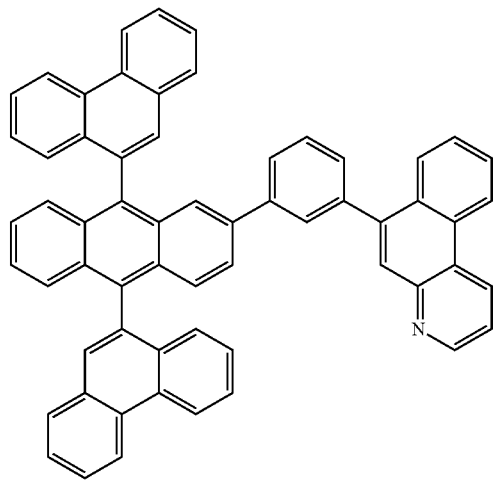
[Formula 3-24]
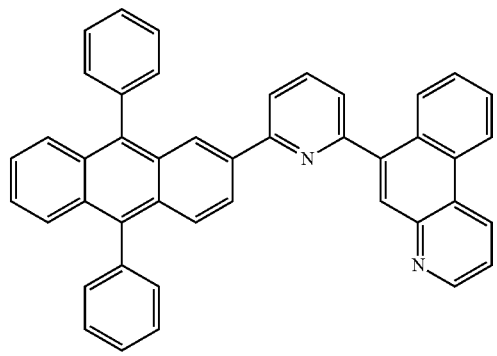
[Formula 3-25]
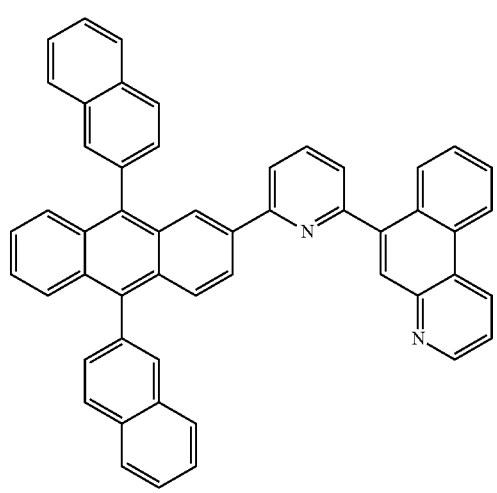
[Formula 3-26]
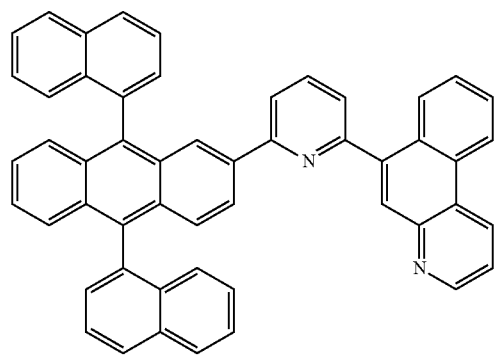
[Formula 3-27]
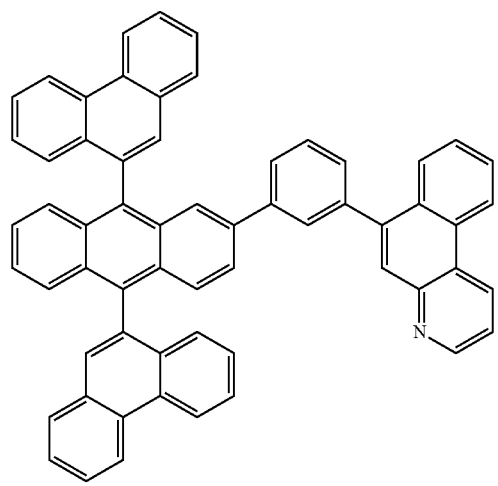
[Formula 3-28]
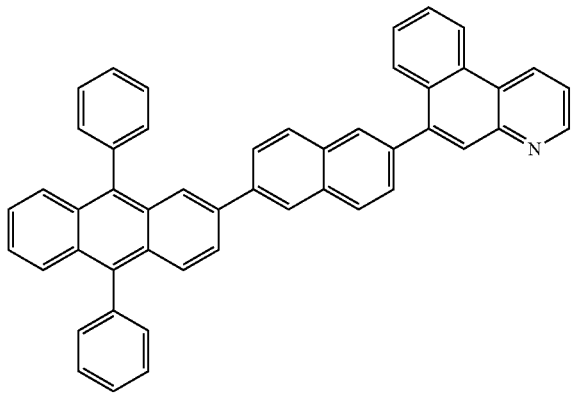

[Formula 3-29]
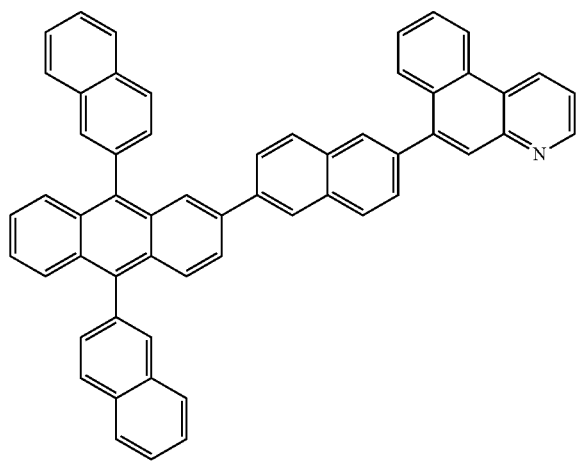
[Formula 3-30]
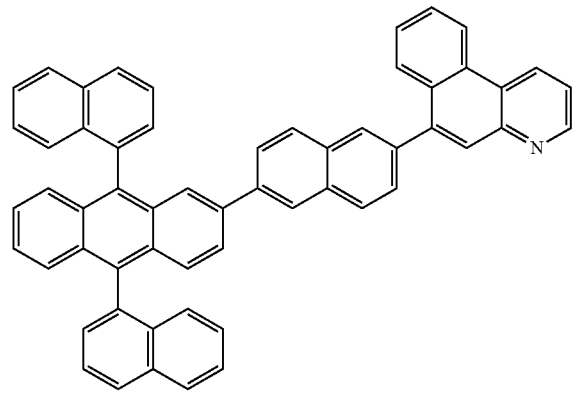
[Formula 3-31]
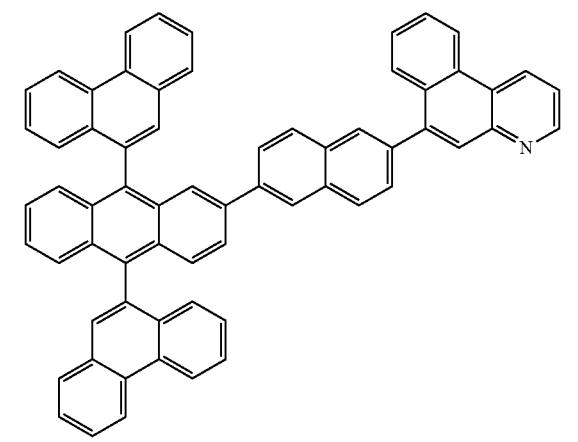
[Formula 3-32]
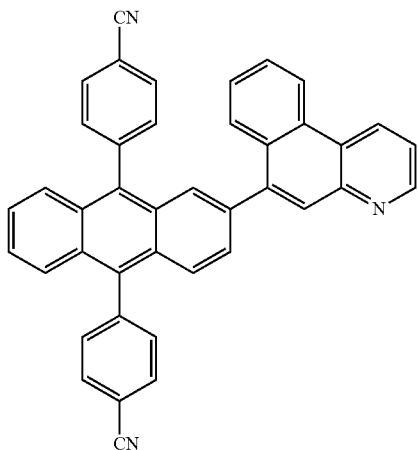
[Formula 3-33]
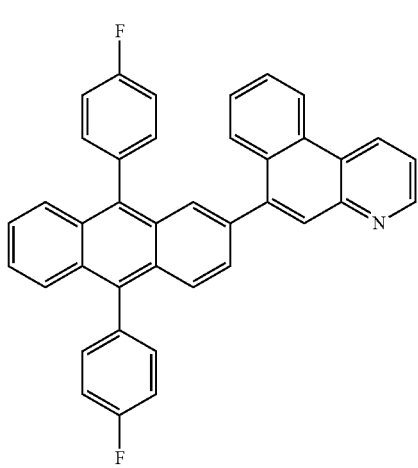
[Formula 3-34]
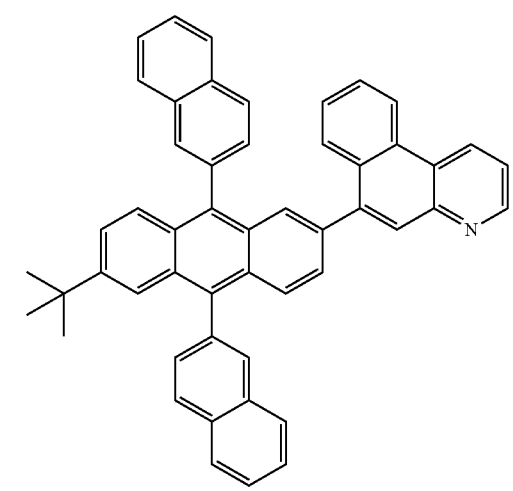

[Formula 3-35]

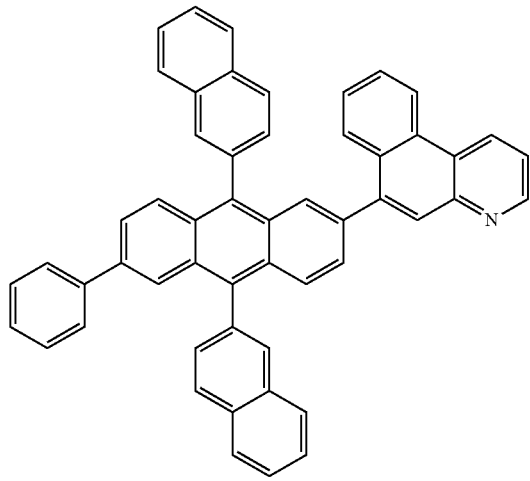

[Formula 3-36]

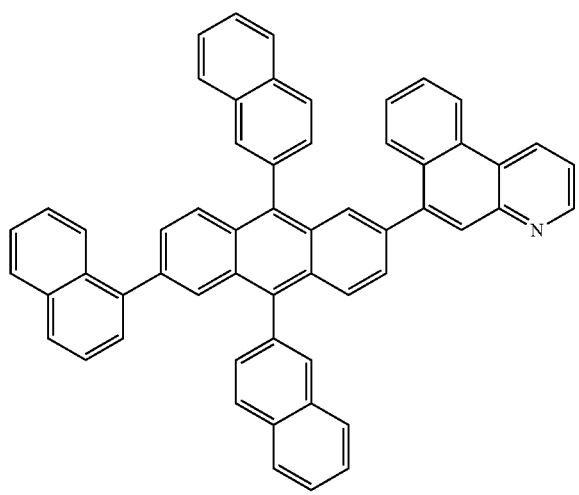

[Formula 3-37]

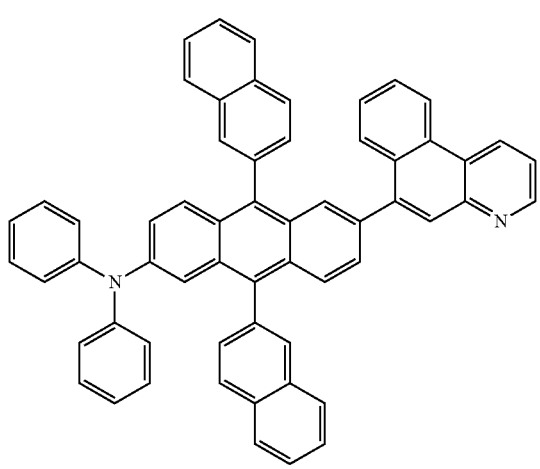

[Formula 3-38]

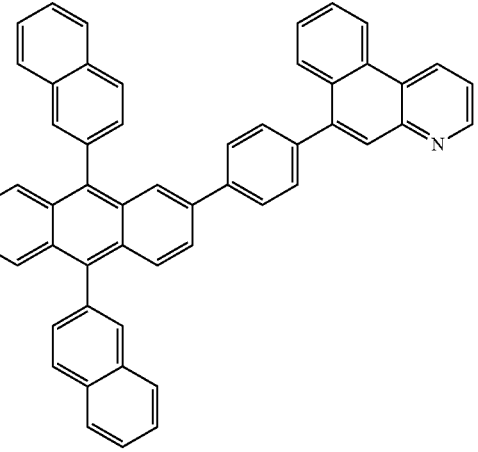

[Formula 3-39]

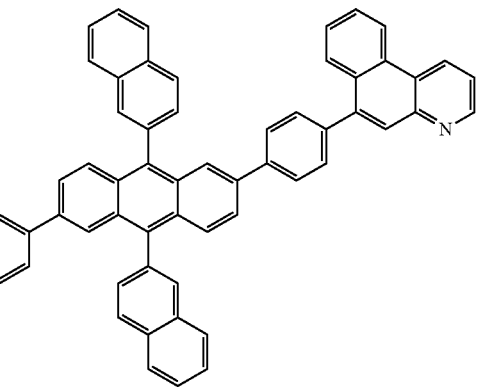

[Formula 3-40]

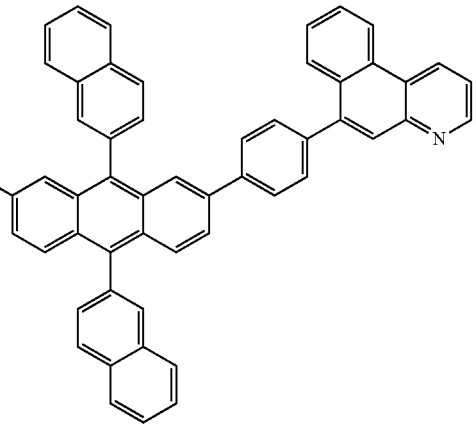

11. An organic electronic device which comprises a first electrode, a second electrode, and at least one organic material layer that is disposed between the first electrode and the second electrode, wherein at least one layer of the organic material layers comprises the compound according to claim 1.

12. The organic electronic device according to 11, wherein the organic electronic device is selected from the group consisting of an organic light emitting device, an organic solar cell, an organic photoconductor (OPC) drum and an organic transistor.

13. The organic electronic device according to claim 12, wherein the organic electronic device is an organic light emitting device.

14. The organic electronic device according to claim 13, wherein the organic light emitting device has a positive direction structure in which an anode, at least one organic material layer and a cathode are sequentially layered on a substrate.

15. The organic electronic device according to claim 13, wherein the organic light emitting device has an inverse direction structure in which a cathode, at least one organic material layer and an anode are sequentially layered on a substrate.

16. The organic electronic device according to claim 13, wherein the organic material layer of the organic light emitting device comprises a hole injection layer, a hole transport layer, a light emitting layer, an electron transport layer and an electron injection layer.

17. The organic electronic device according to claim 13, wherein the organic material layer of the organic light emitting device comprises an electron transport layer, and the electron transport layer comprises the compound of Formula 1.

18. The organic electronic device according to claim 17, wherein the electron transport layer further comprises an alkali metal, an alkali metal compound, an alkali earth metal, an alkali earth metal compound, or a combination thereof.

* * * * *